(12) United States Patent
Oeser et al.

(10) Patent No.: US 11,891,641 B2
(45) Date of Patent: Feb. 6, 2024

(54) OPTIMIZATION OF YEAST HOST CELLS FOR THE PRODUCTION OF HETEROLOGOUS PROTEINS

(71) Applicant: Lallemand USA, Inc., Pembroke, NH (US)

(72) Inventors: Michelle Oeser, Croydon, NH (US); Janet Fisher, Ossipee, NH (US); Aaron Argyros, Lebanon, NH (US)

(73) Assignee: Lallemand USA, Inc., Pembroke, NH (US)

( * ) Notice: Subject to any disclaimer, the term of this patent is extended or adjusted under 35 U.S.C. 154(b) by 139 days.

(21) Appl. No.: 17/277,220

(22) PCT Filed: Sep. 19, 2019

(86) PCT No.: PCT/IB2019/057944
§ 371 (c)(1),
(2) Date: Mar. 17, 2021

(87) PCT Pub. No.: WO2020/058915
PCT Pub. Date: Mar. 26, 2020

(65) Prior Publication Data
US 2022/0049234 A1 Feb. 17, 2022

Related U.S. Application Data

(60) Provisional application No. 62/733,471, filed on Sep. 19, 2018.

(51) Int. Cl.
*C12N 9/88* (2006.01)
*C12N 9/00* (2006.01)
*C12N 15/81* (2006.01)

(52) U.S. Cl.
CPC .............. *C12N 9/00* (2013.01); *C12N 15/81* (2013.01)

(58) Field of Classification Search
CPC ....... C07K 14/39; C07K 14/395; C12N 15/09
See application file for complete search history.

(56) References Cited

U.S. PATENT DOCUMENTS

| 2005/0239164 A1 | 10/2005 | Perrone et al. |
| 2010/0167363 A1 | 7/2010 | Bramucci et al. |
| 2014/0096439 A1 | 4/2014 | Bramucci et al. |

FOREIGN PATENT DOCUMENTS

WO 2017/158189 A1 9/2017

OTHER PUBLICATIONS

Nevoight, "Progress in Metabolic Engineering of *Saccharomyces cerevisiae*," *Microbiology and Molecular Biology Reviews* 72(3):379-412, 2008.
GenBank, "*Saccharomyces cerevisae* strain NCIM3107 chromosome 10 sequence," Accession No. CP009954, Dec. 30, 2014. (101 pages).
Shanmugavel et al., "Probing functional roles of Wilson disease protein (ATP7B) copper-binding domains in yeast," *Metallomics* 9:981-988, 2017.
Ulaganathan et al., "Genome Sequence of *Saccharomyces cerevisae* NCIM3107, Used in Biotethanol Production," *Genome Announcements* 3(1):1-2, Feb. 2015.

*Primary Examiner* — Tekchand Saidha
(74) *Attorney, Agent, or Firm* — Seed IP Law Group LLP

(57) ABSTRACT

The present disclosure concerns yeast host cell especially suited for the expression of heterologous proteins, such as heterologous enzymes. The yeast host cell of the present disclosure exhibits an alteration in the cAMP signaling pathway which allows achieving increased heterologous protein yield and associated biological activity. The yeast host cell can also exhibit polyploidy.

21 Claims, 17 Drawing Sheets
Specification includes a Sequence Listing.

```
S288C    ATGTCATCAAAACCTGATACTGGTTCGGAAATTTCTGGCCCTCAGCGACAGGAAGAACAA  60
M18151   ATGTCATCAAAACCTGATACTGGTTCGGAAATTTCTGGCCCTCAGCGACAGGAAGAACAA  60
M18152   ATGTCATCAAAACCTGATACTGGTTCGGAAATTTCTGGCCCTCAGCGACAGGAAGAACAA  60
         ************************************************************

S288C    GAACAACAGATAGAGCAGAGCTCACCTACGGAAGCAAACGATAGAAGCATTCATGATGAG  120
M18151   GAACAACAGATAGAGCAGAGCTCACCTACGGAAGCAAACGATAGAAGCATTCATGATGAG  120
M18152   GAACAACAGATAGAGCAGAGCTCGCCTACGGAAGCAAACGATAGAAGCATTCATGATGAG  120
         *********************** ************************************

S288C    GTACCAAAAGTCAAGAAGCGTCACGAACAAAATAGTGGTCACAAATCAAGAAGGAATAGC  180
M18151   GTACCAAAAGTCAAGAAGCGTCACGAACAAAATAGTGGTCACAAATCAAGAAGGAATAGC  180
M18152   GTACCAAAAGTCAAGAAGCGTCACGAACAAAATAGTGGTCACAAATCAAGAAGGAATAGC  180
         ************************************************************

S288C    GCATATAGTTATTACAGCCCACGGTCGCTTTCTATGACCAAAAGCAGGGAGAGTATCACT  240
M18151   GCATATAGTTATTACAGCCCACGGTCGCTTTCTATGACCAAAAGCAGGGAGAGTATCACT  240
M18152   GCATATAGTTATTACAGCCCACGGTCGCTTTCTATGACCAAAAGCAGGGAGAGTATCACT  240
         ************************************************************

S288C    CCAAATGGTATGGATGATGTAAGTATTTCGAACGTGGAACATCCAAGGCCGACAGAACCG  300
M18151   CCAAATGGTATGGATGATGTAAGTATTTCGAACGTGGAACATCCAAGGCCGACAGAACCG  300
M18152   CCAAATGGTATGGATGATGTAAGTATTTCGAACGTGGAACATCCAAGGCCGACAGAACCG  300
         ************************************************************

S288C    AAAATCAAAAGGGGTCCATATTTACTGAAGAAAACATTGAGCAGTCTTTCAATGACGAGC  360
M18151   AAAATCAAAAGGGGTCCATATTTACTGAAGAAAACATTGAGCAGTCTTTCAATGACGAGC  360
M18152   AAAATCAAAAGGGGTCCATATTTACTGAAGAAAACATTGAGCAGTCTTTCAATGACGAGC  360
         ************************************************************

S288C    GCGAATAGTACTCATGATGATAATAAAGACCACGGTTACGCTTTGAATTCATCCAAGACG  420
M18151   GCGAATAGTACTCATGATGATAATAAAGACCACGGTTACGCTTTGAATTCATCCAAGACG  420
M18152   GCGAATAGTACTCATGATGATAATAAAGACCACGGTTACGCTTTGAATTCATCCAAGACG  420
         ************************************************************

S288C    CACAACTACACATCTACTCATAACCATCATGACGGTCATCATGATCATCATCATGTTCAG  480
M18151   CACAACTACACATCTACTCATAACCATCATGACGGTCATCATGATCATCATCATGTTCAG  480
M18152   CACAACTACACATCTACTCATAACCATCATGACGGTCATCATGATCATCATCATGTTCAG  480
         ************************************************************

S288C    TTTTTTCCCAATAGGAAGCCATCATTAGCGGAAACCCTATTCAAAAGGTTTTCAGGGTCA  540
M18151   TTTTTTCCCAATAGGAAGCCATCATTAGCGGAAACCCTATTCAAAAGGTTTTCAGGGTCA  540
M18152   TTTTTTCCCAATAGGAAGCCATCATTAGCGGAAACCCTATTCAAAAGGTTTTCAGGGTCA  540
         ************************************************************

S288C    AACAGTCACGATGGCAATAAGTCAGGAAAGGAAAGTAAAGTTGCTAACCTTTCCCTTTCA  600
M18151   AACAGTCACGATGGCAATAAGTCAGGAAAGGAAAGTAAAGTTGCTAACCTTTCCCTTTCA  600
M18152   AACAGTCACGATGGCAATAAGTCAGGAAAGGAAAGTAAAGTTGCTAACCTTTCCCTTTCA  600
         ************************************************************

S288C    ACGGTAAATCCTGCACCTGCTAATAGGAAACCTTCTAAAGACTCCACTTTATCTAATCAC  660
M18151   ACGGTAAATCCTGCACCTGCTAATAGGAAACCTTCTAAAGACTCCACTTTATCTAATCAC  660
M18152   ACGGTAAATCCTGCACCTGCTAATAGGAAACCTTCTAAAGACTCCACTTTATCTAATCAC  660
         ************************************************************

S288C    TTGGCTGATAACGTGCCAAGCACTTTACGAAGGAAAGTGTCCTCATTGGTACGTGGTTCT  720
M18151   TTGGCTGATAACGTGCCAAGCACTTTACGAAGGAAAGTGTCCTCATTGGTACGTGGTTCT  720
M18152   TTGGCTGATAACGTGCCAAGCACTTTACGAAGGAAAGTGTCCTCATTGGTACGTGGTTCT  720
         ************************************************************
```

FIG. 6A

```
S288C    TCCGTCCATGATATAAATAATGGTATTGCAGATAAACAGATTAGACCAAAGNCTGTTGCG  780
M18151   TCCGTCCATGATATAAATAATGGTATTGCAGATAAACAGATTAGACCAAAGNCTGTTGCG  780
M18152   TCCGTCCATGATATAAATAATGGTATTGCAGATAAACAGATTAGACCAAAGNCTGTTGCG  780
         *************************************************** *******

S288C    CAATCAGAAAATACATTACATTCATCCGATGTTCCCAATAGCAAACGCTCGCACAGAAAA  840
M18151   CAATCAGAAAATACATTACATTCATCCGATGTTCCCAATAGCAAACGCTCGCACAGAAAA  840
M18152   CAATCAGAAAATACATTACATTCATCCGATGTTCCCAATAGCAAACGCTCGCACAGAAAA  840
         ************************************************************

S288C    AGCTTTCTGCTAGGCTCCACATCTTCTTCAAGCAGTAGAAGAGGTTCAAATGTCAGTTCA  900
M18151   AGCTTTCTGCTAGGCTCCACATCTTCTTCAAGCAGTAGAAGAGGTTCAAATGTCAGTTCA  900
M18152   AGCTTTCTGCTAGGCTCCACATCTTCTTCAAGCAGTAGAAGAGGTTCAAATGTCAGTTCA  900
         ************************************************************

S288C    ATGACTAACAGTGACAGTGCAAGTATGGCGACGTCGGGTAGTCATGTTCTCCAACATAAC  960
M18151   ATGACTAACAGTGACAGTGCAAGTATGGCGACGTCGGGTAGTCATGTTCTCCAACATAAC  960
M18152   ATGACTAACAGTGACAGTGCAAGTATGGCGACGTCGGGTAGTCATGTTCTCCAACATAAC  960
         ************************************************************

S288C    GTATCTAATGTTTCTCCAACTACTAAAAGTAAGGACAGCGTTAACAGCGAATCCGCCGAT  1020
M18151   GTATCTAATGTTTCTCCAACTACTAAAAGTAAGGACAGCGTTAACAGCGAATCCGCCGAT  1020
M18152   GTATCTAATGTTTCTCCAACTACTAAAAGTAAGGACAGCGTTAACAGCGAATCCGCCGAT  1020
         ************************************************************

S288C    CACACTAATAATAAATCCGAGAAAGTGACTCCAGAATATAATGAGAACATTCCGGAAAAT  1080
M18151   CACACTAATAATAAATCCGAGAAAGTGACTCCAGAATATAATGAGAACATTCCGGAAAAT  1080
M18152   CACACTAATAATAAATCCGAGAAAGTGACTCCAGAATATAATGAGAACATTCCGGAAAAT  1080
         ************************************************************

S288C    TCTAACTCTGACAACAAACGCGAAGCCACAACGCCTACTATAGAAACACCCATTTCATGT  1140
M18151   TCTAACTCTGACAACAAACGCGAAGCCACAACGCCTACTATAGAAACACCCATTTCATGT  1140
M18152   TCTAACTCTGACAACAAACGCGAAGCCACAACGCCTACTATAGAAACACCCATTTCATGT  1140
         ************************************************************

S288C    AAACCATCCCTTTTCAGGCTAGATACAAACCTTGAGGATGTTACTGATATTACAAAGACG  1200
M18151   AAACCATCCCTTTTCAGGCTAGATACAAACCTTGAGGATGTTACTGATATTACAAAGACG  1200
M18152   AAACCATCCCTTTTCAGGCTAGATACAAACCTTGAGGATGTTACTGATATTACAAAGACG  1200
         ************************************************************

S288C    GTGCCACCCACCGCTGTCAATTCTACACTAAATTCTACACACGGGACTGAGACTGCCTCA  1260
M18151   GTGCCACCCACCGCTGTCAATTCTACACTAAATTCTACACACGGGACTGAGACTGCCTCA  1260
M18152   GTGCCACCCACCGCTGTCAATTCTACACTAAATTCTACACACGGGACTGAGACTGCCTCA  1260
         ************************************************************

S288C    CCCAAAACGGTGATCATGCCTGAAGGTCCTAGGAAGTCGGTGTCAATGGCTGATCTCTCC  1320
M18151   CCCAAAACGGTGATCATGCCTGAAGGTCCTAGGAAGTCGGTGTCAATGGCTGATCTCTCC  1320
M18152   CCCAAAACGGTGATCATGCCTGAAGGTCCTAGGAAGTCGGTGTCAATGGCTGATCTCTCC  1320
         ************************************************************

S288C    GTCGCTGCCGCAGCACCTAATGGTGAATTCACATCAACTTCCAATGATAGATCACAATGG  1380
M18151   GTCGCTGCCGCAGCACCTAATGGTGAATTCACATCAACTTCCAATGATAGATCACAATGG  1380
M18152   GTCGCTGCCGCAGCACCTAATGGTGAATTCACATCAACTTCCAATGATAGATCACAATGG  1380
         ************************************************************

S288C    GTAGCACCTCAAAGCTGGGATGTGGAAACCAAAAGGAAAAAAACAAAACCTAAAGGGAGA  1440
M18151   GTAGCACCTCAAAGCTGGGATGTGGAAACCAAAAGGAAAAAAACAAAACCTAAAGGGAGA  1440
M18152   GTAGCACCTCAAAGCTGGGATGTGGAAACCAAAAGGAAAAAAACAAAACCTAAAGGGAGA  1440
         ************************************************************
```

FIG. 6A (cont.)

```
S288C   TCGAAATCAAGAAGGTCAAGTATAGATGCTGATGAACTTGATCCCATGTCACCGGGGCCA 1500
M18151  TCGAAATCAAGAAGGTCAAGTATAGATGCTGATGAACTTGATCCCATGTCACCGGGGCCA 1500
M18152  TCGAAATCAAGAAGGTCAAGTATAGATGCTGATGAACTTGATCCCATGTCACCGGGGCCA 1500
        ************************************************************

S288C   CCTTCAAAAAAGACTCTC------------------------GTCATCATCACGATCGA 1536
M18151  CCTTCAAAAAAGACTCTCGTCATCGTAAGAACCGACACTCTCGTCATCATCACGATCGA 1560
M18152  CCTTCAAAAAAGACTCTCGTCATCGTAAGAACCGACACTCTCGTCATCATCACGATCGA 1560
        ******************                        ******************

S288C   AAGGATAACGAATCAATGGTCACTGCGGGTGACAGTAACTCAAGTTTTGTTGATATATGT 1596
M18151  AAGGATAACGAATCAATGGTCACTGCGGGTGACAGTAACTCAAGTTTTGTTGATATATGT 1620
M18152  AAGGATAACGAATCAATGGTCACTGCGGGTGACAGTAACTCAAGTTTTGTTGATATATGT 1620
        ************************************************************

S288C   AAAGAAAACGTTCCGAATGATAGCAAGACCGCACTCGATACTAAATCTGTGAACCGCTTA 1656
M18151  AAAGAAAACGTTCCGAATGATAGCAAGACCGCACTCGATACTAAATCTGTGAACCGCTTA 1680
M18152  AAAGAAAACGTTCCGAATGATAGCAAGACCGCACTCGATACTAAATCTGTGAACCGCTTA 1680
        ************************************************************

S288C   AAAAGTAATTTGGCTATGAGTCCCCCAAGTATACGATATGCTCCATCAAATTTAGATGGG 1716
M18151  AAAAGTAATTTGGCTATGAGTCCCCCAAGTATACGATATGCTCCATCAAATTTAGATGGG 1740
M18152  AAAAGTAATTTGGCTATGAGTCCCCCAAGTATACGATATGCTCCATCAAATTTAGATGGG 1740
        ************************************************************

S288C   GACTACGACACGTCTTCCACTTCCTCATCTTTACCGTCCTCATCTATTAGTTCAGAAGAT 1776
M18151  GACTACGACACGTCTTCCACTTCCTCATCTTTACCGTCCTCATCTATTAGTTCAGAAGAT 1800
M18152  GACTACGACACGTCTTCCACTTCCTCATCTTTACCGTCCTCATCTATTAGTTCAGAAGAT 1800
        ************************************************************

S288C   ACATCTTCCTGCAGCGATTCCTCTTCGTACACTAACGCGTATATGGAGGCCAACCGAGAG 1836
M18151  ACATCTTCCTGCAGCGATTCCTCTTCGTACACTAACGCGTATATGGAGGCCAACCGAGAG 1860
M18152  ACATCTTCCTGCAGCGATTCCTCTTCGTACACTAACGCGTATATGGAGGCCAACCGAGAG 1860
        ************************************************************

S288C   CAGGATAATAAAACACCGATCCTGAATAAAACGAAATCGTATACCAAGAAATTTACATCC 1896
M18151  CAGGATAATAAAACACCGATCCTGAATAAAACGAAATCGTATACCAAGAAATTTACATCC 1920
M18152  CAGGATAATAAAACACCGATCCTGAATAAAACGAAATCGTATACCAAGAAATTTACATCC 1920
        ************************************************************

S288C   TCTTCGGTAAATATGAATTCACCAGATGGTGCCCAGAGTTCTGGATTATTACTACAAGAT 1956
M18151  TCTTCGGTAAATATGAATTCACCAGATGGTGCCCAGAGTTCTGGATTATTACTACAAGAT 1980
M18152  TCTTCGGTAAATATGAATTCACCAGATGGTGCCCAGAGTTCTGGATTATTACTACAAGAT 1980
        ************************************************************

S288C   GAGAAGGACGATGAGGTCGAGTGCCAACTGGAACATTACTATAAAGATTTCAGTGATTTA 2016
M18151  GAGAAGGACGATGAGGTCGAGTGCCAACTGGAACATTACTATAAAGATTTCAGTGATTTA 2040
M18152  GAGAAGGACGATGAGGTCGAGTGCCAACTGGAACATTACTATAAAGATTTCAGTGATTTA 2040
        ************************************************************

S288C   GATCCAAAGAGGCACTATGCTATTCGTATATTCAATACTGATGACACTTTTACGACTCTC 2076
M18151  GATCCAAAGAGGCACTATGCTATTCGTATATTCAATACTGATGACACTTTTACGACTCTC 2100
M18152  GATCCAAAGAGGCACTATGCTATTCGTATATTCAATACTGATGACACTTTTACGACTCTC 2100
        ************************************************************

S288C   TCATGTACTCCAGCGACTACCGTCGAAGAGATAATACCTGCACTTAAAAGAAAATTTAAC 2136
M18151  TCATGTACTCCAGCGACTACCGTCGAAGAGATAATACCTGCACTTAAAAGAAAATTTAAC 2160
M18152  TCATGTACTCCAGCGACTACCGTCGAAGAGATAATACCTGCACTTAAAAGAAAATTTAAC 2160
        ************************************************************
```

FIG. 6A (cont.)

```
S288C    ATTACAGCGCAAGGGAATTTTCAAATTTCCCTGAAGGTGGGAAAGTTGTCAAAAATTTTG  2196
M18151   ATTACAGCGCAAGGGAATTTTCAAATTTCCCTGAAGGTGGGAAAGTTGTCAAAAATTTTG  2220
M18152   ATTACAGCGCAAGGGAATTTTCAAATTTCCCTGAAGGTGGGAAAGTTGTCAAAAATTTTG  2220
         ************************************************************

S288C    AGACCAACTTCGAAACCTATTTTAATTGAAAGAAAACTTTTACTTTTGAATGGTTATCGA  2256
M18151   AGACCAACTTCGAAACCTATTTTAATTGAAAGAAAACTTTTACTTTTGAATGGTTATCGA  2280
M18152   AGACCAACTTCGAAACCTATTTTAATTGAAAGAAAACTTTTACTTTTGAATGGTTATCGA  2280
         ************************************************************

S288C    AAGTCAGACCCACTTCATATTATGGGTATAGAGGATTTAAGTTTTGTTTTTAAGTTTCTT  2316
M18151   AAGTCAGACCCACTTCATATTATGGGTATAGAGGATTTAAGTTTTGTTTTTAAGTTTCTT  2340
M18152   AAGTCAGACCCACTTCATATTATGGGTATAGAGGATTTAAGTTTTGTTTTTAAGTTTCTT  2340
         ************************************************************

S288C    TTCCATCCTGTCACACCTTCTCACTTTACTCCTGAACAAGAACAAAGAATAATGAGAAGC  2376
M18151   TTCCATCCTGTCACACCTTCTCACTTTACTCCTGAACAAGAACAAAGAATAATGAGAAGC  2400
M18152   TTCCATCCTGTCACACCTTCTCACTTTACTCCTGAACAAGAACAAAGAATAATGAGAAGC  2400
         ************************************************************

S288C    GAATTTGTTCACGTAGATTTAAGGAATATGGATCTGACTACACCTCCCATCATTTTTTAC  2436
M18151   GAATTTGTTCACGTAGATTTAAGGAATATGGATCTGACTACACCTCCCATCATTTTTTAC  2460
M18152   GAATTTGTTCACGTAGATTTAAGGAATATGGATCTGACTACACCTCCCATCATTTTTTAC  2460
         ************************************************************
                                                           ↓
S288C    CAGCATACGTCAGAAATAGAAAGTTTAGACGTTTCTAATAACGCAAATATATTCCTACCT  2496
M18151   CAGCATACGTCAGAAATAGAAAGTTTAGACGTTTCTAATAACGTAAATATATTCCTACCT  2520
M18152   CAGCATACGTCAGAAATAGAAAGTTTAGACGTTTCTAATAACGCAAATATATTCCTACCT  2520
         *******************************************  ***************

S288C    CTGGAGTTCATTGAAAGCTCGATTAAATTATTAAGTTTGAGAATGGTTAATATTAGAGCA  2556
M18151   CTGGAGTTCATTGAAAGCTCGATTAAATTATTAAGTTTGAGAATGGTTAATATTAGAGCA  2580
M18152   CTGGAGTTCATTGAAAGCTCGATTAAATTATTAAGTTTGAGAATGGTTAATATTAGAGCA  2580
         ************************************************************
                            ↓
S288C    TCTAAATTTCCTTCCAATATCACTAAGGCGTATAAACTAGTATCTTTGGAATTACAGAGA  2616
M18151   TCTAAATTTCCTTCCAATATCACTAAGGCGTATAAACTAGTATCTTTGGAATTACAGAGA  2640
M18152   TCTAAATTTCCTTCCAATATCACTGAGGCGTATAAACTAGTATCTTTGGAATTACAGAGA  2640
         ************************ ***********************************

S288C    AACTTCATAAGAAAAGTACCGAACTCAATCATGAAACTGAGTAATTTAACGATATTAAAC  2676
M18151   AACTTCATAAGAAAAGTACCGAACTCAATCATGAAACTGAGTAATTTAACGATATTAAAC  2700
M18152   AACTTCATAAGAAAAGTACCGAACTCAATCATGAAACTGAGTAATTTAACGATATTAAAC  2700
         ************************************************************

S288C    CTTCAATGTAATGAGCTTGAAAGCCTACCGGCTGGATTTGTTGAACTGAAAAATCTGCAA  2736
M18151   CTTCAATGTAATGAGCTTGAAAGCCTACCGGCTGGATTTGTTGAACTGAAAAATCTGCAA  2760
M18152   CTTCAATGTAATGAGCTTGAAAGCCTACCGGCTGGATTTGTTGAACTGAAAAATCTGCAA  2760
         ************************************************************

S288C    TTGCTAGACTTGTCTTCAAACAAGTTCATGCACTACCCAGAAGTTATTAACTACTGCACC  2796
M18151   TTGCTAGACTTGTCTTCAAACAAGTTCATGCACTACCCAGAAGTTATTAACTACTGCACC  2820
M18152   TTGCTAGACTTGTCTTCAAACAAGTTCATGCACTACCCAGAAGTTATTAACTACTGCACC  2820
         ************************************************************

S288C    AATCTTTTACAAATAGACCTATCATATAATAAAATCCAAAGCTTACCACAGTCCACTAAG  2856
M18151   AATCTTTTACAAATAGACCTATCATATAATAAAATCCAAAGCTTACCACAGTCCACTAAG  2880
M18152   AATCTTTTACAAATAGACCTATCATATAATAAAATCCAAAGCTTACCACAGTCCACTAAG  2880
         ************************************************************
```

FIG. 6A (cont.)

```
S288C    TACCTAGTAAAGCTTGCGAAGATGAACCTTTCTCATAACAAACTAAATTTTATAGGCGAC  2916
M18151   TACCTAGTAAAGCTTGCGAAGATGAACCTTTCTCATAACAAACTAAATTTTATAGGCGAC  2940
M18152   TACCTAGTAAAGCTTGCGAAGATGAACCTTTCTCATAACAAACTAAATTTTATAGGCGAC  2940
         ************************************************************

S288C    TTATCGGAAATGACAGATTTGAGGACGCTGAACCTAAGATATAACAGAATATCATCAATT  2976
M18151   TTATCGGAAATGACAAATTTGAGGACGCTGAACCTAAGATATAACAGAATATCATCAATT  3000
M18152   TTATCGGAAATGACAAATTTGAGGACGCTGAACCTAAGATATAACAGAATATCATCAATT  3000
         *************** ********************************************

S288C    AAGACAAATGCGTCTAACTTGCAGAACCTTTTTTTAACAGATAATAGAATTTCGAACTTT  3036
M18151   AAGACAAATGCGTCTAACTTGCAGAACCTTTTTTTAACAGATAATAGAATTTCGAACTTT  3060
M18152   AAGACAAATGCGTCTAACTTGCAGAACCTTTTTTTAACAGATAATAGAATTTCGAACTTT  3060
         ************************************************************

S288C    GAAGACACTTTGCCGAAACTAAGAGCCCTTGAAATTCAAGAGAATCCAATCACTTCTATA  3096
M18151   GAAGACACTTTGCCGAAACTAAGAGCCCTTGAAATTCAAGAGAATCCAATCACTTCTATA  3120
M18152   GAAGACACTTTGCCGAAACTAAGAGCCCTTGAAATTCAAGAGAATCCAATCACTTCTATA  3120
         ************************************************************

S288C    TCCTTCAAAGATTTTTATCCAAAAAACATGACAAGTTTGACGTTGAACAAGGCACAGTTA  3156
M18151   TCCTTCAAAGATTTTTATCCAAAAAACATGACAAGTTTGACGTTGAACAAGGCACAGTTA  3180
M18152   TCCTTCAAAGATTTTTATCCAAAAAACATGACAAGTTTGACGTTGAACAAGGCACAGTTA  3180
         ************************************************************

S288C    TCGAGTATTCCTGGAGAATTACTCACCAAACTATCTTTCCTCGAGAAACTTGAACTTAAT  3216
M18151   TCGAGTATTCCTGGAGAATTACTCACCAAACTATCTTTCCTCGAGAAACTTGAACTTAAT  3240
M18152   TCGAGTATTCCTGGAGAATTACTCACCAAACTATCTTTCCTCGAGAAACTTGAACTTAAT  3240
         ************************************************************

S288C    CAGAATAATTTGACTAGACTGCCACAGGAGATATCCAAGTTGACTAAATTAGTTTTCCTT  3276
M18151   CAGAATAATTTGACTAGACTGCCACAGGAGATATCCAAGTTGACTAAATTAGTTTTCCTT  3300
M18152   CAGAATAATTTGACTAGACTGCCACAGGAGATATCCAAGTTGACTAAATTAGTTTTCCTT  3300
         ************************************************************

S288C    TCAGTGGCGAGAAACAAACTAGAGTATATTCCACCCGAGCTATCTCAACTGAAAAGTTTG  3336
M18151   TCAGTGGCGAGAAACAAACTAGAGTATATTCCACCCGAGCTATCTCAACTGAAAAGTTTG  3360
M18152   TCAGTGGCGAGAAACAAACTAGAGTATATTCCACCCGAGCTATCTCAACTGAAAAGTTTG  3360
         ************************************************************

S288C    AGGACATTAGATCTACATTCTAACAACATAAGGGACTTTGTTGACGGTATGGAAAACCTT  3396
M18151   AGGACATTAGATCTACATTCTAACAACATAAGGGACTTTGTTGACGGTATGGAAAACCTT  3420
M18152   AGGACATTAGATCTACATTCTAACAACATAAGGGACTTTGTTGACGGTATGGAAAACCTT  3420
         ************************************************************

S288C    GAACTAACATCGCTAAATATTTCATCGAATGCATTCGGTAACTCTAGCTTAGAAAATTCT  3456
M18151   GAACTAACATCGCTAAATATTTCATCGAATGCATTCGGTAACTCTAGCTTAGAAAATTCT  3480
M18152   GAACTAACATCGCTAAATATTTCATCGAATGCATTCGGTAACTCTAGCTTAGAAAATTCT  3480
         ************************************************************

S288C    TTTTACCATAACATGTCATATGGGTCAAAGTTATCTAAAAGCCTGATGTTTTTTATTGCT  3516
M18151   TTTTACCATAACATGTCATATGGGTCAAAGTTATCTAAAAGCCTGATGTTTTTTATTGCT  3540
M18152   TTTTACCATAACATGTCATATGGGTCAAAGTTATCTAAAAGCCTGATGTTTTTTATTGCT  3540
         ************************************************************

S288C    GCAGACAATCAATTTGATGATGCTATGTGGCCTCTTTTCAATTGCTTTGTCAATCTGAAA  3576
M18151   GCAGACAATCAATTTGATGATGCTATGTGGCCTCTTTTCAATTGCTTTGTCAATCTGAAA  3600
M18152   GCAGACAATCAATTTGATGATGCTATGTGGCCTCTTTTCAATTGCTTTGTCAATCTGAAA  3600
         ************************************************************
```

FIG. 6A (cont.)

```
S288C    GTGCTAAATCTTTCTTACAACAATTTTTCAGATGTATCGCACATGAAACTTGAGAGCATT  3636
M18151   GTGCTAAATCTTTCTTACAACAATTTTTCAGATGTATCGCACATGAAACTTGAGAGCATT  3660
M18152   GTGCTAAATCTTTCTTACAACAATTTTTCAGATGTATCGCACATGAAACTTGAGAGCATT  3660
         ************************************************************

S288C    ACCGAATTGTACCTCTCCGGTAATAAGCTCACGACATTGTCGGGTGATACAGTTTTGAAA  3696
M18151   ACCGAATTGTACCTCTCCGGTAATAAGCTCACGACATTGTCGGGTGATACAGTTTTGAAA  3720
M18152   ACCGAATTGTACCTCTCCGGTAATAAGCTCACGACATTGTCGGGTGATACAGTTTTGAAA  3720
         ************************************************************

S288C    TGGAGCTCTTTAAAGACTTTAATGTTGAATAGTAACCAAATGTTATCTCTGCCTGCAGAA  3756
M18151   TGGAGCTCTTTAAAGACTTTAATGTTGAATAGTAACCAAATGTTATCTCTGCCTGCAGAA  3780
M18152   TGGAGCTCTTTAAAGACTTTAATGTTGAATAGTAACCAAATGTTATCTCTGCCTGCAGAA  3780
         ************************************************************

S288C    TTATCAAATCTCTCACAGCTAAGTGTATTTGATGTTGGAGCAAATCAATTAAAGTATAAT  3816
M18151   TTATCAAATCTCTCACAGCTAAGTGTATTTGATGTTGGAGCAAATCAATTAAAGTATAAT  3840
M18152   TTATCAAATCTCTCACAGCTAAGTGTATTTGATGTTGGAGCAAATCAATTAAAGTATAAT  3840
         ************************************************************

S288C    ATATCAAACTATCATTACGATTGGAACTGGAGGAATAATAAAGAACTAAAATATTTGAAT  3876
M18151   ATATCAAACTATCATTACGATTGGAACTGGAGGAATAATAAAGAACTAAAATATTTGAAT  3900
M18152   ATATCAAACTATCATTACGATTGGAACTGGAGGAATAATAAAGAACTAAAATATTTGAAT  3900
         ************************************************************

S288C    TTTTCAGGAAATCGAAGGTTTGAAATAAAGTCATTTATAAGTCACGATATTGATGCTGAT  3936
M18151   TTTTCAGGAAATCGAAGGTTTGAAATAAAGTCATTTATAAGTCACGATATTGATGCTGAT  3960
M18152   TTTTCAGGAAATCGAAGGTTTGAAATAAAGTCATTTATAAGTCACGATATTGATGCTGAT  3960
         ************************************************************

S288C    TTGTCAGATCTGACAGTATTACCTCAGTTAAAGGTACTAGGTTTAATGGACGTAACTTTA  3996
M18151   TTGTCAGATCTGACAGTATTACCTCAGTTAAAGGTACTAGGTTTAATGGACGTAACTTTA  4020
M18152   TTGTCAGATCTGACAGTATTACCTCAGTTAAAGGTACTAGGTTTAATGGACGTAACTTTA  4020
         ************************************************************

S288C    AATACTACCAAAGTACCGGATGAAAATGTCAATTTCCGTTTAAGGACAACTGCATCAATA  4056
M18151   AATACTACCAAAGTACCGGATGAAAATGTCAATTTCCGTTTAAGGACAACTGCATCAATA  4080
M18152   AATACTACCAAAGTACCGGATGAAAATGTCAATTTCCGTTTAAGGACAACTGCATCAATA  4080
         ************************************************************

S288C    ATAAATGGGATGCGCTACGGTGTTGCTGATACATTAGGTCAAAGAGACTATGTGTCATCT  4116
M18151   ATAAATGGGATGCGCTACGGTGTTGCTGATACATTAGGTCAAAGAGACTATGTGTCATCT  4140
M18152   ATAAATGGGATGCGCTACGGTGTTGCTGATACATTAGGTCAAAGAGACTATGTGTCATCT  4140
         ************************************************************

S288C    CGTGATGTTACCTTTGAAAGATTCCGCGGAAATGACGACGAATGCTTACTATGTCTTCAT  4176
M18151   CGTGATGTTACCTTTGAAAGATTCCGCGGAAATGACGACGAATGCTTACTATGTCTTCAT  4200
M18152   CGTGATGTTACCTTTGAAAGATTCCGCGGAAATGACGACGAATGCTTACTATGTCTTCAT  4200
         ************************************************************

S288C    GATAGTAAAAACCAAAATGCAGATTATGGCCACAATATATCAAGAATTGTTAGAGATATT  4236
M18151   GATAGTAAAAACCAAAATGCAGATTATGGCCACAATATATCAAGAATTGTTAGAGATATT  4260
M18152   GATAGTAAAAACCAAAATGCAGATTATGGCCACAATATATCAAGAATTGTTAGAGATATT  4260
         ************************************************************
S288C    TACGATAAAATACTGATCAGACAACTGGAAAGGTATGGAGACGAAACAGATGATAATATA  4296
M18151   TACGATAAAATACTGATCAGACAACTGGAAAGGTATGGAGACGAAACAGATGATAATATA  4320
M18152   TACGATAAAATACTGATCAGACAACTGGAAAGGTATGGAGACGACACAGATGATAATATA  4320
         ******************************************* ****************
```

FIG. 6A (cont.)

```
S288C   AAAACTGCACTTCGTTTCAGTTTTTTGCAACTGAATAAGGAGATTAACGGAATGCTAAAT  4356
M18151  AAAACTGCACTTCGTTTCAGTTTTTTGCAACTGAATAAGGAGATTAACGGAATGCTAAAT  4380
M18152  AAAACTGCACTTCGTTTCAGTTTTTTGCAACTGAATAAGGAGATTAACGGAATGCTAAAT  4380
        ************************************************************

S288C   TCTGTTGATAATGGTGCCGATGTTGCCAATCTTTCATATGCAGACTTGCTAAGTGGCGCT  4416
M18151  TCTGTTGATAATGGTGCCGATGTTGCCAATCTTTCATATGCAGACTTGCTAAGTGGCGCT  4440
M18152  TCTGTTGATAATGGTGCCGATGTTGCCAATCTTTCATATGCAGACTTGCTAAGTGGCGCT  4440
        ************************************************************

S288C   TGCTCTACTGTGATATATATCAGAGGGAAGAAACTCTTCGCTGCAAATTTAGGTGACTGT  4476
M18151  TGCTCTACTGTGATATATATCAGAGGGAAGAAACTCTTCGCTGCAAATTTAGGTGACTGT  4500
M18152  TGCTCTACTGTGATATATATCAGAGGGAAGAAACTCTTCGCTGCAAATTTAGGTGACTGT  4500
        ************************************************************

S288C   ATGGCTATTTTATCCAAAAACAATGGTGACTACCAAACGCTAACCAAACAACATCTCCCA  4536
M18151  ATGGCTATTTTATCCAAAAACAATGGTGACTACCAAACGCTAACCAAACAACATCTCCCA  4560
M18152  ATGGCTATTTTATCCAAAAACAATGGTGACTACCAAACGCTAACCAAACAACATCTCCCA  4560
        ************************************************************

S288C   ACAAAGCGGGAAGAATACGAGAGGATCAGAATATCTGGCGGGTATGTCAACAATGGAAAA  4596
M18151  ACAAAGCGGGAAGAATACGAGAGGATCAGAATATCTGGCGGGTATGTCAACAATGGAAAA  4620
M18152  ACAAAGCGGGAAGAATACGAGAGGATCAGAATATCTGGCGGGTATGTCAACAATGGAAAA  4620
        ************************************************************

S288C   TTAGATGGTGTTGTAGATGTGTCTAGAGCAGTGGGTTTTTTTGATTTGCTTCCCCACATT  4656
M18151  TTAGATGGTGTTGTAGATGTGTCTAGAGCAGTGGGTTTTTTTGATTTGCTTCCCCACATT  4680
M18152  TTAGATGGTGTTGTAGATGTGTCTAGAGCAGTGGGTTTTTTTGATTTGCTTCCCCACATT  4680
        ************************************************************

S288C   CATGCTTCTCCCGACATATCTGTCGTGACATTAACAAAAGCAGACGAGATGCTTATTGTA  4716
M18151  CATGCTTCTCCCGACATATCTGTCGTGACATTAACAAAAGCAGACGAGATGCTTATTGTA  4740
M18152  CATGCTTCTCCCGACATATCTGTCGTGACATTAACAAAAGCAGACGAGATGCTTATTGTA  4740
        ************************************************************

S288C   GCAACGCATAAGTTATGGGAATACATGGACGTGGATACAGTTTGTGATATCGCGCGTGAG  4776
M18151  GCAACGCATAAGTTATGGGAATACATGGACGTGGATACAGTTTGTGATATCGCGCGTGAG  4800
M18152  GCAACGCATAAGTTATGGGAATACATGGACGTGGATACAGTTTGTGATATCGCGCGTGAG  4800
        ************************************************************

S288C   AATAGTACTGATCCACTCCGTGCCGCAGCTGAGTTGAAGGATCATGCCATGGCTTACGGC  4836
M18151  AATAGTACTGATCCACTCCGTGCCGCAGCTGAGTTGAAGGATCATGCCATGGCTTACGGC  4860
M18152  AATAGTACTGATCCACTCCGTGCCGCAGCTGAGTTGAAGGATCATGCCATGGCTTACGGC  4860
        ************************************************************

S288C   TGTACAGAGAATATTACAATTTTGTGCCTTGCTCTTTACGAGAACATTCAGCAACAAAAT  4896
M18151  TGTACAGAGAATATTACAATTTTGTGCCTTGCTCTTTACGAGAACATTCAGCAACAAAAT  4920
M18152  TGTACAGAGAATATTACAATTTTGTGCCTTGCTCTTTACGAGAACATTCAGCAACAAAAT  4920
        ************************************************************

S288C   CGGTTCACTTTAAATAAAAACTCTTTAATGACTAGAAGAAGTACTTTCGAGGATACTACA  4956
M18151  CGGTTCACTTTAAATAAAAACTCTTTAATGACTAGAAGAAGTACTTTCGAGGATACTACA  4980
M18152  CGGTTCACTTTAAATAAAAACTCTTTAATGACTAGAAGAAGTACTTTCGAGGATACTACA  4980
        ************************************************************

S288C   TTAAGAAGACTTCAACCTGAGATTTCTCCGCCAACAGGTAACCTAGCAATGGTCTTCACT  5016
M18151  TTAAGAAGACTTCAACCTGAGATTTCTCCGCCAACAGGTAACCTAGCAATGGTCTTCACT  5040
M18152  TTAAGAAGACTTCAACCTGAGATTTCTCCGCCAACAGGTAACCTAGCAATGGTCTTCACT  5040
        ************************************************************
```

FIG. 6A (cont.)

```
S288C    GATATCAAAAGCTCAACCTTCTTATGGGAGCTATTCCCTAACGCAATGAGGACCGCAATA  5076
M18151   GATATCAAAAGCTCAACCTTCTTATGGGAGCTATTCCCTAACGCAATGAGGACCGCAATA  5100
M18152   GATATCAAAAGCTCAACCTTCTTATGGGAGCTATTCCCTAACGCAATGAGGACCGCAATA  5100
         ************************************************************

S288C    AAAACTCACAATGACATTATGCGTCGTCAACTACGAATTTACGGTGGTTACGAAGTAAAG  5136
M18151   AAAACTCACAATGACATTATGCGTCGTCAACTACGAATTTACGGTGGTTACGAAGTAAAG  5160
M18152   AAAACTCACAATGACATTATGCGTCGTCAACTACGAATTTACGGTGGTTACGAAGTAAAG  5160
         ************************************************************

S288C    ACAGAAGGAGACGCCTTTATGGTGGCATTTCCTACGCCAACTAGTGGTCTGACATGGTGC  5196
M18151   ACAGAAGGAGACGCCTTTATGGTGGCATTTCCTACGCCAACTAGTGGTCTGACATGGTGC  5220
M18152   ACAGAAGGAGACGCCTTTATGGTGGCATTTCCTACGCCAACTAGTGGTCTTACATGGTGC  5220
         ************************************************** *********

S288C    TTAAGTGTTCAATTAAAACTCTTGGATGCACAATGGCCGGAGGAAATTACCTCAGTTCAA  5256
M18151   TTAAGTGTTCAATTAAAACTCTTGGATGCACAATGGCCGGAGGAAATTACCTCAGTTCAA  5280
M18152   TTAAGTGTTCAATTAAAACTCTTGGATGCACAATGGCCGGAGGAAATTACCTCAGTTCAA  5280
         ************************************************************

S288C    GACGGCTGCCAAGTTACGGATAGAAATGGTAACATTATCTATCAAGGCCTATCAGTTAGA  5316
M18151   GACGGCTGCCAAGTTACGGATAGAAATGGTAACATTATCTATCAAGGCCTATCAGTTAGA  5340
M18152   GACGGCTGCCAAGTTACGGATAGAAATGGTAACATTATCTATCAAGGCCTATCAGTTAGA  5340
         ************************************************************

S288C    ATGGGTATTCATTGGGGCTGCCCAGTTCCAGAGCTTGATTTAGTGACTCAAAGAATGGAC  5376
M18151   ATGGGTATTCATTGGGGCTGCCCAGTTCCAGAGCTTGATTTAGTGACTCAAAGAATGGAC  5400
M18152   ATGGGTATTCATTGGGGCTGCCCAGTTCCAGAGCTTGATTTAGTGACTCAAAGAATGGAC  5400
         ************************************************************

S288C    TATTTGGGGCCGATGGTCAATAAGGCAGCAAGGGTCCAGGGCGTCGCTGACGGTGGTCAG  5436
M18151   TATTTGGGGCCGATGGTCAATAAGGCAGCAAGGGTCCAGGGCGTCGCTGACGGTGGTCAG  5460
M18152   TATTTGGGGCCGATGGTCAATAAGGCAGCAAGGGTCCAGGGCGTCGCTGACGGTGGTCAG  5460
         ************************************************************

S288C    ATTGCAATGAGTAGTGATTTTTACTCTGAATTCAACAAGATAATGAAGTATCATGAGCGA  5496
M18151   ATTGCAATGAGTAGTGATTTTTACTCTGAATTCAACAAGATAATGAAGTATCATGAGCGA  5520
M18152   ATTGCAATGAGTAGTGATTTTTACTCTGAATTCAACAAGATAATGAAGTATCATGAACGA  5520
         ********************************************************  ***

S288C    GTAGTGAAGGGCAAGGAATCTCTCAAGGAAGTTTATGGTGAAGAAATTATCGGAGAGGTT  5556
M18151   GTAGTGAAGGGCAAGGAATCTCTCAAGGAAGTTTATGGTGAAGAAATTATCGGAGAGGTT  5580
M18152   GTAGTGAAGGGCAAGGAATCTCTCAAGGAAGTTTATGGTGAAGAAATTATCGGAGAGGTT  5580
         ************************************************************

S288C    CTTGAAAGAGAAATTGCCATGCTGGAAAGTATTGGTTGGGCATTTTTTGACTTTGGCGAG  5616
M18151   CTTGAAAGAGAAATTGCCATGCTGGAAAGTATTGGTTGGGCATTTTTTGACTTTGGCGAG  5640
M18152   CTTGAAAGAGAAATTGCCATGCTGGAAAGTATTGGTTGGGCATTTTTTGACTTTGGCGAG  5640
         ************************************************************

S288C    CATAAGCTAAAGGGACTCGAAACCAAAGAACTCGTTACTATTGCGTATCCTAAGATTCTT  5676
M18151   CATAAGCTAAAGGGACTCGAAACCAAAGAACTCGTTACTATTGCGTATCCTAAGATTCTT  5700
M18152   CATAAGCTAAAGGGACTCGAAACCAAAGAACTCGTTACTATTGCGTATCCTAAGATTCTT  5700
         ************************************************************

S288C    GCTTCCAGACACGAATTTGCATCTGAAGATGAGCAGTCAAAATTAATCAATGAAACGATG  5736
M18151   GCTTCCAGACACGAATTTGCATCTGAAGATGAGCAGTCAAAATTAATCAATGAAACGATG  5760
M18152   GCTTCCAGACACGAATTTGCATCTGAAGATGAGCAGTCAAAATTAATCAATGAAACGATG  5760
         ************************************************************
```

FIG. 6A (cont.)

```
S288C    TTGTTTCGTTTAAGAGTCATTTCAAACAGACTGGAATCTATAATGTCAGCTTTAAGCGGC  5796
M18151   TTGTTTCGTTTAAGAGTCATTTCAAACAGACTGGAATCTATAATGTCAGCTTTAAGCGGC  5820
M18152   TTGTTTCATTTAAGAGTCATTTCAAACAGACTGGAATCTATAATGTCAGCTTTAAGCGGC  5820
         ******* ****************************************************

S288C    GGATTTATTGAACTAGACTCTCGGACGGAGGGAAGTTATATTAAATTTAACCCTAAAGTT  5856
M18151   GGATTTATTGAACTAGACTCTCGGACGGAGGGAAGTTATATTAAATTTAACCCTAAAGTT  5880
M18152   GGATTTATTGAACTAGACTCTCGGACGGAGGGAAGTTATATTAAATTTAACCCTAAAGTT  5880
         ************************************************************

S288C    GAAAATGGTATTATGCAATCGATTTCTGAGAAGGATGCGTTGTTATTTTTTGATCATGTA  5916
M18151   GAAAATGGTATTATGCAATCGATTTCTGAGAAGGATGCGTTGTTATTTTTTGATCATGTA  5940
M18152   GAAAATGGTATTATGCAATCGATTTCTGAGAAGGATGCGTTGTTATTTTTTGATCATGTA  5940
         ************************************************************

S288C    ATTACTAGAATCGAATCCAGTGTGGCATTATTACATTTACGACAACAGAGGTGTTCAGGA  5976
M18151   ATTACTAGAATCGAATCCAGTGTGGCATTATTACATTTACGACAACAGAGGTGTTCAGGA  6000
M18152   ATTACTAGAATCGAATCCAGTGTGGCATTATTACATTTACGACAACAGAGGTGTTCAGGA  6000
         ************************************************************

S288C    CTGGAAATTTGCAGAAACGATAAAACATCTGCTCGAAGCAATATTTTCAATGTTGTTGAC  6036
M18151   CTGGAAATTTGCAGAAACGATAAAACATCTGCTCGAAGCAATATTTTCAATGTTGTTGAC  6060
M18152   CTGGAAATTTGCAGAAACGATAAAACATCTGCTCGAAGCAATATTTTCAATGTTGTTGAC  6060
         ************************************************************

S288C    GAACTTTTACAAATGGTTAAGAACGCAAAGGATTTATCAACTTGA  6081 (SEQ ID NO : 1)
M18151   GAACTTTTACAAATGGTTAAGAACGCAAAGGATTTATCAACTTGA  6105 (SEQ ID NO : 5)
M18152   GAACTTTTACAAATGGTTAAGAACGCAAAGGATTTATCAACTTGA  6105 (SEQ ID NO : 7)
         *********************************************
```

FIG. 6A (cont.)

```
S288C    MSSKPDTGSEISGPQRQEEQEQQIEQSSPTEANDRSIHDEVPKVKKRHEQNSGHKSRRNS    60
M18151   MSSKPDTGSEISGPQRQEEQEQQIEQSSPTEANDRSIHDEVPKVKKRHEQNSGHKSRRNS    60
M18152   MSSKPDTGSEISGPQRQEEQEQQIEQSSPTEANDRSIHDEVPKVKKRHEQNSGHKSRRNS    60
         ************************************************************

S288C    AYSYYSPRSLSMTKSRESITPNGMDDVSISNVEHPRPTEPKIKRGPYLLKKTLSSLSMTS    120
M18151   AYSYYSPRSLSMTKSRESITPNGMDDVSISNVEHPRPTEPKIKRGPYLLKKTLSSLSMTS    120
M18152   AYSYYSPRSLSMTKSRESITPNGMDDVSISNVEHPRPTEPKIKRGPYLLKKTLSSLSMTS    120
         ************************************************************

S288C    ANSTHDDNKDHGYALNSSKTHNYTSTHNHHDGHHDHHHVQFFPNRKPSLAETLFKRFSGS    180
M18151   ANSTHDDNKDHGYALNSSKTHNYTSTHNHHDGHHDHHHVQFFPNRKPSLAETLFKRFSGS    180
M18152   ANSTHDDNKDHGYALNSSKTHNYTSTHNHHDGHHDHHHVQFFPNRKPSLAETLFKRFSGS    180
         ************************************************************

S288C    NSHDGNKSGKESKVANLSLSTVNPAPANRKPSKDSTLSNHLADNVPSTLRRKVSSLVRGS    240
M18151   NSHDGNKSGKESKVANLSLSTVNPAPANRKPSKDSTLSNHLADNVPSTLRRKVSSLVRGS    240
M18152   NSHDGNKSGKESKVANLSLSTVNPAPANRKPSKDSTLSNHLADNVPSTLRRKVSSLVRGS    240
         ************************************************************
                                       ↓
S288C    SVHDINNGIADKQIRPKAVAQSENTLHSSDVPNSKRSHRKSFLLGSTSSSSSRRGSNVSS    300
M18151   SVHDINNGIADKQIRPKTVAQSENTLHSSDVPNSKRSHRKSFLLGSTSSSSSRRGSNVSS    300
M18152   SVHDINNGIADKQIRPKAVAQSENTLHSSDVPNSKRSHRKSFLLGSTSSSSSRRGSNVSS    300
         ****************:*******************************************

S288C    MTNSDSASMATSGSHVLQHNVSNVSPTTKSKDSVNSESADHTNNKSEKVTPEYNENIPEN    360
M18151   MTNSDSASMATSGSHVLQHNVSNVSPTTKSKDSVNSESADHTNNKSEKVTPEYNENIPEN    360
M18152   MTNSDSASMATSGSHVLQHNVSNVSPTTKSKDSVNSESADHTNNKSEKVTPEYNENIPEN    360
         ************************************************************

S288C    SNSDNKREATTPTIETPISCKPSLFRLDTNLEDVTDITKTVPPTAVNSTLNSTHGTETAS    420
M18151   SNSDNKREATTPTIETPISCKPSLFRLDTNLEDVTDITKTVPPTAVNSTLNSTHGTETAS    420
M18152   SNSDNKREATTPTIETPISCKPSLFRLDTNLEDVTDITKTVPPTAVNSTLNSTHGTETAS    420
         ************************************************************

S288C    PKTVIMPEGPRKSVSMADLSVAAAAPNGEFTSTSNDRSQWVAPQSWDVETKRKKTKPKGR    480
M18151   PKTVIMPEGPRKSVSMADLSVAAAAPNGEFTSTSNDRSQWVAPQSWDVETKRKKTKPKGR    480
M18152   PKTVIMPEGPRKSVSMADLSVAAAAPNGEFTSTSNDRSQWVAPQSWDVETKRKKTKPKGR    480
         ************************************************************

S288C    SKSRRSSIDADELDPMSPGPPSKKDS--------RHHHDRKDNESMVTAGDSNSSFVDIC    532
M18151   SKSRRSSIDADELDPMSPGPPSKKDSRHRKNRHSRHHHDRKDNESMVTAGDSNSSFVDIC    540
M18152   SKSRRSSIDADELDPMSPGPPSKKDSRHRKNRHSRHHHDRKDNESMVTAGDSNSSFVDIC    540
         *************************        ***************************

S288C    KENVPNDSKTALDTKSVNRLKSNLAMSPPSIRYAPSNLDGDYDTSSTSSSLPSSSISSED    592
M18151   KENVPNDSKTALDTKSVNRLKSNLAMSPPSIRYAPSNLDGDYDTSSTSSSLPSSSISSED    600
M18152   KENVPNDSKTALDTKSVNRLKSNLAMSPPSIRYAPSNLDGDYDTSSTSSSLPSSSISSED    600
         ************************************************************

S288C    TSSCSDSSSYTNAYMEANREQDNKTPILNKTKSYTKKFTSSSVNMNSPDGAQSSGLLLQD    652
M18151   TSSCSDSSSYTNAYMEANREQDNKTPILNKTKSYTKKFTSSSVNMNSPDGAQSSGLLLQD    660
M18152   TSSCSDSSSYTNAYMEANREQDNKTPILNKTKSYTKKFTSSSVNMNSPDGAQSSGLLLQD    660
         ************************************************************

S288C    EKDDEVECQLEHYYKDFSDLDPKRHYAIRIFNTDDTFTTLSCTPATTVEEIIPALKRKFN    712
M18151   EKDDEVECQLEHYYKDFSDLDPKRHYAIRIFNTDDTFTTLSCTPATTVEEIIPALKRKFN    720
M18152   EKDDEVECQLEHYYKDFSDLDPKRHYAIRIFNTDDTFTTLSCTPATTVEEIIPALKRKFN    720
         ************************************************************
```

FIG. 6B

```
S288C    ITAQGNFQISLKVGKLSKILRPTSKPILIERKLLLLNGYRKSDPLHIMGIEDLSFVFKFL    772
M18151   ITAQGNFQISLKVGKLSKILRPTSKPILIERKLLLLNGYRKSDPLHIMGIEDLSFVFKFL    780
M18152   ITAQGNFQISLKVGKLSKILRPTSKPILIERKLLLLNGYRKSDPLHIMGIEDLSFVFKFL    780
         ************************************************************
                                                          ↓
S288C    FHPVTPSHFTPEQEQRIMRSEFVHVDLRNMDLTTPPIIFYQHTSEIESLDVSNNANIFLP    832
M18151   FHPVTPSHFTPEQEQRIMRSEFVHVDLRNMDLTTPPIIFYQHTSEIESLDVSNNVNIFLP    840
M18152   FHPVTPSHFTPEQEQRIMRSEFVHVDLRNMDLTTPPIIFYQHTSEIESLDVSNNANIFLP    840
         ******************************************************.****
                           ↓
S288C    LEFIESSIKLLSLRMVNIRASKFPSNITKAYKLVSLELQRNFIRKVPNSIMKLSNLTILN    892
M18151   LEFIESSIKLLSLRMVNIRASKFPSNITKAYKLVSLELQRNFIRKVPNSIMKLSNLTILN    900
M18152   LEFIESSIKLLSLRMVNIRASKFPSNITEAYKLVSLELQRNFIRKVPNSIMKLSNLTILN    900
         ****************************:*******************************

S288C    LQCNELESLPAGFVELKNLQLLDLSSNKFMHYPEVINYCTNLLQIDLSYNKIQSLPQSTK    952
M18151   LQCNELESLPAGFVELKNLQLLDLSSNKFMHYPEVINYCTNLLQIDLSYNKIQSLPQSTK    960
M18152   LQCNELESLPAGFVELKNLQLLDLSSNKFMHYPEVINYCTNLLQIDLSYNKIQSLPQSTK    960
         ************************************************************

S288C    YLVKLAKMNLSHNKLNFIGDLSEMTDLRTLNLRYNRISSIKTNASNLQNLFLTDNRISNF    1012
M18151   YLVKLAKMNLSHNKLNFIGDLSEMTNLRTLNLRYNRISSIKTNASNLQNLFLTDNRISNF    1020
M18152   YLVKLAKMNLSHNKLNFIGDLSEMTNLRTLNLRYNRISSIKTNASNLQNLFLTDNRISNF    1020
         *************************:**********************************

S288C    EDTLPKLRALEIQENPITSISFKDFYPKNMTSLTLNKAQLSSIPGELLTKLSFLEKLELN    1072
M18151   EDTLPKLRALEIQENPITSISFKDFYPKNMTSLTLNKAQLSSIPGELLTKLSFLEKLELN    1080
M18152   EDTLPKLRALEIQENPITSISFKDFYPKNMTSLTLNKAQLSSIPGELLTKLSFLEKLELN    1080
         ************************************************************

S288C    QNNLTRLPQEISKLTKLVFLSVARNKLEYIPPELSQLKSLRTLDLHSNNIRDFVDGMENL    1132
M18151   QNNLTRLPQEISKLTKLVFLSVARNKLEYIPPELSQLKSLRTLDLHSNNIRDFVDGMENL    1140
M18152   QNNLTRLPQEISKLTKLVFLSVARNKLEYIPPELSQLKSLRTLDLHSNNIRDFVDGMENL    1140
         ************************************************************

S288C    ELTSLNISSNAFGNSSLENSFYHNMSYGSKLSKSLMFFIAADNQFDDAMWPLFNCFVNLK    1192
M18151   ELTSLNISSNAFGNSSLENSFYHNMSYGSKLSKSLMFFIAADNQFDDAMWPLFNCFVNLK    1200
M18152   ELTSLNISSNAFGNSSLENSFYHNMSYGSKLSKSLMFFIAADNQFDDAMWPLFNCFVNLK    1200
         ************************************************************

S288C    VLNLSYNNFSDVSHMKLESITELYLSGNKLTTLSGDTVLKWSSLKTLMLNSNQMLSLPAE    1252
M18151   VLNLSYNNFSDVSHMKLESITELYLSGNKLTTLSGDTVLKWSSLKTLMLNSNQMLSLPAE    1260
M18152   VLNLSYNNFSDVSHMKLESITELYLSGNKLTTLSGDTVLKWSSLKTLMLNSNQMLSLPAE    1260
         ************************************************************

S288C    LSNLSQLSVFDVGANQLKYNISNYHYDWNWRNNKELKYLNFSGNRRFEIKSFISHDIDAD    1312
M18151   LSNLSQLSVFDVGANQLKYNISNYHYDWNWRNNKELKYLNFSGNRRFEIKSFISHDIDAD    1320
M18152   LSNLSQLSVFDVGANQLKYNISNYHYDWNWRNNKELKYLNFSGNRRFEIKSFISHDIDAD    1320
         ************************************************************

S288C    LSDLTVLPQLKVLGLMDVTLNTTKVPDENVNFRLRTTASIINGMRYGVADTLGQRDYVSS    1372
M18151   LSDLTVLPQLKVLGLMDVTLNTTKVPDENVNFRLRTTASIINGMRYGVADTLGQRDYVSS    1380
M18152   LSDLTVLPQLKVLGLMDVTLNTTKVPDENVNFRLRTTASIINGMRYGVADTLGQRDYVSS    1380
         ************************************************************
                                                              ↓
S288C    RDVTFERFRGNDDECLLCLHDSKNQADYGHNISRIVRDIYDKILIRQLERYGDETDDNI    1432
M18151   RDVTFERFRGNDDECLLCLHDSKNQADYGHNISRIVRDIYDKILIRQLERYGDETDDNI    1440
M18152   RDVTFERFRGNDDECLLCLHDSKNQADYGHNISRIVRDIYDKILIRQLERYGDDTDDNI    1440
         *****************************************************:*****
```

FIG. 6B (cont.)

```
S288C    KTALRFSFLQLNKEINGMLNSVDNGADVANLSYADLLSGACSTVIYIRGKKLFAANLGDC    1492
M18151   KTALRFSFLQLNKEINGMLNSVDNGADVANLSYADLLSGACSTVIYIRGKKLFAANLGDC    1500
M18152   KTALRFSFLQLNKEINGMLNSVDNGADVANLSYADLLSGACSTVIYIRGKKLFAANLGDC    1500
         ************************************************************

S288C    MAILSKNNGDYQTLTKQHLPTKREEYERIRISGGYVNNGKLDGVVDVSRAVGFFDLLPHI    1552
M18151   MAILSKNNGDYQTLTKQHLPTKREEYERIRISGGYVNNGKLDGVVDVSRAVGFFDLLPHI    1560
M18152   MAILSKNNGDYQTLTKQHLPTKREEYERIRISGGYVNNGKLDGVVDVSRAVGFFDLLPHI    1560
         ************************************************************

S288C    HASPDISVVTLTKADEMLIVATHKLWEYMDVDTVCDIARENSTDPLRAAAELKDHAMAYG    1612
M18151   HASPDISVVTLTKADEMLIVATHKLWEYMDVDTVCDIARENSTDPLRAAAELKDHAMAYG    1620
M18152   HASPDISVVTLTKADEMLIVATHKLWEYMDVDTVCDIARENSTDPLRAAAELKDHAMAYG    1620
         ************************************************************

S288C    CTENITILCLALYENIQQNRFTLNKNSLMTRRSTFEDTTLRRLQPEISPPTGNLAMVFT    1672
M18151   CTENITILCLALYENIQQNRFTLNKNSLMTRRSTFEDTTLRRLQPEISPPTGNLAMVFT    1680
M18152   CTENITILCLALYENIQQNRFTLNKNSLMTRRSTFEDTTLRRLQPEISPPTGNLAMVFT    1680
         ************************************************************

S288C    DIKSSTFLWELFPNAMRTAIKTHNDIMRRQLRIYGGYEVKTEGDAFMVAFPTPTSGLTWC    1732
M18151   DIKSSTFLWELFPNAMRTAIKTHNDIMRRQLRIYGGYEVKTEGDAFMVAFPTPTSGLTWC    1740
M18152   DIKSSTFLWELFPNAMRTAIKTHNDIMRRQLRIYGGYEVKTEGDAFMVAFPTPTSGLTWC    1740
         ************************************************************

S288C    LSVQLKLLDAQWPEEITSVQDGCQVTDRNGNIIYQGLSVRMGIHWGCPVPELDLVTQRMD    1792
M18151   LSVQLKLLDAQWPEEITSVQDGCQVTDRNGNIIYQGLSVRMGIHWGCPVPELDLVTQRMD    1800
M18152   LSVQLKLLDAQWPEEITSVQDGCQVTDRNGNIIYQGLSVRMGIHWGCPVPELDLVTQRMD    1800
         ************************************************************

S288C    YLGPMVNKAARVQGVADGGQIAMSSDFYSEFNKIMKYHERVVKGKESLKEVYGEEIIGEV    1852
M18151   YLGPMVNKAARVQGVADGGQIAMSSDFYSEFNKIMKYHERVVKGKESLKEVYGEEIIGEV    1860
M18152   YLGPMVNKAARVQGVADGGQIAMSSDFYSEFNKIMKYHERVVKGKESLKEVYGEEIIGEV    1860
         ************************************************************

S288C    LEREIAMLESIGWAFFDFGEHKLKGLETKELVTIAYPKILASRHEFASEDEQSKLINETM    1912
M18151   LEREIAMLESIGWAFFDFGEHKLKGLETKELVTIAYPKILASRHEFASEDEQSKLINETM    1920
M18152   LEREIAMLESIGWAFFDFGEHKLKGLETKELVTIAYPKILASRHEFASEDEQSKLINETM    1920
         ************************************************************

S288C    LFRLRVISNRLESIMSALSGGFIELDSRTEGSYIKFNPKVENGIMQSISEKDALLFFDHV    1972
M18151   LFRLRVISNRLESIMSALSGGFIELDSRTEGSYIKFNPKVENGIMQSISEKDALLFFDHV    1980
M18152   LFHLRVISNRLESIMSALSGGFIELDSRTEGSYIKFNPKVENGIMQSISEKDALLFFDHV    1980
         **:*********************************************************

S288C    ITRIESSVALLHLRQQRCSGLEICRNDKTSARSNIFNVVDELLQMVKNAKDLST    2026  (SEQ ID NO:2)
M18151   ITRIESSVALLHLRQQRCSGLEICRNDKTSARSNIFNVVDELLQMVKNAKDLST    2034  (SEQ ID NO:6)
M18152   ITRIESSVALLHLRQQRCSGLEICRNDKTSARSNIFNVVDELLQMVKNAKDLST    2034  (SEQ ID NO:8)
         ******************************************************
```

FIG. 6B (cont.)

OPTIMIZATION OF YEAST HOST CELLS FOR THE PRODUCTION OF HETEROLOGOUS PROTEINS

CROSS-REFERENCE TO RELATED APPLICATIONS, SEQUENCE LISTING AND BIOLOGICAL DEPOSITS

The present application claims priority from U.S. provisional application 62/733,471 filed Sep. 19, 2018 and herewith incorporated in its entirety. The present application also includes the following biological deposits, all deposited at American Type Culture Collection (ATCC®) located at 10801 University Boulevard, Manassas, VA, U.S.A. 20110, an International Depositary Authority, under Budapest Treaty on Jul. 25, 2018: PTA-125175 (for strain M18151), PTA-125176 (for strain M18152) and PTA-125177 (for strain M18195) which are included herewith in their entirety and a sequence listing entitled 55729550-31PCT Sequence listing as filed which is also incorporated in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127 419USPC_SEQUENCE_LISTING.txt. The text file is 85.5 KB, was created on Mar. 17, 2021, and is being submitted electronically via EFS-Web.

TECHNOLOGICAL FIELD

The present disclosure relates to yeast host cell capable of producing high yield of an heterologous protein having increased biological activity.

BACKGROUND

Heterologous proteins are often produced, on an industrial scale, in filamentous fungi or in bacteria using a fed batch fermentation. Filamentous fungi require growth on a complex (and usually highly viscous) medium and long fermentation times. Filamentous fungi are limited in expressing extracellular (secreted) heterologous proteins. *Bacillus* is often used as a bacterial host cell for the production of heterologous proteins. While *Bacillus* usually require a simple medium (that may be supplement with an additional protein source), they provide short fermentation times and offer interesting yields when the heterologous enzyme is produced in a recombinant fashion). *Bacillus* could be used to express heterologous proteins intracellulariy as well as extracellularly.

It would be highly desirable to be provided with a host cell which could be used not only in a fed batch fermentation but in a continuous fermentation. It would also be desirable to be provided with a host cell capable of using a simple substrate and of generating the heterologous protein during a short fermentation. It would further be desirable to be provided with a host cell capable of producing not only a high yield of the heterologous protein but also heterologous proteins having high biological and/or specific activity.

BRIEF SUMMARY

The present disclosure concerns a recombinant yeast host cell capable of expressing a higher amount per cell of an heterologous protein.

In a first aspect, the present disclosure concerns a recombinant yeast host cell for making an increased amount of an heterologous protein. The recombinant yeast host cell has a first heterologous nucleic acid encoding the heterologous protein. The recombinant yeast host cell has an altered intracellular cyclic AMP (cAMP) signaling pathway. The recombinant yeast host cell can be obtained by introducing the first heterologous nucleic acid in an ancestral yeast host cell having the altered intracellular cAMP pathway. The altered intracellular cAMP pathway provides to the ancestral or the recombinant yeast host cell a substantially similar cAMP production in the presence and in the absence of a cAMP stimulus (understood to stimulate intracellular cAMP production in a control yeast cell). In an embodiment, the amount of heterologous protein per cell of the recombinant yeast host cell is increased with respect to a corresponding amount in a control yeast cell. In a further embodiment, the control yeast cell corresponds to biological deposit PTA-125176 or a yeast cell having the characteristics of the biological deposit PTA-125176. In another embodiment, the recombinant yeast host cell expresses a variant protein of the cAMP signaling pathway. In another embodiment, the variant protein is a variant CYR1 protein encoded by a variant CYR1 gene. In yet a further embodiment, the variant CYR1 gene is a native CYR1 gene. In an embodiment, the ancestral yeast host cell is biological deposit PTA-125175 or a yeast cell having the characteristics of the biological deposit PTA-125175. In still another embodiment, the ancestral yeast host cell is biological deposit PTA-125177 or a yeast cell having the characteristics of the biological deposit PTA-125177. In some embodiments, the recombinant yeast host cell comprises a second heterologous nucleic acid molecule comprising a variant CYR1 gene encoding a variant CYR1 protein. In some additional embodiments, the variant CYR1 gene has at least one single nucleotide polymorphism (SNP). For example, the at least one SNP can be G772A when using the numbering of the nucleic acid sequence of SEQ ID NO: 1 or 7, C2480T when using the numbering of the nucleic acid sequence of SEQ ID NO: 1, C2504T when using the numbering of the nucleic acid sequence of SEQ ID NO: 7, G2605A when using the numbering of the nucleic acid sequence of SEQ ID NO: 7; or C4305A when using the numbering of the nucleic acid sequence of SEQ ID NO: 7. In some embodiments, the variant CYR1 protein has at least one of the following variations: A258T when using the numbering of the amino acid sequence of SEQ ID NO: 2 or 8; A827V when using the numbering of the amino acid sequence of SEQ ID NO: 2; A835V when using the numbering of the amino acid sequence of SEQ ID NO: 8; E869K when using the numbering of the amino acid sequence of SEQ ID NO: 8; or D1435E when using the numbering of the amino acid sequence of SEQ ID NO: 8. In yet another embodiment, the recombinant yeast host cell exhibits polyploidy in at least one chromosome. For example, polyploidy can comprise triploidy in at least one first chromosome and tetraploidy in at least one second chromosome. In another embodiment, the heterologous protein is an heterologous enzyme such as, for example, a maltogenic alpha-amylase, an alpha-amylase, an oxidoreductase, a transferase, an hydrolase, a lyase, an isomerase, a phosphatase, a ligase, a glucoamylase, a fungal amylase, a phytase or a glucose oxidase. In an embodiment, the recombinant yeast host cell is from the genus *Saccharomyces*. In some additional embodiments, the recombinant yeast host cell is from the species *Saccharomyces cerevisiae*.

According to a second aspect, the present disclosure concerns a method of making a recombinant yeast host cell as defined herein. The method comprises a) selecting an ancestral yeast host cell having the altered intracellular cAMP pathway, wherein the altered intracellular cAMP pathway provides to the ancestral yeast host cell a substantially similar cAMP production in the presence and in the absence of a cAMP stimulus. The method also comprises b) introducing a first heterologous nucleic acid molecule encoding the heterologous protein in the selected ancestral yeast host cell to obtain the recombinant yeast host cell. In an embodiment, step a) comprises comparing the amount of the heterologous protein expressed in the ancestral yeast host cell to a corresponding amount in a control yeast cell and selecting the ancestral yeast host cell if the amount of the heterologous protein is higher than the corresponding amount in the control yeast cell. In an embodiment, control yeast cell corresponds to biological deposit PTA-125176 or a yeast cell having the characteristics of the biological deposit PTA-125176. In another embodiment, step a) comprises determining if the ancestral yeast host cell expresses a variant protein of the cAMP signaling pathway. In an embodiment, variant protein of the cAMP signaling pathway is a variant CYR1 gene encoding a variant CYR1 protein. In some embodiments, the variant CYR1 gene is a native CYR1 gene. In an embodiment, the selected ancestral yeast host cell is biological deposit PTA-125175 or a yeast cell having the characteristics of the biological deposit PTA-125175. In another embodiment, the selected ancestral yeast host cell is biological deposit PTA-125177 or a yeast cell having the characteristics of the biological deposit PTA-125177. In still another embodiment, the variant CYR1 gene is encoded by a second heterologous nucleic acid molecule. In some embodiments, the method further comprises introducing a second heterologous nucleic acid molecule encoding the variant CYR1 gene in the ancestral yeast host cell (prior to or after the selection step a). In an embodiment, the variant CYR1 gene has at least one single nucleotide polymorphism (SNP).

In yet another embodiment, the at least one SNP is G772A when using the numbering of the nucleic acid sequence of SEQ ID NO: 1 or 7; C2480T when using the numbering of the nucleic acid sequence of SEQ ID NO: 1; C2504T when using the numbering of the nucleic acid sequence of SEQ ID NO: 7; G2605A when using the numbering of the nucleic acid sequence of SEQ ID NO: 7; or C4305A when using the numbering of the nucleic acid sequence of SEQ ID NO: 7. In still another embodiment, the variant CYR1 protein has at least one of the following variations: A258T when using the numbering of the amino acid sequence of SEQ ID NO: 2 or 8; A827V when using the numbering of the amino acid sequence of SEQ ID NO: 2; A835V when using the numbering of the amino acid sequence of SEQ ID NO: 8; E869K when using the numbering of the amino acid sequence of SEQ ID NO: 8; or D1435E when using the numbering of the amino acid sequence of SEQ ID NO: 8. In a further embodiment, the method further comprises determining if the ancestral yeast host cell exhibits polyploidy. In yet another embodiment, polyploidy is determined to be present if the ancestral yeast host cell exhibits triploidy in at least one first chromosome and tetraploidy in at least one second chromosome and selecting the ancestral yeast host cell exhibiting triploidy in the at least one first chromosome and tetraploidy in the at least one second chromosome. In a further embodiment, the heterologous protein is an heterologous enzyme such as, for example, at least one of a maltogenic alpha-amylase, an alpha-amylase, an oxidoreductase, a transferase, an hydrolase, a lyase, an isomerase, a phosphatase, a ligase, a glucoamylase, a fungal amylase, a phytase or a glucose oxidase. In an embodiment, the ancestral yeast host cell is from the genus *Saccharomyces*. In yet another embodiment, the ancestral yeast host cell is from the species *Saccharomyces cerevisiae*.

In a third aspect, the present disclosure concerns a recombinant yeast host cell obtainable or obtained by the method described herein.

In a fourth aspect, the present disclosure concerns a process for making a yeast product.

The process comprises culturing the recombinant yeast host cell defined herein to obtain a cultured recombinant yeast host cell; and formulating the cultured yeast host cell into the yeast product. In some embodiments, the formulating step comprises lysing the cultured yeast host cell to obtain a lysed yeast product; and optionally drying the lysed recombinant yeast host cell to obtain a lysed and dried yeast product. In an embodiment, the yeast product is an autolysate, a yeast cell wall or a yeast extract. In a further embodiment, the yeast product is a substantially purified heterologous protein for example an heterologous enzyme.

In a fifth aspect, the present disclosure concerns a yeast product obtainable or obtained by the process described herein. In an embodiment, the yeast product can be a substantially purified heterologous protein such as, for example, an heterologous enzyme.

BRIEF DESCRIPTION OF THE DRAWINGS

Having thus generally described the nature of the invention, reference will now be made to the accompanying drawings, showing by way of illustration, a preferred embodiment thereof, and in which:

FIGS. 3A and C are representative of images taken after overnight growth in yeast extract peptone with 4% glucose whereas FIGS. 3B and D are representative images taken after one hour of transfer to fresh yeast extract peptone with 4% glucose. All images taken at 400× magnification.

FIGS. 6A and 6B provides the alignment of (FIG. 6A) the nucleic acid sequence of the CYR1 gene expressed in *S. cerevisiae* strain S288C (SEQ ID NO: 1), strain M18151 (SEQ ID NO: 5) and strain M18152 (SEQ ID NO: 7) and of (FIG. 6B) the amino acid sequence of the CYR1 protein expressed in *S. cerevisiae* strain S288C (SEQ ID NO: 2), strain M18151 (SEQ ID NO: 6) and strain M18152 (SEQ ID NO: 8).

DETAILED DESCRIPTION

Figure 1:
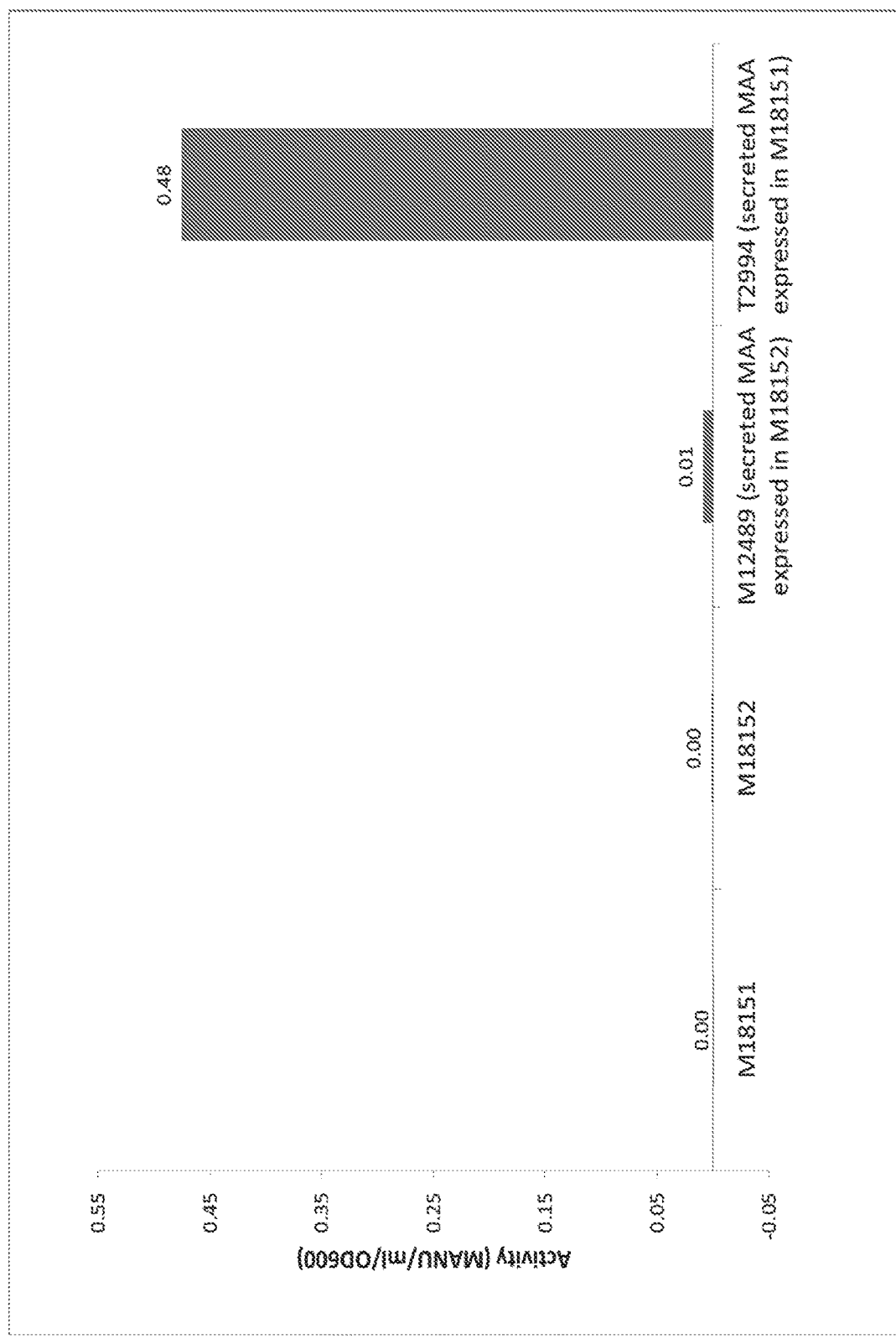
FIG. 1 illustrates the secreted maltogenic amylase activity (MAU/ml/OD$_{600}$) in culture supernatant of wild-type baking strains (M18151 or M18152) or strains expressing a maltogenic alpha-amylase from equivalent genetic cassettes in either M18151 or M18152 baking strain backgrounds. Results are shown as maltogenic alpha-amylase activity per milliliter and normalized to cell density (OD$_{600}$) for each strain tested.

The present disclosure concerns yeast host cell engineered to express an heterologous protein (such as an heterologous enzyme) and which is capable of achieving increased yield and/or biological activity of the expressed heterologous protein. As used in the context of the present disclosure, a recombinant yeast host cell exhibiting "an increased yield in the level of expressed heterologous protein" refers to a recombinant yeast host cell capable of producing a higher amount of the heterologous protein per cell when compared to the level of the heterologous protein expressed in a corresponding control host cell modified in the same manner (with respect to the expression of the heterologous protein) as the recombinant yeast host cell. As used in the context of the present disclosure, a recombinant yeast host cell exhibiting "an increased biological activity of the expressed heterologous protein" refers to a recombinant yeast host cell capable of exhibiting increased biological activity for the heterologous protein per cell when compared to the level of biological activity observed in a corresponding control host cell modified in the same manner (with respect to the expression of the heterologous protein) as the recombinant yeast host cell. When the heterologous protein is an enzyme, a recombinant yeast host cell exhibiting "an increased biological activity of the expressed heterologous protein" refers to a recombinant yeast host cell capable of producing an increased total activity per cell for the heterologous enzyme when compared to the level of total activity observed in a corresponding control host cell modified in the same manner (with respect to the expression of the heterologous protein) as the recombinant yeast host cell.

The recombinant host cell of the present disclosure is a yeast as it can be used in both fed batch and continuous fermentations for enzyme production, can use a simple substrate and, as shown herein, can achieve high yield (increase amount of heterologous protein per cell) and/or biological activity of the heterologous protein. One embodiment of the recombinant yeast host cell is from the species *Saccharomyces cerevisiae*. *S. cerevisiae* is not typically an industrial producer of heterologous proteins such as enzymes because it often lags behind other hosts in terms of the enzyme titer that can be achieved. *S. cerevisiae*, however, has many attributes that would make it a desirable host for production of enzymes for food, feed, and other industries, if it were able to produce high levels of enzyme. *S. cerevisiae* is a generally recognized as safe (GRAS) organism with a long history of safe use in food.

Fractions of yeast or whole yeast cells, live or inactivated, are often used as ingredients and processing aids, so any carryover from enzyme production and purification will be considered safe. Yeasts have also long been used as a model organism for scientific research, so it is an extremely well-studied organism and has an extensive depth of genetic tools, and now genomics resources, available. *S. cerevisiae* is able to grow on inexpensive substrates (e.g., molasses) and has a relatively short fermentation time, making contamination control easier.

Recombinant Yeast Host Cell

The present disclosure concerns recombinant yeast host cells that have been genetically engineered. The genetic modification(s) is(are) aimed at increasing the expression of a specific targeted gene (which is considered heterologous to the yeast host cell) and can be made in one or multiple (e.g., 1, 2, 3, 4, 5, 6, 7, 8 or more) genetic locations. In the context of the present disclosure, when recombinant yeast cell is qualified as being "genetically engineered", it is understood to mean that it has been manipulated to add at least one or more heterologous or exogenous nucleic acid residue. In some embodiments, the one or more nucleic acid residues that are added can be derived from an heterologous cell or the recombinant host cell itself. In the latter scenario, the nucleic acid residue(s) is (are) added at one or more genomic location which is different than the native genomic location. The genetic manipulations did not occur in nature and are the results of in vitro manipulations of the yeast.

The genetic modifications in the recombinant yeast host cell of the present disclosure comprise, consist essentially of or consist of a first genetic modification for expression of the an heterologous polypeptide and, optionally a second genetic modification for altering the intracellular cyclic AMP signaling pathway. In the context of the present disclosure, the expression "the genetic modifications in the recombinant yeast host consist essentially of a first genetic modification for expression of the heterologous polypeptide and a second genetic modification for altering the intracellular cyclic AMP signaling pathway" refers to the fact that the recombinant yeast host cell can include other genetic modifications which are unrelated to the heterologous protein production or the alteration of the intracellular cyclic AMP signaling pathway.

When expressed in recombinant yeast host cells, the heterologous proteins described herein are encoded on one or more heterologous nucleic acid molecules. The term "heterologous" when used in reference to a nucleic acid molecule (such as a promoter, a terminator or a coding sequence) or a protein refers to a nucleic acid molecule or a protein that is not natively found in the recombinant host cell. "Heterologous" also includes a native coding region/promoter/terminator, or portion thereof, that was removed from the source organism and subsequently reintroduced into the source organism in a form that is different from the corresponding native gene, e.g., not in its natural location in the organism's genome. The heterologous nucleic acid molecule is purposively introduced into the recombinant host cell.

For example, a heterologous element could be derived from a different strain of host cell, or from an organism of a different taxonomic group (e.g., different kingdom, phylum, class, order, family genus, or species, or any subgroup within one of these classifications).

The heterologous nucleic acid molecule present in the recombinant host cell can be integrated in the host cell's genome. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies (e.g., 2, 3, 4, 5, 6, 7, 8 or even more copies) in the yeast host cell's genome. Alternatively, the heterologous nucleic acid molecule can be independently replicating from the yeast's genome. In such embodiment, the nucleic acid molecule can be stable and self-replicating.

Suitable yeast host cells that can be used in the context of the present disclosure can be, for example, from the genus *Saccharomyces, Kluyveromyces, Arxula, Debaryomyces, Candida, Pichia, Phaffia, Schizosaccharomyces, Hansenula, Kloeckera, Schwanniomyces, Torula* or *Yarrowia*. Suitable yeast species can include, for example, *S. cerevisiae, S. bulderi, S. bametti, S. exiguus, S. uvarum, S. diastaticus, C. utilis, K. lactis, K. marxianus* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiments, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genus *Thraustochytrium* or *Schizochytrium*). In an embodiment, the recombinant yeast host cell is from the genus *Saccharomyces* and, in some embodiments, from the species *Saccharomyces cerevisiae*.

The recombinant yeast host cells of the present disclosure include a first heterologous nucleic acid molecule intended to allow the expression (e.g., encoding) of one or more heterologous proteins. In an embodiment, the heterologous protein is an heterologous enzyme. In the context of the present application, the heterologous enzyme can be, without limitation, an heterologous oxidoreductase, an heterologous transferase, an heterologous hydrolase, an heterologous lyase, an heterologous isomerase, an heterologous phosphatase and/or an heterologous ligase.

As used in the context of the present disclosure, the expression "oxidoreductase" (also referred to as an oxidase, E.C. 1) refers to a protein having enzymatic activity and capable of catalyzing the transfer of electrons from one molecule (the reductant or the electron donor) to another (the oxidant or the electron acceptor). In an embodiment, the oxidoreductase is a hexose oxidase (E.C. 1.1.3.5), for example, the hexose oxidase can be a glucose oxidase (E.C. 1.1.3.4). In some embodiments, oxidases (such as glucose oxidases) can improve dough machinability. In an embodiment, the one or more oxidoreductases can be a glucose oxidase from *Aspergillus niger*. Oxidoreductases can be used in fermentation processes for making biofuels, distilling products, wine, beer and yeast-leavened bakery products.

Oxidoreductases can be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "transferase" (E.C. 2) refers to a protein having enzymatic activity and capable of catalyzing the transfer of specific functional groups (e.g., a methyl or glycosyl group for example) from one molecule (called the donor) to another (called the acceptor). For example, the transferases can be acyltransferases (E.C. 2.3 such as transglutaminases (E.C. 2.3.2.13) for example) or glycosyltransferases (E.C. 2.4 such as amylomaltases (E.C. 2.4.1.3) for example). A transglutaminase can be used in baking goods to improve dough strength.

As used in the context of the present disclosure, the expression "lyase" (E.C. 4) refers to a protein having enzymatic activity and capable of catalyzing the elimination of various chemical bonds by means other than hydrolysis (e.g., a "substitution" reaction) and oxidation.

For example, the lyase can be a malolactic enzyme (EC 4.1.1.101), Acetolactate decarboxylase (or, alpha-acetolactate decarboxylase, EC 4.1.1.5) and/or a pectate lyase (E.C. 4.2.2.2). Lyases can be used in fermentation processes for making biofuels, distilling products, wine, beer and yeast-leavened bakery products. Lyases can also be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "isomerase" (E.C. 5) refers to a protein having enzymatic activity and capable of catalyzing the conversion a molecule from one isomer to another. For example, the isomerase can be a glucose isomerase (E.C. 5.1.3) or xylose isomerase (EC 5.1.3.5). Isomerases can be used in fermentation processes for making biofuels, distilling products, wine, beer and yeast-leavened bakery products.

Isomerases can also be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "ligase" (E.C. 6) refers to a protein having enzymatic activity and capable of catalyzing the joining of two molecules by forming a new chemical bond. For example, the ligase can be an urea amidolyase (E.C. EC 6.3.4.6). Ligases can be used in fermentation processes for making biofuels, distilling products, wine, beer and yeast-leavened bakery products. Ligases can also be used for making food and beverages (e.g., non-yeast-leavened (chemically-leavened) bakery products), feed or other industrial products (e.g., detergents, textiles, leather, pulp and paper, oil and gas and/or biopolymers).

As used in the context of the present disclosure, the expression "hydrolase" (E.C. 3) refers to a protein having enzymatic activity and capable of catalyzing the hydrolysis of a chemical bound. For example, the hydrolase can be an esterase (E.C. 3.1 for example lipase, phospholipase A1 and/or phospholipase A2), can cleaved C—N non-peptide bonds (E.C. 3.5 for example an asparaginase), can be a glycosylase (E.C. 3.2 for example an amylase (E.C. 3.2.1.1), a glucanase, a glycosidase (E.C. 3.2.1), a cellulase (E.C. 3.2.1.4)), a pectinase and/or a lactase (E.C. 3.2.1.108)), a protease (E.C. 3.4 for example a bacterial protease, a plant protease or a fungal protease). When the hydrolase is an amylase, it can be, for example, a fungal alpha amylase, a bacterial alpha amylase, a maltogenic alpha amylase, a maltotetrahydrolase, a plant (e.g., barley) alpha or beta amylase and/or a glucoamylase.

When the hydrolase is a glycosidase, it can be, for example, a beta glucosidase. When the hydrolase is a cellulase, it can be, for example, a cellulase, an hemicellulase and/or a xylanase.

As used herein, the expression "phosphatase" refers to a protein having enzymatic activity and capable, in the presence of water, of catalyzing the cleavage of a phosphoric acid monoester into a phosphate ion and an alcohol. An embodiment of a phosphatase is a phytase, a protein having enzymatic activity and capable of catalyzing the hydrolysis of phytic acid (myo-inositol hexakisphosphate) into inorganic phosphorus. There are four distinct classes of phytase: histidine acid phosphatases (HAPS), β-propeller phytases, purple acid phosphatases and protein tyrosine phosphatase-like phytases (PTP-like phytases).

Phytic acid has six phosphate groups that may be released by phytases at different rates and in different order. Phytases hydrolyze phosphates from phytic acid in a stepwise manner, yielding products that again become substrates for further hydrolysis. Phytases have been grouped based on the first phosphate position of phytic acid that is hydrolyzed: are 3-phytase (EC 3.1.3.8), 4-phytase (EC 3.1.3.26) and 5-phytase (EC 3.1.3.72). In an embodiment, the phytase is derived from a bacterial species, such as, for example, a *Citrobacter* sp. or an *Escherichia* sp. In a specific embodiment, the heterologous phytase is derived from a *Citrobacter* sp., such as for example *Citrobacter braakii*, a variant thereof or a fragment thereof. In another embodiment, the heterologous phytase is derived from an *Escherichia* sp., such as, for example, *Escherichia coli*, a variant thereof or a fragment thereof.

As used herein, the expression "amylolytic enzyme" refers to a class of enzymes capable of hydrolyzing starch or hydrolyzed starch. Amylolytic enzymes include, but are not limited to alpha-amylases (EC 3.2.1.1, sometimes referred to fungal alpha-amylase, see below), maltogenic amylase (EC 3.2.1.133), glucoamylase (EC 3.2.1.3), glucan 1,4-alpha-maltotetraohydrolase (EC 3.2.1.60), pullulanase (EC 3.2.1.41), iso-amylase (EC 3.2.1.68) and amylomaltase (EC 2.4.1.25). In an embodiment, the one or more amylolytic enzymes can be an alpha-amylase from *Aspergillus oryzae*, a maltogenic alpha-amylase from *Geobacillus stearothermophilus* (and have, for example, the amino acid sequence of SEQ ID NO: 3, a variant thereof or a fragment thereof), an alpha-amylase from *Pyrococcus furiosus* (and have, for example, the amino acid sequence of SEQ ID NO: 4), a glucoamylase from *Saccharomycopsis fibuligera*, a glucan 1,4-alpha-maltotetraohydrolase from *Pseudomonas*, a pullulanase from *Bacillus naganoensis*, a pullulanase from *Bacillus acidopullulyticus*, an iso-amylase from *Pseudomonas amyloderamosa* and/or amylomaltase from *Thermus thermophilus*.

As used herein, the expression "cellulase/hemi-cellulase" refers to a class of enzymes capable of hydrolyzing, respectively, cellulose or hemi-cellulose. Cellulases/hemi-cellulases include, but are not limited to a cellulase (E.C. 3.2.1.4) and an endoB(1,4)D-xylanase (E.C. 3.2.1.8). In an embodiment, the one or more cellulase/hemi-cellulase can be a cellulase from *Penicillium funiculosum* and/or an endoB(1, 4)D-xylanase from *Rasamsonia emersonii*.

As used herein, the expression "lipase" refers to a class of enzymes capable of hydrolyzing lipids. In an embodiment, the one or more lipase can be a triacylglycerol lipase from *Thermomyces lanuginosis*, a phospholipase A2 from *Sus scrofa*, a phospholipase A2 from *Streptomyces vialaceoruber* and/or a phospholipase A2 from *Aspergillus oryzea*.

As used in the present disclosure, the term "maltogenic amylase" refers to a polypeptide capable of hydrolyzing starch or hydrolyzed starch into maltose. Maltogenic amylases include, but are not limited to fungal alpha-amylases (derived, for example, from *Aspergillus* sp. (e.g., *A. niger, A. kawachi* and *A. oryzae*); *Trichoderma* sp. (e.g., *T. reesie*), *Rhisopus* sp., *Mucor* sp. and *Penicillium* sp.), acid stable fungal amylase (derived, for example, from *Aspergillus niger*), A-amylases (derived, for example, from plant (wheat, barley, rye, shorgum, soy, sweet potato, rice) and/or microorganisms (*Bacillus cereus, Bacillus polymixa, Bacillus megaterium, Arabidopsis thaliana*), maltogenic amylases (E.C.3.2.1.133) (derived, for example, from microorganisms such as *Bacillus subtilis, Geobacillus stearothermophilus, Bacillus thermoalkalophilus, Lactobacillus gasser, Thermus* sp.). In a specific embodiment, the recombinant yeast host cells of the present disclosure include an heterologous nucleic acid molecule coding for the heterologous maltogenic amylase derived from *Geobacillus stearothermophilus*.

The heterologous protein can be a variant of a known/native protein. A variant comprises at least one amino acid difference when compared to the amino acid sequence of the native/know protein. As used herein, a variant refers to alterations in the amino acid sequence that do not adversely affect the biological functions of the heterologous protein. A substitution, insertion or deletion is said to adversely affect the protein when the altered sequence prevents or disrupts a biological function associated with the heterologous protein.

For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the heterologous protein. The protein variants have at least 50%, 55%, 60%, 65%, 70%, 75%, 80%, 85%, 90%, 95%, 96%, 97%, 98% or 99% identity to the heterologous protein described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant heterologous protein described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. A "variant" of the heterologous protein can be a conservative variant or an allelic variant.

The heterologous protein can be a fragment of a known/native protein or fragment of a variant of a known/native protein. In an embodiment, the fragment corresponds to the known/native protein to which the signal peptide sequence has been removed. In some embodiments, heterologous protein "fragments" have at least at least 100, 200, 300, 400, 500, 600, 700, 800, 900 or more consecutive amino acids of the heterologous protein. A fragment comprises at least one less amino acid residue when compared to the amino acid sequence of the known/native heterologous protein and still possess the enzymatic activity of the full-length heterologous protein. In an embodiment, the fragment corresponds to the amino acid sequence of the protein lacking the signal peptide. In some embodiments, fragments of the heterologous protein can be employed for producing the corresponding full-length heterologous by peptide synthesis. Therefore, the fragments can be employed as intermediates for producing the full-length proteins.

In the recombinant yeast host cell of the present disclosure, the heterologous protein can be physically associated or not with the recombinant yeast host cell. In an embodiment, the heterologous protein is secreted and, upon its secretion, becomes physically dissociated from the recombinant yeast host cell.

In another embodiment, the heterologous protein remains associated with the recombinant yeast host cell (e.g., is "cell-associated") once it has been expressed. In such embodiment, the heterologous protein can be expressed inside the recombinant yeast host cell (intracellulariy). In such embodiment, the heterologous protein does not need to be associated to the recombinant yeast host cell's wall. Men the heterologous protein is intended to be expressed intracellularly, its signal sequence, if present in the native sequence, can be deleted to allow intracellular expression.

In another embodiment of a cell-associated heterologous protein, it can be secreted upon expression, but when it is, it must remain physically associated with the recombinant yeast host cell. In an embodiment, at least one portion (usually at least one terminus) of the heterologous protein is bound, covalently, non-covalently and/or electrostatically for example, to cell wall (and in some embodiments to the cytoplasmic membrane). For example, the heterologous protein can be modified to bear one or more transmembrane domains, to have one or more lipid modifications (myristoylation, palmitoylation, farnesylation and/or prenylation), to interact with one or more membrane-associated protein and/or to interactions with the cellular lipid rafts. While the heterologous protein may not be directly bound to the cell membrane or cell wall (e.g., such as when binding occurs via a tethering moiety), the protein is nonetheless considered a "cell-associated" heterologous protein according to the present disclosure.

In some additional cell association embodiments, the heterologous protein can be expressed to be located at and associated to the cell wall of the recombinant yeast host cell. In some embodiments, the heterologous protein is expressed to be located at and associated to the external surface of the cell wall of the host cell. Recombinant yeast host cells all have a cell wall (which includes a cytoplasmic membrane) defining the intracellular (e.g., internally-facing the nucleus) and extracellular (e.g., externally-facing) environments. The heterologous protein can be located at (and in some embodiments, physically associated to) the external face of the recombinant yeast host's cell wall and, in further embodiments, to the external face of the recombinant yeast host's cytoplasmic membrane. In the context of the present disclosure, the expression "associated to the external face of the cell wal/cytoplasmic membrane of the recombinant yeast host cell" refers to the ability of the heterologous protein to physically integrate (in a covalent or non-covalent fashion), at least in part, in the cell wall (and in some embodiments in the cytoplasmic membrane) of the recombinant yeast host cell.

The physical integration can be attributed to the presence of, for example, a transmembrane domain on the heterologous protein, a domain capable of interacting with a cytoplasmic membrane protein on the heterologous protein, a post-translational modification made to the heterologous protein (e.g., lipidation), etc.

Some heterologous proteins have the intrinsic ability to locate at and associate to the cell wall of a recombinant yeast host cell (e.g., being cell-associated). One example of an heterologous protein having the intrinsic ability of being cell-associated is the maltogenic alpha-amylase of *Geobacillus stearothermophilus* expressed in *S. cerevisiae* in the absence of a tethering moiety and clearly show that this heterologous protein is intrinsically "cell-associated" and exhibits enzymatic activity (e.g., maltogenic alpha-amylase activity).

However, in some circumstances, it may be warranted to increase or provide cell association to some heterologous proteins because they exhibit insufficient intrinsic cell association or simply lack intrinsic cell association. In such embodiment, it is possible to provide the heterologous protein as a chimeric construct by combining it with a tethering amino acid moiety which will provide or increase attachment to the cell wall of the recombinant yeast host cell. In such embodiment, the chimeric heterologous protein will be considered "tethered". It is preferred that the amino acid tethering moiety of the chimeric protein be neutral with respect to the biological activity of the heterologous protein, e.g., does not interfere with the biological activity (such as, for example, the enzymatic activity) of the heterologous protein. In some embodiments, the association of the amino acid tethering moiety with the heterologous protein can increase the biological activity of the heterologous protein (when compared to the non-tethered, "free" form). The tethering moiety can be a transmembrane domain found on another protein and allow the chimeric protein to have a transmembrane domain. Alternatively, the tethering moiety can be modified post-translation to include a glycosylphosphatidylinositol (GPI) anchor and allow the chimeric protein to have a GPI anchor. The tethering moiety may be directly associated with the heterologous protein or be indirectly associated by the use of a linker. Exemplary tethering moieties have been disclosed in PCT/IB2018/051671 (incorporate herewith in its entirety) and can be used to provide the heterologous protein of the present disclosure in a tethered form.

The recombinant yeast host cell can be derived from an ancestral yeast host cell having an altered intracellular cyclic AMP signaling pathway or of exhibiting a constitutive elevated level of intracellular cyclic AMP (cAMP). The intracellular production of cAMP is usually inducible in response to glucose addition to glucose starved yeast or yeast grown on non-fermentable carbon sources, as well as repletion of nitrogen or phosphorus when cells are starved for each nutrient. Modulation in the levels of intracellular cAMP mediates downstream signaling.

As it is shown in the Examples below, yeast cells having an altered intracellular cAMP signaling pathway can be used as host cells to produce more biologically active heterologous proteins per cell. The recombinant yeast host cell of the present disclosure exhibits an "altered" intracellular cyclic AMP signaling pathway (or a "constitutive" elevated intracellular cAMP levels) when their levels of intracellular cAMP are not substantially modified in the presence of a cAMP stimulus known to stimulate intracellular cAMP production in a control cell (e.g., glucose, nitrogen and/or phosphorus when the yeast host cell is placed in glucose, nitrogen and/or phosphorus depletion conditions). The recombinant yeast host cell of the present disclosure is understood to exhibit an altered intracellular cAMP signaling pathway (or a constitutive "elevated" intracellular cAMP levels) when compared to a control yeast host cell placed in a corresponding condition. For example, when placed in the presence and absence of a cAMP stimulus (glucose, nitrogen or phosphorus), the selected ancestral or the recombinant yeast host cell of the present disclosure does not exhibit in a substantial difference in intracellular cAMP levels in contrast to the control yeast cell (which would exhibit increased intracellular cAMP levels in the presence of the cAMP stimulus).

In an embodiment, the ability of the recombinant yeast host cell to exhibit an altered intracellular cAMP signaling (or a constitutive intracellular cAMP level) can be native to the recombinant yeast host cell (e.g., it can be the results of a wild-type mutation that was not genetically introduced into the recombinant yeast host cell). Exemplary recombinant yeast host cell having such native ability include, but are not limited to biological deposit PTA-125175 (also referred to herewith to M18151, deposited on at the American Type Culture Collection on Jul. 25, 2018), biological deposit PTA-125177 (also referred to herewith as M18195, deposited on at the American Type Culture Collection on Jul. 25, 2018) or a yeast cell having the characteristics of the biological deposit PTA-125175 or PTA-125177.

In another embodiment, the ability of the recombinant yeast host cell to exhibit an altered intracellular cAMP signaling (or a constitutive intracellular cAMP level) is provided by the genetic modification of the recombinant yeast host cell (that can be introduced prior to or after the first genetic modification). For example, it is possible to inactivate a protein involved in the breakdown of cAMP (for example by removing one or more nucleic acid residues in a gene coding for a protein involved in the catabolism of cAMP). This could also be achieved by inactivating or downregulating the protein repressors of the cAMP pathway (IRA1 and/or IRA2 for example) and/or expressing constitutively active forms of RAS1 and/or RAS2.

Alternatively or in combination, it is possible to introduce of at least a second heterologous nucleic acid molecule which can encode a non-coding sequence (such as a promoter) or a coding sequence (such as one encoding a protein) which provides such activity. Exemplary embodiments of the second heterologous nucleic acid molecule include those of the promoters of gene encoding proteins capable of producing intracellular cAMP, such as, for example, an adenylate cyclase, those encoding proteins capable of producing intracellular cAMP, such as, for example, an adenylate cyclase as well as those encoding proteins regulating the activity of proteins capable of producing intracellular cAMP, such as, for example, an adenylate cyclase. In an embodiment, the second heterologous nucleic acid molecule can be, for example, a constitutive promoter intended to regulate the expression of a native or heterologous protein capable of producing intracellular cAMP, such as, for example, an adenylate cyclase. In another embodiment, the second heterologous nucleic acid molecule can be, for example, an heterologous protein capable of producing intracellular cAMP, such as, for example, an adenylate cyclase.

In yeasts, and specifically in *Saccharomyces cerevisiae*, the adenylate cyclase protein is encoded by the CYR1 gene. The ancestral yeast host cell can have a native CYR1 gene which is a variant CYR1 gene. Alternatively or in combination, the recombinant yeast host cell can have or be genetically modified to bear a variant CYR1 gene encoding a CYR1 protein which is constitutively expressed. The recombinant yeast host cell can further be modified to inactive or remove the gene(s) encoding the native adenylate cyclase. In still another example, the second nucleic acid molecule can include a gene encoding a protein capable of increasing the activity of adenylate cyclase and/or decreasing the activity of an inhibitor of adenylate cyclase.

In embodiments in which the recombinant yeast host cell bears a variant CYR1 gene encoding a variant CYR1 protein allowing the constitutive elevated expression of intracellular cAMP. For example, the variant CYR1 gene can include one or more genetic modifications (e.g., insertion, addition and/or modification of at least one nucleic acid residue) when compared to the wild-type CYR1 gene either located in its non-coding and/or coding sequence. The genetic modification can be, for example, a single polymorphic nucleotide (SNP) in the variant CYR1 gene. The genetic modification can lead to the presence of one or more variations (e.g., insertion, addition and/or modification of at least one amino acid residue) in the amino acid sequence of the variant CYR1 protein. The at least one variations may be located in the leucine rich repeats region of the protein (and in some embodiments altering its ability to bind to the Ras protein) and/or in the phosphatase region of the protein (and in some embodiments, altering its ability to remove phosphate moieties from its substrate).

In embodiments in which the wild-type (reference) CYR1 gene has the nucleic acid sequence of SEQ ID NO: 1, the variant CYR1 gene can include one or more SNP at the following corresponding positions: 772 or 2480. In some embodiments, the variant CYR1 gene can include the following two or more SNPs at positions corresponding to 772 and 2480. For example, the variant CYR1 gene can have, at a position corresponding to position 772 of SEQ ID NO: 1 another nucleic acid base than G (A for example). In another example, the variant CYR1 gene can have, at a position corresponding to position 2480 of SEQ ID NO: 1, another nucleic acid base than C (T for example). In some embodiments, the variant CYR1 gene can have, at a position corresponding to position 772 of SEQ ID NO: 1, another nucleic acid base than G (A for example) and, at a position corresponding to position 2480 of SEQ ID NO: 1, another nucleic acid base than C (T for example). In some embodiments, the variant CYR1 gene can have the nucleic acid sequence of SEQ ID NO: 5.

In embodiments in which the wild-type (reference) CYR1 gene has the nucleic acid sequence of SEQ ID NO: 7, the variant CYR1 gene can include one or more SNP at positions corresponding to 772, 2504, 2605 or 4305. In some embodiments, the variant CYR1 gene can include two or more SNPs at the positions corresponding to 772, 2504, 2605 and/or 4305. In additional embodiments, the variant CYR1 gene can include three or more SNPs at the positions corresponding to positions 772, 2504, 2605 and/or 4305. In some further embodiments, the variant CYR1 gene can include four or more SNPs at the following positions: 772, 2504, 2605 and 4305. For example, the variant CYR1 gene can have, at a position corresponding to position 772 of SEQ ID NO: 7, another nucleic acid base than G (A for example). In another example, the variant CYR1 gene can have, at a position corresponding to position 2504 of SEQ ID NO: 7, another nucleic acid base than C (T for example). In still another example, the variant CYR1 gene can have, at a position corresponding to position 2605 of SEQ ID NO: 7, a nucleic acid based other than G (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example) and at a position corresponding to position 2504 of SEQ ID NO: 7, another nucleic acid base than C (T for example). In an embodiment, the variant CYR1 gene can have, at a position corresponding to position 772 of SEQ ID NO: 7, another nucleic acid base than G (A for example) and at a position corresponding to position 2605 of SEQ ID NO: 7, a nucleic acid based other than G (A for example). In an embodiment, the variant CYR1 gene can have, at a position corresponding to position 772 of SEQ ID NO: 7, another nucleic acid base than G (A for example) and at a position corresponding to position 4305 of SEQ ID NO: 7, another nucleic acid base than C (A for example). In an embodiment, the variant CYR1 gene can have, at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example) and at a position corresponding to position 4305 of SEQ ID NO: 7, another nucleic acid base than C (A for example). In still another embodiment, the variant CYR1 gene can have, at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In some embodiments, the variant CYR1 gene can have the nucleic acid sequence of SEQ ID NO: 5.

In embodiments in which the wild-type (reference) CYR1 protein has the amino acid sequence of SEQ ID NO: 2, the variant CYR1 protein can include one or more variations at the following corresponding positions: 258 and 827. In some embodiments, the variant CYR1 protein includes at least two variations at the following corresponding positions: 258 and/or 827. In an example, the variant CYR1 protein could have, at a position corresponding to position 258 of SEQ ID NO: 1, an amino acid residue which is not an alanine residue (a threonine residue for example). In another example, the variant CYR1 protein could have, at a position corresponding to position 835 of SEQ ID NO: 2, an amino acid residue different than an alanine residue (a valine residue for example). In an embodiment, the variant CYR1 protein could have, at a position corresponding to position 258 of SEQ ID NO: 1, an amino acid residue which is not an alanine residue (a threonine residue for example) and at a position corresponding to position 835 of SEQ ID NO: 2, an amino acid residue different than an alanine residue (a valine residue for example). In another embodiment, the variant CYR1 protein can have the amino acid sequence of SEQ ID NO: 6.

In embodiments in which the wild-type (reference) CYR1 protein has the amino acid sequence of SEQ ID NO: 8, the variant CYR1 protein can include one or more variations at the following corresponding positions: 258 835, 869 and/or 1435. In some embodiments, the variant CYR1 protein includes at least two variations at the following corresponding positions: 258 835, 869 and/or 1435. In some additional embodiments, the variant CYR1 protein includes at least three variations at the following positions: 258, 835, 869 and/or 1435. In still further embodiments, the variant CYR1 protein includes at least four variations at the following positions: 258, 835, 869 and 1435. In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example). In a further example, the variant CYR1 protein could have, at position 869 of SEQ ID NO: 8, an amino acid residue which is not a glutamic acid residue (a lysine residue for example). In yet another example, the variant CYR1 protein could have, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example) and at position 835 of SEQ ID NO: 8, an amino acid residue which is not an alanine residue (a valine residue for example). In an example, the variant CYR1 protein could have, at position 258 of SEQ ID NO: 8, an amino acid residue which is not an alanine residue (a threonine residue for example) and at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example) and, at position 1435 of SEQ ID NO: 8, an amino acid residue which is different from an aspartic acid residue (a glutamic acid residue for example). In another example, the variant CYR1 protein could have, at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example), at position 869 of SEQ ID NO: 8, an amino acid residue which is not a glutamic acid residue (a lysine residue for example) and, at position 1435 of SEQ ID NO: 8, an amino acid residue which is different from an aspartic acid residue (a glutamic acid residue for example). In another embodiment, the variant CYR1 protein can have the amino acid sequence of SEQ ID NO: 6.

Optionally, the recombinant yeast host cell can exhibit polyploidy in at least one of its chromosomes. In some embodiments, the recombinant yeast host cell exhibits polyploidy (e.g., triploidy or tetraploidy) in at least one, two, three, four, five, six, seven, eight, nine, ten, eleven, twelve, thirteen, fourteen, fifteen or sixteen chromosomes. In some embodiments, the recombinant yeast host cell exhibits trip-loidy in at least one, two, three, four, five, six, seven, eight, nine, ten, eleven, twelve, thirteen, fourteen, fifteen or sixteen chromosomes.

Alternatively or in combination, the recombinant yeast host cell exhibits tetraploidy in at least one, two, three, four, five, six, seven, eight, nine, ten, eleven, twelve, thirteen, fourteen, fifteen or sixteen chromosomes. In some specific embodiments, the recombinant yeast host cell has a majority of triploid chromosomes. In some further specific embodiments, the recombinant yeast host cell does not have a single haploid or diploid chromosome. In some additional specific embodiments, the recombinant yeast host cell has two tetraploid chromosomes with the remainder of chromosomes triploid.

Method for Making Recombinant Yeast Host Cell

The present disclosure also provides a method for making the recombinant yeast host cell of the present disclosure. The method broadly comprises two steps: a first one in which an ancestral yeast host cell is selected and a second in which the selected ancestral yeast host cell is modified by introducing a first heterologous nucleic acid molecule (coding for the expression of the heterologous protein) to provide the recombinant yeast host cell. The steps of the method can be performed in any order. The selection step can be performed after the introduction step. The introduction step can be performed after the selection step.

In the selection step, an ancestral yeast host cell is chosen if it is shown to exhibit an altered intracellular cAMP signaling (or a constitutive intracellular cAMP level). This can be done, for example, by determining the intracellular level of cAMP in the ancestral yeast host cell in different conditions (in the presence and in the absence of glucose and/or in the presence or absence of nitrogen) to assess if the intracellular level of cAMP is increased or not or if it is constitutive. If the cAMP signaling is altered, the strain is not expected to exhibit an increase in cAMP levels in the presence or the absence of a cAMP stimulus (glucose, nitrogen and/or phosphorus). This can also be done, for example, by comparing the intracellular level of cAMP in the ancestral yeast host cell and in a control host cell in a control condition (e.g., in the presence of glucose and/or the absence of nitrogen or in the absence of glucose and/or in the presence of nitrogen). In such embodiment, the ancestral yeast host cell can be selected on the basis that its intracellular level cAMP is higher than the intracellular level of cAMP of the control yeast host cell. In some embodiments, the control yeast host cell corresponds to biological deposit PTA-125176 or a yeast cell having the characteristics of the biological deposit PTA-125176.

Since the presence of a constitutive and elevated intracellular cAMP level is associated with increased yield and/or increased biological activity of the heterologous protein per cell, the ancestral yeast host cell can be selected based on the fact that it produces a higher amount or a higher biological activity associated with the heterologous protein per cell. The selection can be based, for example, on a comparison with an amount/biological activity of the heterologous protein expressed by a control yeast cell. In some embodiments, the control yeast host cell corresponds to biological deposit PTA-125176 or a yeast cell having the characteristics of the biological deposit PTA-125176.

Since, in some embodiments, the nucleic acid sequence of the CYR1 is indicative of an altered intracellular cAMP signaling (or a constitutive intracellular cAMP level), the selection can be made by determining the nucleic acid sequence (e.g., sequencing) of the CYR1 gene or determining the amino acid sequence of the CYR1 protein expressed in the ancestral host cell. For example, the ancestral host cell can be selected based on the fact that it bears a variant CYR1 gene/natively expresses a variant CYR1 protein which includes one or more genetic modifications (e.g., insertion, addition and/or modification of at least one nucleic acid residue) when compared to the wild-type CYR1 gene either located in its non-coding and/or coding sequence. The genetic modification can be, for example, a single polymorphic nucleotide (SNP) in the CYR1 gene. The genetic modification can lead to the presence of one or more variations (e.g., insertion, addition and/or modification of at least one amino acid residue) in the amino acid sequence of the variant CYR1 protein. The at least one variations may be located in the leucine rich repeats region of the protein (and in some embodiments altering its ability to bind to the Ras protein) and/or in the phosphatase region of the protein (and in some embodiments, altering its ability to remove phosphate moieties from its substrate).

In embodiments in which the wild-type (reference) CYR1 gene has the nucleic acid sequence of SEQ ID NO: 1, the variant CYR1 gene can include one or more SNP at the following corresponding positions: 772 or 2480. In some embodiments, the variant CYR1 gene can include the following two or more SNPs at positions corresponding to 772 and 2480. For example, the variant CYR1 gene can have, at a position corresponding to position 772 of SEQ ID NO: 1 another nucleic acid base than G (A for example). In another example, the variant CYR1 gene can have, at a position corresponding to position 2480 of SEQ ID NO: 1, another nucleic acid base than C (T for example). In some embodiments, the variant CYR1 gene can have, at a position corresponding to position 772 of SEQ ID NO: 1, another nucleic acid base than G (A for example) and, at a position corresponding to position 2480 of SEQ ID NO: 1, another nucleic acid base than C (T for example). In some embodiments, the variant CYR1 gene can have the nucleic acid sequence of SEQ ID NO: 5.

In embodiments in which the wild-type (reference) CYR1 gene has the nucleic acid sequence of SEQ ID NO: 7, the variant CYR1 gene can include one or more SNP at positions corresponding to 772, 2504, 2605 or 4305. In some embodiments, the variant CYR1 gene can include two or more SNPs at the positions corresponding to 772, 2504, 2605 and/or 4305. In additional embodiments, the variant CYR1 gene can include three or more SNPs at the positions corresponding to positions 772, 2504, 2605 and/or 4305. In some further embodiments, the variant CYR1 gene can include four or more SNPs at the following positions: 772, 2504, 2605 and 4305. For example, the variant CYR1 gene can have, at a position corresponding to position 772 of SEQ ID NO: 7, another nucleic acid base than G (A for example). In another example, the variant CYR1 gene can have, at a position corresponding to position 2504 of SEQ ID NO: 7, another nucleic acid base than C (T for example). In still another example, the variant CYR1 gene can have, at a position corresponding to position 2605 of SEQ ID NO: 7, a nucleic acid based other than G (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example) and at a position corresponding to position 2504 of SEQ ID NO: 7, another nucleic acid base than C (T for example). In an embodiment, the variant CYR1 gene can have, at a position corresponding to position 772 of SEQ ID NO: 7, another nucleic acid base than G (A for example) and at a position corresponding to position 2605 of SEQ ID NO: 7, a nucleic acid based other than G (A for example). In an embodiment, the variant CYR1 gene can have, at a position corresponding to position 772 of SEQ ID NO: 7, another nucleic acid base than G (A for example) and at a position corresponding to position 4305 of SEQ ID NO: 7, another nucleic acid base than C (A for example). In an embodiment, the variant CYR1 gene can have, at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example) and at a position corresponding to position 4305 of SEQ ID NO: 7, another nucleic acid base than C (A for example). In still another embodiment, the variant CYR1 gene can have, at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example) and at a position corresponding to position 2605 of SEQ ID NO: 7, a nucleic acid based other than G (A for example). In an embodiment, the variant CYR1 gene can have, at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2605 of SEQ ID NO: 7, a nucleic acid based other than G (A for example) and at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In yet a further example, the variant CYR1 gene can have, at a position corresponding to position 4305 of SEQ ID NO: 7, another nucleic acid base than C (A for example). In an embodiment, the variant CYR1 gene can have, at a position corresponding to position 772 of SEQ ID NO: 7, another nucleic acid base than G (A for example), at a position corresponding to position 2504 of SEQ ID NO: 7, another nucleic acid base than C (T for example), at a position corresponding to position 2605 of SEQ ID NO: 7, a nucleic acid based other than G (A for example) and at a position corresponding to position 4305 of SEQ ID NO: 7, another nucleic acid base than C (A for example). In some embodiments, the variant CYR1 gene can have the nucleic acid sequence of SEQ ID NO: 5.

In embodiments in which the wild-type (reference) CYR1 protein has the amino acid sequence of SEQ ID NO: 2, the variant CYR1 protein can include one or more variations at the following corresponding positions: 258 and 827. In some embodiments, the variant CYR1 protein includes at least two variations at the following corresponding positions: 258 and/or 827. In an example, the variant CYR1 protein could have, at a position corresponding to position 258 of SEQ ID NO: 1, an amino acid residue which is not an alanine residue (a threonine residue for example). In another example, the variant CYR1 protein could have, at a position corresponding to position 835 of SEQ ID NO: 2, an amino acid residue different than an alanine residue (a valine residue for example). In an embodiment, the variant CYR1 protein could have, at a position corresponding to position 258 of SEQ ID NO: 1, an amino acid residue which is not an alanine residue (a threonine residue for example) and at a position corresponding to position 835 of SEQ ID NO: 2, an amino acid residue different than an alanine residue (a valine residue for example). In another embodiment, the variant CYR1 protein can have the amino acid sequence of SEQ ID NO: 6.

In embodiments in which the wild-type (reference) CYR1 protein has the amino acid sequence of SEQ ID NO: 8, the variant CYR1 protein can include one or more variations at the following corresponding positions: 258 835, 869 and/or 1435. In some embodiments, the variant CYR1 protein includes at least two variations at the following corresponding positions: 258 835, 869 and/or 1435. In some additional embodiments, the variant CYR1 protein includes at least three variations at the following positions: 258, 835, 869 and/or 1435. In still further embodiments, the variant CYR1 protein includes at least four variations at the following positions: 258, 835, 869 and 1435. In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example). In a further example, the variant CYR1 protein could have, at position 869 of SEQ ID NO: 8, an amino acid residue which is not a glutamic acid residue (a lysine residue for example). In yet another example, the variant CYR1 protein could have, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example) and at position 835 of SEQ ID NO: 8, an amino acid residue which is not an alanine residue (a valine residue for example). In an example, the variant CYR1 protein could have, at position 258 of SEQ ID NO: 8, an amino acid residue which is not an alanine residue (a threonine residue for example) and at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example) and, at position 1435 of SEQ ID NO: 8, an amino acid residue which is different from an aspartic acid residue (a glutamic acid residue for example). In another example, the variant CYR1 protein could have, at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 869 of SEQ ID NO: 8, an amino acid residue which is not a glutamic acid residue (a lysine residue for example). In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example), at position 835 of SEQ ID NO: 8, an amino acid residue which is not an alanine residue (a valine residue for example) and, at position 1435 of SEQ ID NO: 8, an amino acid residue which is different from an aspartic acid residue (a glutamic acid residue for example). In an example, the variant CYR1 protein could have, at position 258 of SEQ ID NO: 8, an amino acid residue which is not an alanine residue (a threonine residue for example). In another example, the variant CYR1 protein could have, at position 835 of SEQ ID NO: 8, an amino acid residue which is not an alanine residue (a valine residue for example), at position 869 of SEQ ID NO: 8, an amino acid residue which is not a glutamic acid residue (a lysine residue for example) and, at position 1435 of SEQ ID NO: 8, an amino acid residue which is different from an aspartic acid residue (a glutamic acid residue for example). In another embodiment, the variant CYR1 protein can have the amino acid sequence of SEQ ID NO: 8.

In some embodiments, the method includes, prior to the selection step, introducing a second heterologous nucleic acid encoding for a variant CYR1 gene (as disclosed herein) encoding a variant CYR1 protein (as disclosed herein).

In some additional embodiments, it may be beneficial to have a recombinant yeast host cell having at least one or more polyploid chromosome. This can allow, for example, the presence of numerous copies of the gene encoding the heterologous protein and/or the variant CYR1 gene. As such, it may be advisable to select the ancestral host cell based on the status of ploidy of its chromosomes. In some embodiments, the ancestral yeast host cell is selected based on the presence of polyploidy (e.g., triploidy or tetraploidy) in at least one, two, three, four, five, six, seven, eight, nine, ten, eleven, twelve, thirteen, fourteen, fifteen or sixteen chromosomes. In some embodiments, the ancestral yeast host cell is selected based on the presence of triploidy in at least one, two, three, four, five, six, seven, eight, nine, ten, eleven, twelve, thirteen, fourteen, fifteen or sixteen chromosomes. Alternatively or in combination, the ancestral yeast host cell is selected based on the presence of tetraploidy in at least one, two, three, four, five, six, seven, eight, nine, ten, eleven, twelve, thirteen, fourteen, fifteen or sixteen chromosomes. In some specific embodiments, the ancestral yeast host cell is selected based on the presence of a majority of triploid chromosomes. In some further specific embodiments, the ancestral yeast host cell is selected based on the absence of haploid or diploid chromosomes. In some additional specific embodiments, the recombinant yeast host cell has two tetraploid chromosomes with the remainder of chromosomes triploid.

In some embodiments, the method includes, prior or after to the selection step, modifying the ploidy of the ancestral yeast host cell by using mating techniques known in the art. The step of modifying ploidy can occur before or after introducing the optional second heterologous nucleic acid encoding for a variant CYR1 gene (as disclosed herein) encoding a variant CYR1 protein (as disclosed herein).

In order to make the recombinant yeast host cells of the present disclosure, one or more heterologous nucleic acid molecules (also referred to as expression cassettes) are made in vitro and introduced into the yeast host cell in order to allow the recombinant expression of the heterologous protein.

The heterologous nucleic acid molecules of the present disclosure comprise a coding region.

A DNA or RNA "coding region" is a DNA or RNA molecule (preferably a DNA molecule) which is transcribed and/or translated into a protein in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a protein.

The heterologous nucleic acid molecules described herein can comprise non-coding sequence such as transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

In some embodiments, the heterologous nucleic acid molecules of the present disclosure include a promoter as well as a coding sequence for a protein. The heterologous nucleic acid sequence can also include a terminator. In the heterologous nucleic acid molecules of the present disclosure, the promoter and the terminator (when present) are operatively linked to the nucleic acid coding sequence of the protein, e.g., they control the expression and the termination of expression of the nucleic acid sequence of the protein. The heterologous nucleic acid molecules of the present disclosure can also include a nucleic acid coding for a signal peptide, e.g., a short peptide sequence for exporting the heterologous protein outside the host cell. When present, the nucleic acid sequence coding for the signal peptide is directly located upstream and is in frame with the nucleic acid sequence coding for the protein.

In the heterologous nucleic acid molecule described herein, the promoter and the nucleic acid molecule coding for the protein. In the context of the present disclosure, the expressions "operatively linked" or "operatively associated" refers to fact that the promoter is physically associated to the nucleotide acid molecule coding for the protein in a manner that allows, under certain conditions, for expression of the heterologous protein from the nucleic acid molecule. In an embodiment, the promoter can be located upstream (5') of the nucleic acid sequence coding for the heterologous protein. In still another embodiment, the promoter can be located downstream (3) of the nucleic acid sequence coding for the protein. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the protein. The promoters can be located, in view of the nucleic acid molecule coding for the heterologous protein, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be native or heterologous to the nucleic acid molecule encoding the protein. The promoter can be heterologous or derived from a strain being from the same genus or species as the recombinant host cell. In an embodiment, the promoter is derived from the same genus or species of the yeast host cell and the heterologous protein is derived from a different genus than the host cell. The promoter can be a single promoter or a combination of different promoters.

Promoters that can be included in the heterologous nucleic acid molecule of the present disclosure include, without limitation, the promoter of the tdh1 gene (referred to as tdh1p), of the hor7 gene (referred to as hor7p), of the hsp150 gene (referred to as hsp150p), of the hxt7 gene (referred to as hxt7p), of the gpm1 gene (referred to as gpm1p), of the pgk1 gene (referred to as pgk1p) and/or of the stl1 gene (referred to as stl1p).

One or more promoters can be used to allow the expression of each heterologous polypeptides in the recombinant yeast host cell. In the context of the present disclosure, the expression "functional fragment of a promoter" when used in combination to a promoter refers to a shorter nucleic acid sequence than the native promoter which retain the ability to control the expression of the nucleic acid sequence encoding the protein. Usually, functional fragments are either 5' and/or 3' truncation of one or more nucleic acid residue from the native promoter nucleic acid sequence.

In some embodiments, the nucleic acid molecules include one or a combination of terminator sequence(s) to end the translation of the protein. The terminator can be native or heterologous to the nucleic acid sequence encoding the protein. In some embodiments, one or more terminators can be used. In some embodiments, the terminator comprises the terminator derived from is from the dit1 gene (referred to as dit1t), from the idp1 gene (referred to as idp1t), from the gpm1 gene (referred to as gpm1t), from the pma1 gene (referred to as pma1t), from the tdh3 gene (referred to as tdh3t), from the hxt2 gene (referred to as hxt2t), from the adh3 gene (referred to as adh3t), and/or from the ira2 gene (referred to as ira2t). In the context of the present disclosure, the expression "functional variant of a terminator" refers to a nucleic acid sequence that has been substituted in at least one nucleic acid position when compared to the native terminator which retain the ability to end the expression of the nucleic acid sequence coding for the protein. In the context of the present disclosure, the expression "functional fragment of a terminator" refers to a shorter nucleic acid sequence than the native terminator which retain the ability to end the expression of the nucleic acid sequence coding for the protein.

In some embodiments, the heterologous nucleic acid molecules include one or a combination of signal sequence(s) allowing the export of the heterologous protein outside the yeast host cell's wall. The signal sequence can simply be added to the nucleic acid molecule (usually in frame with the sequence encoding the heterologous protein) or replace the signal sequence already present in the heterologous protein. The signal sequence can be native or heterologous to the nucleic acid sequence encoding the heterologous protein. In some embodiments, one or more signal sequences can be used. In some embodiments, the signal sequence is from the the invertase protein, the AGA2 protein or the fungal amylase, including variants and fragments thereof. In the context of the present disclosure, the expression "functional variant of a signal sequence" refers to a nucleic acid sequence that has been substituted in at least one nucleic acid position when compared to the native signal sequence which retain the ability to direct the expression of the heterologous protein outside the cell. In the context of the present disclosure, the expression "functional fragment of a signal sequence" refers to a shorter nucleic acid sequence than the native signal sequence which retain the ability to direct the expression of the protein outside the cell.

In some embodiments in which it is desirable to express the heterologous protein inside the recombinant yeast host cell, the heterologous nucleic acid molecule can exclude the portion coding for the signal sequence which is found in the native gene encoding the protein.

The heterologous nucleic acid molecules can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

The present disclosure also provides nucleic acid molecules for modifying the yeast host cell so as to allow the expression of the heterologous protein(s) and optionally the variant CYR1 protein. The nucleic acid molecule may be DNA (such as complementary DNA, synthetic DNA or genomic DNA) or RNA (which includes synthetic RNA) and can be provided in a single stranded (in either the sense or the antisense strand) or a double stranded form. The contemplated nucleic acid molecules can include alterations in the coding regions, non-coding regions, or both. Examples are nucleic acid molecule variants containing alterations which produce silent substitutions, additions, or deletions, but do not alter the properties or activities of the encoded heterologous proteins, variants or fragments.

In some embodiments, the heterologous nucleic acid molecules which can be introduced into the recombinant host cells are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0.

The heterologous nucleic acid molecules can be introduced in the yeast host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The present disclosure also provides nucleic acid molecules that are hybridizable to the complement nucleic acid molecules encoding the proteins as well as variants or fragments. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min.

For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA: RNA, DNA:RNA, DNA:DNA. For hybrids of greater than 100 nucleotides in length, equations for calculating Tm have been derived. For hybridizations with shorter nucleic acids, i.e., oligonucleotides, the position of mismatches becomes more important, and the length of the oligonucleotide determines its specificity. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

Processes Using the Recombinant Yeast Host Cell

The recombinant yeast host cells of the present disclosure are intended to be used in the processes for making a yeast product. The recombinant yeast host cell of the present disclosure (and, by the same token the yeast product) expresses and comprises the heterologous protein. As used in the context of the present disclosure, a "yeast product" is a composition comprising the recombinant yeast host cell of the present disclosure which has been cultured or a product made by the recombinant yeast host cell of the present disclosure during fermentation and comprising the heterologous protein. In yet another embodiment, the yeast product can be a metabolite produced by the recombinant yeast host cell of the present disclosure, for example, the heterologous protein produced by the recombinant yeast host cell.

The recombinant yeast host cells of the present disclosure can optionally be used in a fermentation process (which can be continuous or fed batch). In an embodiment, the fermentation process can be a relatively long one and the recombinant yeast host cells can be used, for example, in making biofuels, distilling products, wine and beer. In another embodiment, the fermentation process can be a relatively short one and the recombinant yeast host cells can be used, for example, in making yeast-leavened bakery products.

The recombinant yeast host cells of the present disclosure can also be used in a process which does not include a fermentation step. For example, the recombinant yeast host cell can be used for making food and beverages (e.g., non-yeast-leavened (chemically-leavened) bakery products, dairy products, yeast extracts, juices, fat and oils as well as starch), feed or other industrial products (e.g., detergents, textiles, leather, pulp and paper, oil and gas and/or biopolymers).

The yeast products of the present disclosure can be provided in an active form (e.g., liquid, compressed, or fluid-bed dried yeast), in a semi-active form (e.g., liquid, compressed, or fluid-bed dried), in an inactive form (e.g., drum- or spray-dried) as well as a mixture therefore.

For example, the recombinant yeast host cells can be a combination of active and semi-active or inactive forms to provide the ratio and dose of the heterologous protein required for making the yeast composition.

As indicated herein, the present disclosure allows for making a yeast product from the recombinant yeast host cell of the present disclosure. In an embodiment, the yeast product comprises at 0.5, 0.6, 0.7, 0.8, 0.9, 1.0, 1.1, 1.2, 1.3, 1.4, 1.5, 1.6, 1.7, 1.8, 1.9, 2.0, 2.1, 2.1, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 2.2, 4.3, 4.4, 4.5, 4.6, 4.7, 4.8, 4.9, 5.0 weight % or more of the heterologous protein when compared to the total proteins of the yeast product. In another embodiment, the yeast product comprises at least 0.001, 0.002, 0.003, 0.004, 0.005, 0.006, 0.007, 0.008, 0.009, 0.01, 0.011, 0.012, 0.013, 0.014, 0.015, 0.016, 0.017, 0.018, 0.019, 0.02, 0.021, 0.022, 0.023, 0.024, 0.025 g or more of the heterologous protein/g of the total proteins of the recombinant yeast host cell. In yet another embodiment, the yeast product comprises at least 0.05, 0.075, 0.1, 0.2, 0.3, 0.4, 0.5, 0.6, 0.7, 0.8, 0.9, 1.0, 1.1, 1.2, 1.3, 1.4, 1.5 weight % or more of the heterologous protein when compared to the total weight of the recombinant yeast host cell. In still a further embodiment, the yeast product comprises at least 0.0005, 0.0006, 0.0007, 0.0008, 0.0009, 0.001, 0.0011, 0.0012, 0.0013, 0.0014, 0.0015, 0.0016, 0.0017, 0.0018, 0.0019, 0.002, 0.003, 0.004, 0.005, 0.006, 0.007, 0.008, 0.009, 0.01 g or more of the heterologous protein when compared to the dry weight of the recombinant yeast host cell. In an embodiment in which the recombinant yeast host cell is formulated as a yeast cream, the yeast cream comprises at least 45, 46, 47, 48, 49, 50, 50.2, 51, 52, 53, 54, 55 weight % or more of the heterologous protein when compared to the total weight of the yeast cream. In another embodiment in which the heterologous protein is an heterologous enzyme, the present disclosure provides processes as well as yeast products having a specific minimal enzymatic activity and/or a specific range of enzymatic activity. For example, the yeast product can comprise a minimal amount of enzymatic activity which can provide a minimal enzymatic activity/g dry cell weight, which can be, for example, at least 150, 200, 250, 300, 350, 400, 450, 500, 550, 600, 650, 700, 750, 800, 850, 900, 950, 1000, 2000, 3000, 4000, 5000, 6000, 7000, 8000 or more enzymatic activity units/g of dry cell weight. Alternatively or in combination, the yeast product can provide a minimal enzymatic activity/g or mg of the total protein of the recombinant yeast host cell, which can be, for example, 50, 100, 150, 200, 250, 300, 350, 400, 450, 500, 550, 600, 650, 700, 750, 800, 850, 900, 950 or more enzymatic activity units/g or mg of total proteins of the recombinant yeast host cell. In another example, when the heterologous enzyme is an amylase such as a maltogenic amylase, the yeast product can comprises a minimal amount of maltogenic amylase activity (for example, measured as MAU/g of dry weight of the yeast product) which can be, for example, at least about 150, 200, 250, 300, 350, 400, 450, 500, 550, 600, 650, 700, 750, 800, 850, 900, 950, 1000, 2000, 3000, 4000, 5000, 6000, 7000, 8000 or more MAU/g of dry cell weight or 50, 100, 150, 200, 250, 300, 350, 400, 450, 500, 550, 600, 650, 700, 750, 800, 850, 900, 950 or more MAU/g of total proteins of the recombinant yeast host cell. In still another example, when the heterologous enzyme is an amylase such as a glucoamylase, the yeast product can comprise a minimal amount of glucoamylase activity (for example, measured as units of glucoamylase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more glucoamylase units/g of dry cell weight. In a further embodiment, when the heterologous enzyme is an amylase such as an alpha-amylase, the yeast product can comprise a minimal amount of alpha-amylase activity (for example, measured as units of alpha-amylase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more alpha-amylase units/g of dry cell weight. In still another embodiment, when the heterologous enzyme is a phosphatase such as a phytase, the yeast product can comprise a minimal amount of phytase activity (for example, measured as units of phytase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more phytase activity units/g of dry cell weight. In still another example, when the heterologous enzyme is an oxidase such as a glucose oxidase, the yeast product can comprise a minimal amount of glucose oxidase activity (for example, measured as units of glucose oxidase activity/g of dry weight of the yeast product), which can be, for example, 150, 200, 250, 300, 350, 400, 450, 500, 550, 600, 650, 700, 750, 800, 850, 900, 950, 1000, 2000, 3000, 4000, 5000, 6000, 7000, 8000 or more glucose oxidase activity units/g of dry cell weight.

The process for making the yeast product broadly comprises two steps: a first step of culturing (either continuously or in batch) the recombinant yeast host cell and a second step of formulating the yeast product. In the formulating step, the mixture obtained after culture can be modified to provide a yeast product. In an embodiment for providing a yeast product, at least one component of the mixture obtained after culture is removed from the culture medium to provide the yeast product. This component can be, without limitation, water, amino acids, peptides and proteins, nucleic acid residues and nucleic acid molecules, cellular debris, fermentation products, etc. In an embodiment, the formulating step comprises substantially isolating the cultured yeast recombinant host cells (e.g., the biomass) from the components of the culture medium. As used in the context of the present disclosure, the expression "substantially purifying/isolating" refers to the removal of the majority of the components of the culture medium from the cultured recombinant yeast host cells. In some embodiments, "substantially purifying/isolating" refers to concentrating the cultured recombinant yeast host cell to at least 5, 10, 15, 20, 25, 30, 35, 45% or more when compared to the concentration of the recombinant yeast host cell prior to the isolation. In order to provide the yeast product, the cultured recombinant yeast host cells can be centrifuged (and the resulting cellular pellet comprising the cultured recombinant yeast host cells can optionally be washed), filtered and/or dried (optionally using a vacuum-drying technique). The isolated recombinant yeast host cells can then be formulated in a yeast product. The formulation step can, in some embodiments, preserve the viability (at least in part) of the recombinant yeast host cells. As such, the yeast product can be provided in an active or a semi-active form. The yeast product can be provided in a liquid, semi-solid or dry form. In an embodiment, the yeast product can be provided in the form of a cream yeast.

In another embodiment in which the heterologous protein is an heterologous enzyme, the present disclosure provides processes as well as yeast products having a specific minimal enzymatic activity and/or a specific range of enzymatic activity. In addition, when the recombinant yeast host cell expresses a cell-associated heterologous protein, the yeast composition can be concentrated during processing and can remains biologically active to perform its intended function in the yeast products.

In some embodiments, the process for making the yeast product further comprises an additional step of lysing the cultured yeast host cells. The process can include an optional separating step and an optional drying step. For example, the cultured recombinant host cells can be provided, for example, as a 20% cream yeast even though additional embodiments of the cultured recombinant host cells can be provided. Then, the cultured recombinant yeast host cells can be lysed to provide lysed recombinant yeast host cells. For example, the cells can be lysed using autolysis (which can be optionally be performed in the presence of additional exogenous enzymes) or homogenized (for example using a bead-milling technique). In an embodiment, the cultured recombinant yeast host cells can be lysed using autolysis. For example, the cultured recombinant cells can be submitted to a combined heat and pH treatment for a specific amount of time (e.g., 24 h) in order to cause the autolysis of the cultured recombinant yeast host cells to provide the lysed recombinant yeast host cells. The cultured recombinant cells can be submitted to a temperature of between about 40° C. to about 70° C. or between about 50° C. to about 60° C. The cultured recombinant cells can be submitted to a temperature of at least about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C. or 70° C. Alternatively or in combination the cultured recombinant cells can be submitted to a temperature of no more than about 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., 49° C., 48° C., 47° C., 46° C., 45° C., 44° C., 43° C., 42° C., 41° C. or 40° C. In another example, the cultured recombinant cells can be submitted to a pH between about 4.0 and 8.5 or between about 5.0 and 7.5. The cultured recombinant cells can be submitted to a pH of at least about, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4 or 8.5.

Alternatively or in combination, the cultured recombinant cells can be submitted to a pH of no more than 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3., 5.2, 5.1, 5.0, 4.9, 4.8, 4.7, 4.6 or 4.5.

The process for making the yeast product can also include a drying step. The drying step can include, for example, with spray-drying and/or fluid-bed drying. When the yeast product is an autolysate, the process includes directly drying the lysed recombinant yeast host cells after the lysis step without performing an additional separation of the lysed mixture.

To provide additional yeast products, it may be necessary to further separate the components of the lysed recombinant yeast host cells. For example, the cellular wall components (referred to as a "insoluble fraction") of the lysed recombinant yeast host cell may be separated from the other components (referred to as a "soluble fraction") of the lysed recombinant yeast host cells. This separating step can be done, for example, by using centrifugation and/or filtration.

In some embodiments, the insoluble fraction is not submitted to a washing step prior to the subsequent drying step to provide the cell walls as the yeast product or the subsequent drying step to provide the yeast extract as the yeast product. However, the process of the present disclosure can include one or more washing step(s).

In an embodiment of the process, the insoluble fraction can be further separated prior to drying. For example, the components of the soluble fraction having a molecular weight of more than 10 kDa can be separated out of the soluble fraction. This separation can be achieved, for example, by using filtration (and more specifically ultrafiltration). When filtration is used to separate the components, it is possible to filter out (e.g., remove) the components having a molecular weight less than about 10 kDa and retain the components having a molecular weight of more than about 10 kDa. The components of the soluble fraction having a molecular weight of more than 10 kDa can then optionally be dried to provide a retentate as the yeast product. In the process described herein, the yeast product is provided as an inactive form. The yeast product can be provided in a liquid, semi-liquid or dry form.

In an embodiment, the process can also comprise substantially isolating/purifying the heterologous proteins from the yeast product. As used in the context of the present disclosure, the expression "substantially isolating/purifying the heterologous proteins from the lysed recombinant yeast host cells" refers to the removal of the majority of the components of the lysed recombinant yeast host cells from the heterologous proteins and providing same in an isolated/purified form. The heterologous protein can be provided in a liquid form or in a solid (dried) form. As such, the present disclosure provides an isolated heterologous protein obtainable or obtained by the process described herein. In an embodiment, the isolated heterologous protein is produced by a recombinant yeast host cell having and its signal sequenced has been swapped with a signal peptide from a protein naturally expressed in an heterologous organism, such as prokaryotes, a bacteria for example. In an alternative embodiment, a signal sequence has been added to the heterologous protein and this new signal sequence is from protein naturally expressed in prokaryotes such as bacteria.

The present invention will be more readily understood by referring to the following examples which are given to illustrate the invention rather than to limit its scope.

Example I—Heterologous Protein Expression in a M18151 Strain Background

TABLE 1

Genotypes of the *Saccharomyces cerevisiae* strains used in the examples

| Name | Heterologous enzyme Expressed | Original Strain background | Copies of genes coding for heterologous enzyme integrated per chromosome | Promoter | Terminator |
|---|---|---|---|---|---|
| M18151 | Not applicable-wild-type yeast strain used in baking (biological deposit PTA-125175) | | | | |
| M18152 | Not applicable-wild-type yeast strain used in baking (biological deposit PTA-125176) | | | | |
| M2390 | Not applicable-wild type yeast strain used in fuel ethanol | | | | |
| M12489 | Maltogenic alpha amylase (SEQ ID NO: 3) | M18152 | 2 | TDH1p/HOR7p | DIT1t/IDP1t |
| T2994 | Maltogenic alpha amylase (SEQ ID NO: 3) | M18151 | 2 | TDH1p/HOR7p | DIT1t/IDP1t |
| M15532 | Maltogenic alpha amylase (SEQ ID NO: 3) | M18151 | 2 | TDH1p/HOR7p | DIT1t/IDP1t |
| M16147 | *Pyrococcus furiosus* alpha-amylase (SEQ ID NO: 4) | M2390 | 2 | ADH1p/TEF2p | DIT1t/IDP1t |
| M16446 | *Pyrococcus furiosus* alpha-amylase (SEQ ID NO: 4) | M18151 | 2 | ADH1p/TEF2p | DIT1t!IDP1t |
| M16834 | *Pyrococcus furiosus* alpha-amylase (SEQ ID NO: 4) | M18152 | 2 | ADH1p/TEF2p | DIT1t/IDP1t |
| M16440 | *Pyrococcus furiosus* alpha-amylase (SEQ ID NO: 4) | M18195 | 2 | ADH1p/TEF2p | DIT1t/IDP1t |

TABLE 1-continued

Genotypes of the *Saccharomyces cerevisiae* strains used in the examples

| Name | Heterologous enzyme Expressed | Original Strain background | Copies of genes coding for heterologous enzyme integrated per chromosome | Promoter | Terminator |
|---|---|---|---|---|---|
| M16548 | *Pyrococcus furiosus* alpha-amylase (SEQ ID NO: 4) | M15344 | 2 | ADH1p/TEF2p | DIT1t/IDP1t |
| M16452 | *Pyrococcus furiosus* alpha-amylase (SEQ ID NO: 4) | M7101 | 2 | ADH1p/TEF2p | DIT1t/IDP1t |
| M16835 | *Pyrococcus furiosus* alpha-amylase (SEQ ID NO: 4) | M12548 | 2 | ADH1p/TEF2p | DIT1t/IDP1t |

Maltogenic alpha-amylase activity (FIG. 1). Samples were incubated with 2 mg/ml maltodextrin, reducing sugars were reacted with 3,5-dinitrosalicylic acid and measured at 540 nm. Enzyme activity of each samples was compared to a standard curve of known concentrations of a reference commercial maltogenic amylase.

Figure 2:
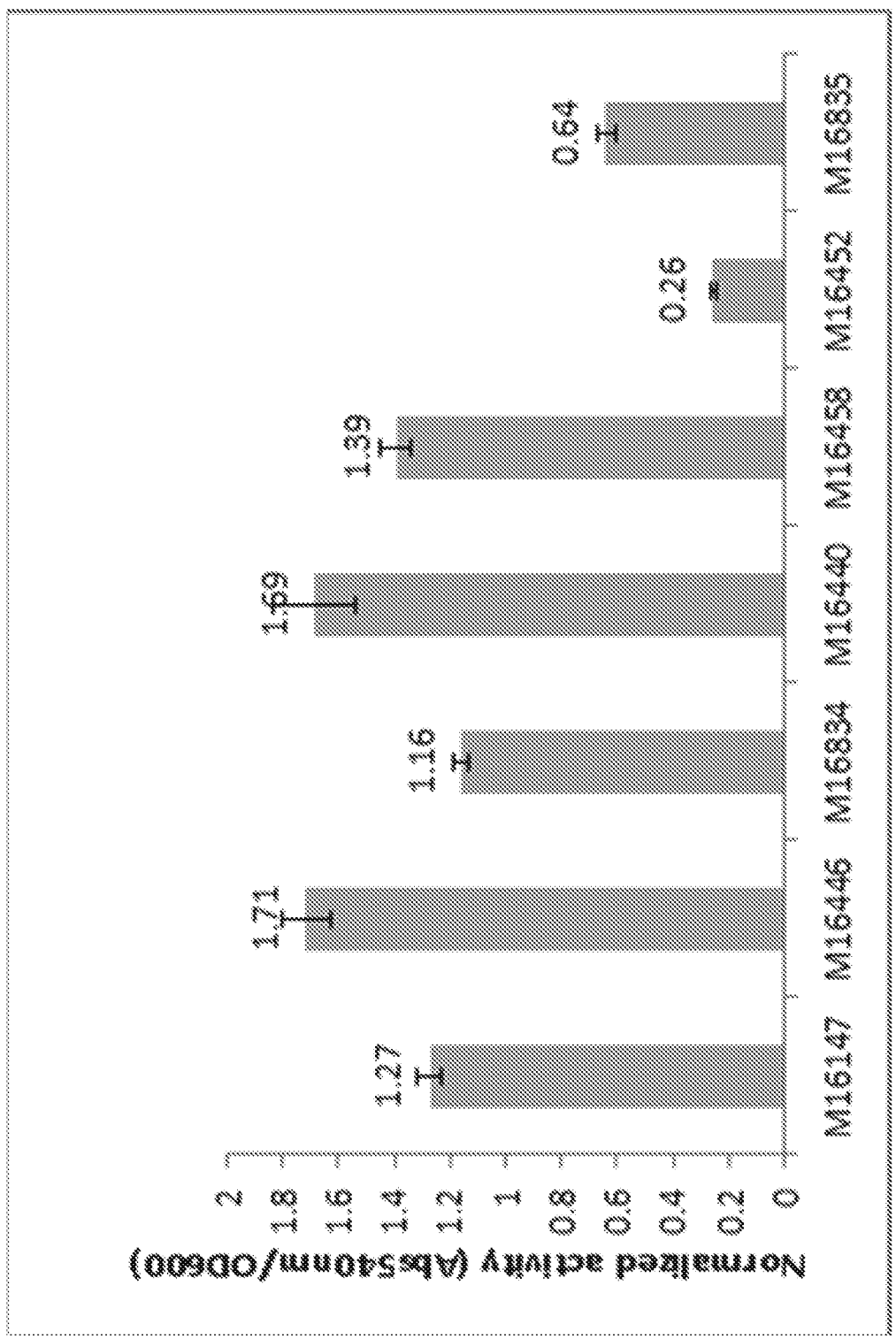
FIG. 2 illustrates the secreted alpha-amylase enzyme activity (measured as absorbance at 540 nm) in the culture supernatant of strains M16147, M16446, M16834, M16440, M16458, M16452, M16835 modified to express a heterologous alpha-amylase. Results are shown as absorbance at 540 nm normalized to cell density (OD$_{600}$) in function of strain tested.

Alpha amylase activity (FIG. 2). The strains were initially grown in 600 μL of $YPD_{40}$, at 35° C. for 48 h in 98-well plates on a shaker at 900 rpm. Alpha-amylase activity was determined by adding 25 μL of washed cells or cell-free supernatant to 100 μL of 1% raw starch with 50 mM sodium acetate buffer (pH 5.2). The assay was treated for 30 min at 85° C. using an Eppendorf Gradient Cycler. The reducing sugars were measured using the Dinitrosalicylic Acid Reagent Solution (DNS) method, using a 2:1 DNS:starch assay ratio and boiled at 100° C. for 5 min. The absorbance was measured at 540 nm.

Cell growth. Cells were grown overnight in 5 mL YPD (10 g/L yeast extract, 20 g/L bacteriological peptone, 40 g/L glucose). One (1) mL of whole culture as harvested and cells were pelleted by centrifugation. Cell-free supernatant was removed and saved for later analysis. Cell pellet was washed once and resuspended in deionized water.

Cream yeast. After the fermentation, the harvested fermentation broth was centrifuged and washed using a laboratory scale separator (from GEA) to prepare yeast cream with a final dry weight close to 20%. To make the inactivated cream yeast, about 600 g of cream yeast was heated on a temperature controlled stirring/hot plate until 75° C. was reached. The cream was kept for 15 minutes at 75° C. and then removed from heat source.

Spray drying. Spray dried samples were prepared by drying with an inlet temperature of 150° C.-200 C. The feeding rate was kept to maintain outlet temperature around 85-90° C.

Fermenter autolysis. 2 000 L-22 000 liters of cream at 18-21% solids was incubated at 55° C. and pH 5.5 with mixing either with an impeller or recirculation. The autolysate (~20% dry weight) was harvested after 30 hours of incubation and separated as described below.

Separation of autolysate. Separations were performed by centrifuging fermenter autolysate in either a disc stack centrifuge with addition of a wash factor of water of 0.6 volumes, or with cross-flow microfiltration through a 0.8 micron membrane and addition of 2 diafiltration volumes of water.

Ultrafiltration. Yeast extract fractions were further concentrated by ultrafiltration with a 10 kDa molecular weight cutoff membrane. The retentate fraction is retained by the membrane and permeate fraction passes through the membrane.

Phadebas MAU enzyme activity assay. Phadebas tablets contain a water insoluble starch substrate and a blue dye, bound to the dye with crosslinks. The substrate is hydrolyzed by maltogenic amylase, releasing blue dye which is soluble. After terminating the reaction and centrifuging, the absorbance of the solution was measured spectrophotometrically and is considered a proxy for enzyme activity. For each sample, one Phadebas tablet was added to 4.9 mL of citrate-phosphate buffer (70 mM disodium hydrogen phosphate, 30 mM citric acid, pH 5.5), incubated in a 60° C. water bath for 5 minutes. Then, 0.1 mL of standard or sample, diluted in citrate-phosphate buffer, was added to the tablet and buffer solution and incubated for 15 minutes in the 60° C. water bath. The reaction was terminated by adding 1 mL of 0.5 M sodium hydroxide solution and mixing. The tubes were centrifuged to remove solids and absorbance of the substrate was measured at 620 nm with a spectrophotometer. Samples (dry or liquid) are compared to a dose curve of standards with known activity. This methods was applied to generate all of the MAU results, except for FIG. 1.

Determination of protein content. Protein content was either estimated as a percentage of total biomass by Kjeldahl method (Table 2) or was measured by Bradford assay with Bio-rad Bradford reagent and a standard curve of bovine gamma globulin dilutions.

Strain M18151 has been used for fermentation in the baking industry and it was found that this strain is an exceptionally good producer of heterologous protein. Several features appear to set this strain apart from many other *S. cerevisiae* isolates. Additionally, when strain M18151 was engineered to produce an heterologous enzyme (e.g., a maltogenic alpha-amylase or an alpha amlyase), it produced higher enzyme activity per cell than other strains engineered with a similar expression cassette (FIGS. 1 and 2). As shown in FIG. 1, the enzyme activity from the heterologous enzyme engineered to be expressed in the M18151 background strain is far greater (~60×) than the equivalent strain build in another baking strain background, M18152. While strain M18151 has significantly higher protein content than M18152 (53% compared to 44%, respectively), protein content cannot fully explain such a dramatic difference in heterologous enzyme expression.

Strain M18151 can make and release high levels of enzyme using industrially relevant processes, including homogenization and autolysis (Tables 2 and 3). Strain M155332 uses the M18151 background which was modified to express an intracellular *G. stearothemophilus* maltogenic alpha-amylase (MAA) (M15532). Strain M155332 was propagated by aerobic fed-batch on molasses and a yeast cream was then made. Its MAU activity was determined. As shown in Table 2, the heterologous enzyme is calculated to be 3.7% of total cellular protein.

TABLE 2

Calculations for maltogenic amylase as a percent of total cell protein. Enzyme activity of cream yeast and of purified enzyme was determined in a Phadebas enzyme assay with comparison to a dose curve of the standards with known maltogenic amylase units (MAU).

| | |
|---|---|
| Percent protein in cream | 53.66% |
| Enzyme activity (MAU/g dry cell weight), measured after release by autolysis | 19000 |
| Specific activity of pure enzyme (MAU/mg) | 872 |
| Specific activity of pure enzyme (MAU/g) | 872000 |
| Enzyme per gram dry weight (g/g) | 0.022 |
| Enzyme per total protein (g/g) | 0.041 |
| Enzyme as % of total protein | 4.1% |

TABLE 3

Calculations for maltogenic amylase as a percent of four different batches of dried enzyme material, obtained after autolysis of yeast expressing maltogenic amylase, separation of cell walls, further concentration and purification of the enzyme by ultrafiltration, and spray drying.

| Lot | MAU/g material | Specific activity (MAU/g enzyme) | Estimated enzyme % of material | mg total protein/g material | Enzyme % of protein |
|---|---|---|---|---|---|
| 1 | 208782 | 872000 | 24% | 373.25 | 64% |
| 2 | 287001 | | 33% | 450 | 73% |

TABLE 4

Dry weight and enzyme activity balances in autolysate yeast cell wall, yeast extract, ultrafiltration retentate, and ultrafiltration permeate preparations. Enzyme activity was determined in Phadebas enzyme assays with comparison to a dose curve of a reference commercial enzyme standards with known maltogenic amylase units (MAU). Mass and MAU balances are calculated from experimental data and do not always sum to 100% due to error in dry weight and enzyme assay measurements.

| | STEP YIELD (%) | | TOTAL YIELD (%) | |
|---|---|---|---|---|
| FRACTION | MASS | MAU | MASS | MAU |
| Autolysate | 100 | 100 | 100 | 100 |
| Cell wall | 38 | 21 | 38 | 21 |
| Yeast extract | 54 | 80 | 54 | 80 |
| UF retentate | 33 | 90 | 18 | 71 |
| UF permeate | 57 | 0 | 31 | 0 |

Example II—Characterization of the M18151 Strain

Fed-batch aerobic propagation (Table 5). Percent protein (weight protein/weight biomass) was determined by Kjeldahl method on yeast propagated in aerobic fed-batch on molasses.

Figure 3:
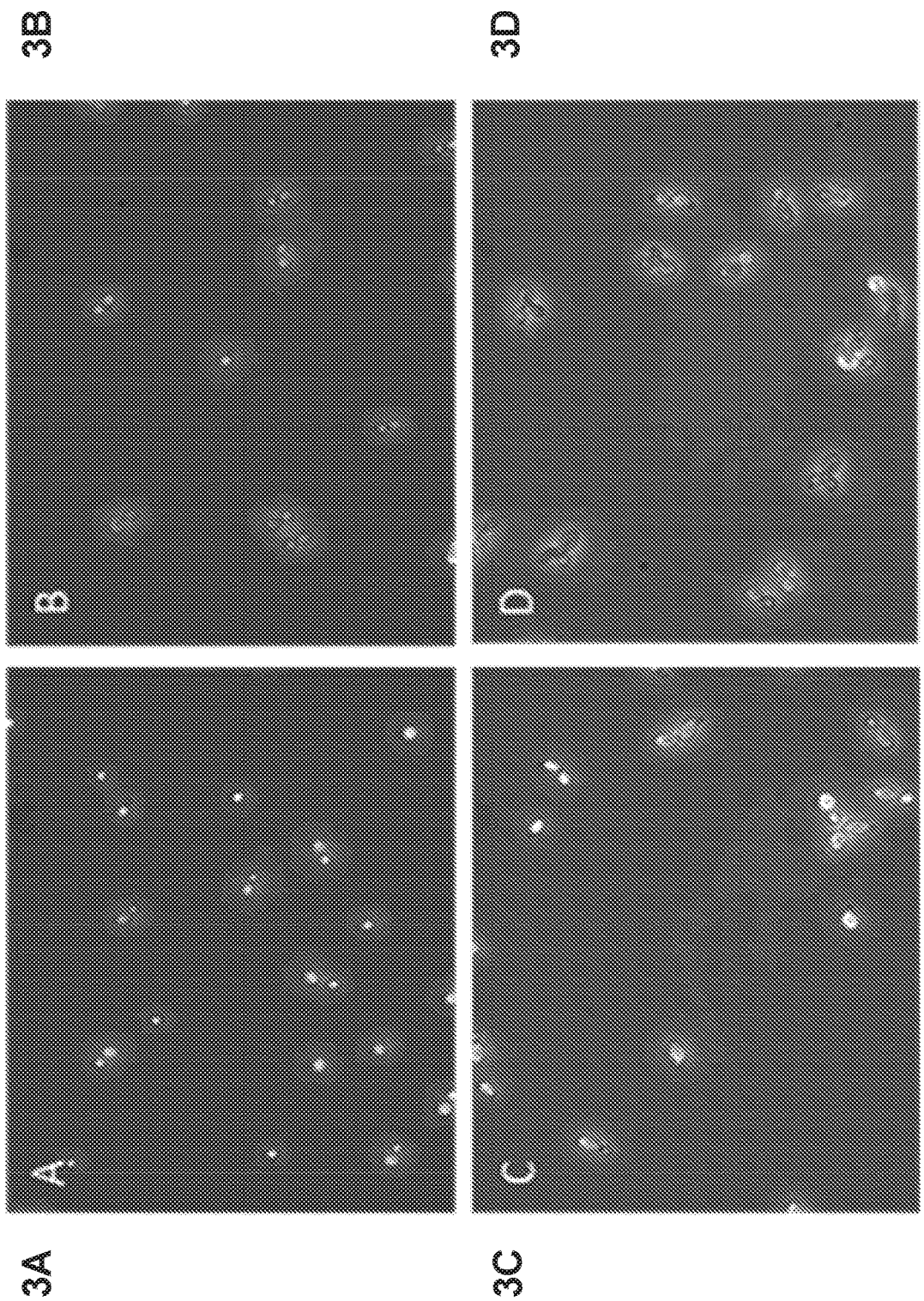
FIGS. 3A to 3D provide light microscopy images of cells of strain M2390 (FIGS. 3A and 3B) or the M18151 strain (FIGS. 3C and D).

Shape characterization (FIG. 3). Yeast strains M2390 and M18151 were grown in yeast extract peptone media with 4% glucose overnight and then transferred into fresh yeast extract peptone media with 4% glucose medium. Cells were imaged under light microscopy at 400× magnification after 1 hr incubation in fresh medium.

Determination of sporulation efficiency. Yeast strains M2390 and M18151 were grown as patches overnight on yeast extract peptone agar plates with 4% glucose. A colony-sized amount of cells were picked from each patch and resuspended in 100 µL sterile deionized water. The cell suspension was plated onto sporulation medium (0.05% yeast extract, 0.5% potassium acetate, 0.025% glucose, 1% agar) and incubated at room temperature for 5 days. To measure sporulation efficiency, a colony sized amount of cells was picked from the sporulation plates and resuspended in 100 µL of sterile deionized water. 8 µL of each cell suspension was transferred to a microscope slide and examined at 1000× magnification for the presence of spores. Per strain, 210 cells were characterized as "sporulated" or "not sporulated" and the "% sporulated" was calculated by dividing the number of sporulated cells by 210.

Morphology on solid media. Strain M18151 was grown on solid yeast extract peptone supplemented with 4% glucose medium.

Ploidy determination. Whole genome de novo sequencing for M18151 was performed. The sequence was compared to the publicly available S288C reference genome, and read coverage as well as frequencies of all single nucleotide polymorphisms, divided by read coverage were aligned to the sequences of the 16 chromosomes of S288C and plotted.

Figure 4:
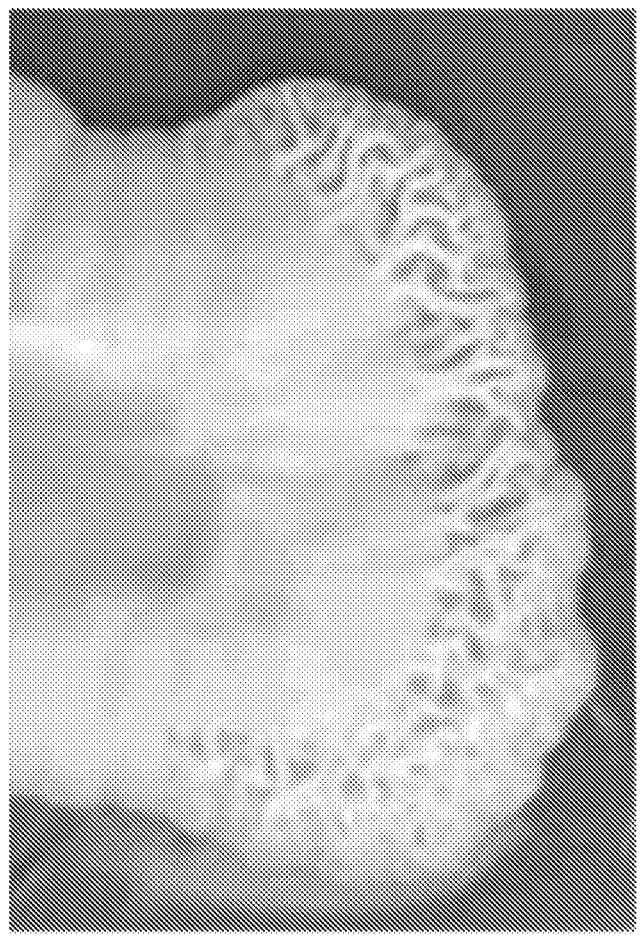
FIG. 4 provides a macroscopic view of the M18151 strain exhibiting complex colony morphology after a few days' growth on solid yeast extract peptone plus 4% glucose medium.
Figure 5:
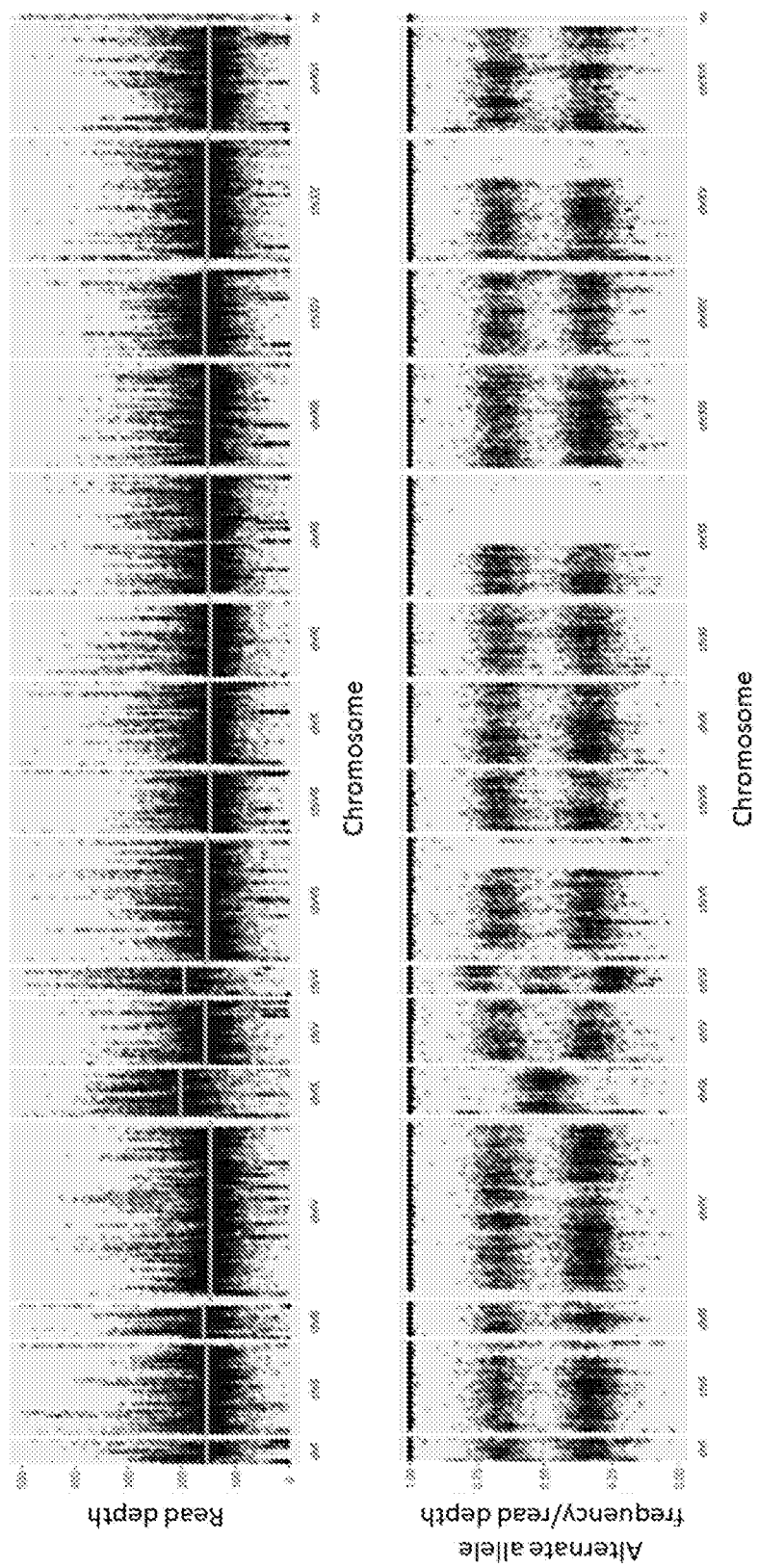
FIG. 5 illustrates the frequency of single nucleotide polymorphisms (SNPs) across chromosomes of M18151 strain. Data plots from chromosomes 1-16 are shown in numerical order from left to right and top to bottom. SNP frequencies can infer the ploidy: 0.5 indicates diploid; 0.33 and 0.67 indicate triploid; 0.25, 0.5, and 0.75 indicate tetraploid. Two chromosomes are tetraploid and the remaining chromosomes are triploid.

After fed-batch aerobic propagation, strain M18151 cells have high protein content relative to other strains propagated under the same conditions (Table 5). In addition, the shape of strain M18151 remained elongated, even in rich media (FIG. 3). Further, strain M18151 has poor sporulation efficiency in response to nitrogen starvation (Table 6). Strain M18151 has a low production yield after fed-batch aerobic propagation, relative to other strains (Table 7). Interestingly, strain M18151 has a complex morphology when grown on solid media (FIG. 4). Furthermore, strain M18151 has higher than diploid ploidy: most of its chromosomes appear to be triploid (present in three copies), with two tetraploid chromosomes, one of which is semi-homozygosed (FIG. 5).

TABLE 5

Comparison of protein content of strains at least duplicate fed-batch aerobic propagations on molasses.

| Strain | Average protein content (%) |
|---|---|
| M18151 | 53.3 |
| M18152 | 43.8 |
| M18195 | 49.4 |

TABLE 6

Percentage of sporulated cells in the M2390 and the M18151 strains after incubation on sporulation medium.

| Strain | % sporulated |
|---|---|
| M2390 | 77 |
| M18152 | 13 |

TABLE 7

Yield of various yeast strains after a least duplicate aerobic fed-batch propagations on molasses

| Strain | Biomass yield (relative to M18152) |
|---|---|
| M18151 | 89% |
| M18152 | 100% |
| M18195 | 85% |

Without wishing to be bound to theory, some of the M18151 strain's phenotypes could be attributed to the higher ploidy of the strain. One example is elongated cell shape; higher ploidy cells have been shown to have both an increased cell size and an increased aspect ratio. Other features of the strain seem to point to altered physiology not necessarily related to ploidy. Specifically, many of the M18151 strain phenotypes are consistent with constitutively upregulated production of cyclic AMP (cAMP), an intracellular signaling molecule central to nutrient signaling and the regulation of several metabolic systems in *Saccharomyces cerevisiae*. Modulations of the Ras/cAMP/PKA pathway result in an array of different phenotypes, including altered sporulation efficiency, pseudohyphal growth, altered stress tolerance, altered levels of the storage carbohydrates glycogen and trehalose, etc. Elevated cAMP in *S. cerevisiae* has been shown to cause complex morphology when strains are grown on solid media and low sporulation efficiency during nitrogen starvation. This condition has also been shown to decrease the production yield for a strain during growth in conditions similar to those of fed-batch propagation.

It was found that strain M18151 has a few mutations in CYR1, a gene that directly affects cAMP levels as the enzyme responsible for converting ATP to cAMP in yeast (Table 8).

TABLE 8

Mutations the CYR1 gene and protein present in the M18151 strain but not in the M18152. NT = nucleotide (corresponding to the numbering of SEQ ID NO: 5 or 7); AA = amino acid (corresponding to the numbering of SEQ ID NO: 6 or 8).

| CYR1 MUTANTS | | AA at position | | |
|---|---|---|---|---|
| NT position | AA position | M18151 | M18152 | Protein domain information (if any) |
| 772 | 258 | T | A | |
| 2504 | 835 | V | A | Leucine-rich repeats (LRR), to which Ras binds |
| 2605 | 869 | K | E | Leucine-rich repeats (LRR), to which Ras binds |
| 4305 | 1435 | E | D | PPM-type phosphatase region |

Elevated levels of cAMP could make a strain a good heterologous protein expression host. Increased cAMP levels have been associated with increased protein content in *S. cerevisiae*, the prevention of the downregulation of ribosome biogenesis and autophagy of cellular components, including proteins. This could lead to higher heterologous enzyme production due to increased rate of translation and a decrease in the degradation of heterologous protein via autophagy.

Increased ploidy could also benefit heterologous protein expression, because any stably engineered genetic construct, if it is present on every copy of a chromosome, will have higher copy number per cell than in a lower ploidy strain.

M18151 strain's elongated, and potentially larger, cell shape could add to the benefit of the strain as an heterologous protein expression host. Its elongated shape provides a higher surface area-to-volume ratio than a spherical shape. Greater cell surface area has been correlated with increased rate of glucose uptake in *S. cerevisiae* strains adapted to glucose-limited conditions, speculated to be due to more space in the cell membrane for the insertion of nutrient transporters. Faster nutrient uptake could quicken general cell metabolism, including heterologous protein production. A larger cell surface may also result in an increase in heterologous enzyme secretion or release during autolysis processes, since there would be more area from which protein release can occur.

While the invention has been described in connection with specific embodiments thereof, it will be understood that the scope of the claims should not be limited by the preferred embodiments set forth in the examples, but should be given the broadest interpretation consistent with the description as a whole.

What is claimed is:

1. A recombinant yeast host cell for making an increased amount of a heterologous protein, wherein the recombinant yeast host cell:
   (i) (a) has a first heterologous nucleic acid encoding the heterologous protein; and
   (b) expresses a variant CYR1 protein; and/or
   (ii) is obtained by introducing the first heterologous nucleic acid encoding the heterologous protein in an ancestral yeast host cell that expresses a variant CYR1 protein;
   wherein the variant CYR1 protein:
      provides to the recombinant yeast host cell or the ancestral yeast host cell a similar intracellular cAMP production in the presence and in the absence of a cAMP stimulus known to stimulate intracellular cAMP production in a control yeast cell, and
      comprises the amino acid sequence of SEQ ID NO: 8 with a substitution at position 869 or a variant thereof having 90% identity with the amino acid sequence of SEQ ID NO: 8 with a substitution at position 869.

2. The recombinant yeast host cell of claim 1, wherein the amount of heterologous protein per cell of the recombinant yeast host cell is increased with respect to a corresponding amount in a control yeast cell.

3. The recombinant yeast host cell of claim 1, wherein the control yeast cell corresponds to biological deposit PTA-125176 or a yeast cell having the characteristics of the biological deposit PTA-125176; the ancestral yeast host cell is biological deposit PTA-125175 or a yeast cell having the characteristics of the biological deposit PTA-125175; and/or the ancestral yeast host cell is biological deposit PTA-125177 or a yeast cell having the characteristics of the biological deposit PTA-125177.

4. The recombinant yeast host cell of claim 1, wherein the variant CYR1 protein is encoded by a variant CYR1 gene, the variant CYR1 gene is a native CYR1 gene in the yeast ancestral host cell, or the recombinant yeast host cell comprises a second heterologous nucleic acid molecule comprising the variant CYR1 gene.

5. The recombinant yeast host cell of claim 4, wherein the variant CYR1 gene has at least one single nucleotide polymorphism (SNP).

6. The recombinant yeast host cell of claim 5, wherein the at least one SNP comprises G2605A when using the numbering of the nucleic acid sequence of SEQ ID NO: 7.

7. The recombinant yeast host cell of claim 4, wherein the variant CYR1 protein has an E869K substitution when using the numbering of the amino acid sequence of SEQ ID NO: 8.

8. The recombinant yeast host cell of claim 1 exhibiting polyploidy in at least one chromosome.

9. The recombinant yeast host cell of claim 8, wherein polyploidy comprises triploidy in at least one first chromosome and tetraploidy in at least one second chromosome.

10. The recombinant yeast host cell of claim 1, wherein the heterologous protein is a heterologous enzyme.

11. The recombinant yeast host cell of claim 10, wherein the heterologous enzyme is at least one of a maltogenic alpha-amylase, an alpha-amylase, an oxidoreductase, a transferase, an hydrolase, a lyase, an isomerase, a phosphatase, a ligase, a glucoamylase, a fungal amylase, a phytase or a glucose oxidase.

12. The recombinant yeast host cell of claim 1 being a cell of genus *Saccharomyces* or a cell of species *Saccharomyces cerevisiae*.

13. A method of making the recombinant yeast host cell of claim 1, the method comprising:
    a) selecting an ancestral yeast host cell as defined in claim 1; and
    b) introducing a first heterologous nucleic acid molecule encoding the heterologous protein in the selected ancestral host cell to obtain the recombinant yeast host cell.

14. A process for making a yeast product, the process comprising:
    i) culturing the recombinant yeast host cell of claim 1 to obtain a cultured recombinant yeast host cell; and
    ii) formulating the cultured yeast host cell into the yeast product.

15. The process of claim 14 comprising, at step ii):
    a) lysing the cultured yeast host cell to obtain a lysed yeast product.

16. The process of claim 15, wherein the yeast product is an autolysate, a yeast cell wall, a yeast extract, or a purified heterologous protein.

17. The process of claim 16, wherein the purified heterologous protein is an heterologous enzyme.

18. The recombinant yeast host cell of claim 1, wherein the variant CYR1 protein comprises a further substitution at position 258, 827, 835, and/or 1435 when using the numbering of the amino acid sequence of SEQ ID NO: 8.

19. The recombinant yeast host cell of claim 18, wherein the variant CYR1 protein has at least one of the following variations:
    A258T when using the numbering of the amino acid sequence of SEQ ID NO: 2 or 8;
    A827V when using the numbering of the amino acid sequence of SEQ ID NO: 2
    A835V when using the numbering of the amino acid sequence of SEQ ID NO: 8; and/or
    D1435E when using the numbering of the amino acid sequence of SEQ ID NO: 8.

20. The recombinant yeast host cell of claim 19, wherein the variant CYR1 protein is encoded by a variant CYR1 gene having at least one single nucleotide polymorphism (SNP), wherein the at least one SNP is:
    G772A when using the numbering of the nucleic acid sequence of SEQ ID NO: 1 or 7;
    C2480T when using the numbering of the nucleic acid sequence of SEQ ID NO: 1; or
    C2504T when using the numbering of the nucleic acid sequence of SEQ ID NO: 7; or
    C4305A when using the numbering of the nucleic acid sequence of SEQ ID NO: 7.

21. The process of claim 15 comprising, at step ii):
    b) drying the lysed recombinant yeast host cell to obtain a lysed and dried yeast product.

* * * * *

SEQUENCE LISTING

<160> NUMBER OF SEQ ID NOS: 8

<210> SEQ ID NO 1
<211> LENGTH: 6081
<212> TYPE: DNA
<213> ORGANISM: Saccharomyces cerevisiae

<400> SEQUENCE: 1

| | | | | | | |
|---|---|---|---|---|---|---|
| atgtcatcaa | aacctgatac | tggttcggaa | atttctggcc | ctcagcgaca | ggaagaacaa | 60 |
| gaacaacaga | tagagcagag | ctcacctacg | gaagcaaacg | atagaagcat | tcatgatgag | 120 |
| gtaccaaaag | tcaagaagcg | tcacgaacaa | aatagtggtc | acaaatcaag | aaggaatagc | 180 |
| gcatatagtt | attacagccc | acggtcgctt | tctatgacca | aaagcaggga | gagtatcact | 240 |
| ccaaatggta | tggatgatgt | aagtatttcg | aacgtggaac | atccaaggcc | gacagaaccg | 300 |
| aaaatcaaaa | ggggtccata | tttactgaag | aaaacattga | gcagtctttc | aatgacgagc | 360 |
| gcgaatagta | ctcatgatga | taataaagac | cacggttacg | ctttgaattc | atccaagacg | 420 |
| cacaactaca | catctactca | taaccatcat | gacggtcatc | atgatcatca | tcatgttcag | 480 |
| ttttttccca | ataggaagcc | atcattagcg | gaaaccctat | tcaaaaggtt | ttcagggtca | 540 |
| aacagtcacg | atggcaataa | gtcaggaaag | gaaagtaaag | ttgctaacct | ttcccttttca | 600 |
| acggtaaatc | ctgcacctgc | taataggaaa | ccttctaaag | actccacttt | atctaatcac | 660 |
| ttggctgata | acgtgccaag | cactttacga | aggaaagtgt | cctcattggt | acgtggttct | 720 |
| tccgtccatg | atataaataa | tggtattgca | gataaacaga | ttagaccaaa | ggctgttgcg | 780 |
| caatcagaaa | atacattaca | ttcatccgat | gttcccaata | gcaaacgctc | gcacagaaaa | 840 |
| agctttctgc | taggctccac | atcttcttca | agcagtagaa | gaggttcaaa | tgtcagttca | 900 |
| atgactaaca | gtgacagtgc | aagtatggcg | acgtcgggta | gtcatgttct | ccaacataac | 960 |
| gtatctaatg | tttctccaac | tactaaaagt | aaggacagcg | ttaacagcga | atccgccgat | 1020 |
| cacactaata | ataaatccga | gaaagtgact | ccagaatata | atgagaacat | tccggaaaat | 1080 |
| tctaactctg | acaacaaacg | cgaagccaca | acgcctacta | tagaaacacc | catttcatgt | 1140 |
| aaaccatccc | ttttcaggct | agatacaaac | cttgaggatg | ttactgatat | tacaaagacg | 1200 |
| gtgccaccca | ccgctgtcaa | ttctacacta | aattctacac | acgggactga | gactgcctca | 1260 |
| cccaaaacgg | tgatcatgcc | tgaaggtcct | aggaagtcgg | tgtcaatggc | tgatctctcc | 1320 |
| gtcgctgccg | cagcacctaa | tggtgaattc | acatcaactt | ccaatgatag | atcacaatgg | 1380 |
| gtagcacctc | aaagctggga | tgtggaaacc | aaaaggaaaa | aaacaaaacc | taaagggaga | 1440 |
| tcgaaatcaa | gaaggtcaag | tatagatgct | gatgaacttg | atcccatgtc | accggggcca | 1500 |
| ccttcaaaaa | aagactctcg | tcatcatcac | gatcgaaagg | ataacgaatc | aatggtcact | 1560 |
| gcgggtgaca | gtaactcaag | ttttgttgat | atatgtaaag | aaaacgttcc | gaatgatagc | 1620 |
| aagaccgcac | tcgatactaa | atctgtgaac | cgcttaaaaa | gtaatttggc | tatgagtccc | 1680 |

```
ccaagtatac gatatgctcc atcaaattta gatggggact acgacacgtc ttccacttcc    1740
tcatctttac cgtcctcatc tattagttca aagatacact cttcctgcag cgattcctct    1800
tcgtacacta acgcgtatat ggaggccaac cgagagcagg ataataaaac accgatcctg    1860
aataaaacga atcgtatac caagaaattt acatcctctt cggtaaatat gaattcacca     1920
gatggtgccc agagttctgg attattacta caagatgaga aggacgatga ggtcgagtgc    1980
caactggaac attactataa agatttcagt gatttagatc caagaggca ctatgctatt     2040 cgtatattca atactgatga cacttttacg actctctcat gtactccagc gactaccgtc    2100
gaagagataa tacctgcact taaaagaaaa tttaacatta cagcgcaagg gaattttcaa    2160
atttccctga aggtgggaaa gttgtcaaaa attttgagac caacttcgaa acctatttta    2220
attgaaagaa aacttttact tttgaatggt tatcgaaagt cagacccact tcatattatg    2280
ggtatagagg atttaagttt tgttttaag tttcttttcc atcctgtcac accttctcac     2340
tttactcctg aacaagaaca aagaataatg agaagcgaat tgttcacgt agatttaagg     2400 aatatggatc tgactacacc tcccatcatt ttttaccagc atacgtcaga aatagaaagt    2460
ttagacgttt ctaataacgc aaatatattc ctacctctgg agttcattga agctcgatt     2520 aaattattaa gtttgagaat ggttaatatt agagcatcta aatttccttc caatatcact    2580
aaggcgtata aactagtatc tttggaatta cagagaaact tcataagaaa agtaccgaac    2640
tcaatcatga aactgagtaa tttaacgata ttaaaccttc aatgtaatga gcttgaaagc    2700
ctaccggctg gatttgttga actgaaaaat ctgcaattgc tagacttgtc ttcaaacaag    2760
ttcatgcact acccagaagt tattaactac tgcaccaatc ttttacaaat agacctatca    2820
tataataaaa tccaaagctt accacagtcc actaagtacc tagtaaagct gcgaagatg     2880 aacctttctc ataacaaact aaattttata ggcgacttat cggaaatgac agatttgagg    2940
acgctgaacc taagatataa cagaatatca tcaattaaga caaatgcgtc taacttgcag    3000 aaccttttt taacagataa tagaatttcg aactttgaag acactttgcc gaaactaaga    3060
gcccttgaaa ttcaagagaa tccaatcact tctatatcct tcaaagattt ttatccaaaa    3120
aacatgacaa gtttgacgtt gaacaaggca cagttatcga gtattcctgg agaattactc    3180
accaaactat ctttcctcga gaaacttgaa cttaatcaga ataatttgac tagactgcca    3240
caggagatat ccaagttgac taaattagtt ttcctttcag tggcgagaaa caaactagag    3300
tatattccac ccgagctatc tcaactgaaa agtttgagga cattagatct acattctaac    3360
aacataaggg actttgttga cggtatggaa aaccttgaac taacatcgct aaatatttca    3420
tcgaatgcat tcggtaactc tagcttagaa aattctttt accataacat gtcatatggg    3480
tcaaagttat ctaaaagcct gatgtttttt attgctgcag acaatcaatt tgatgatgct    3540
atgtggcctc ttttcaattg ctttgtcaat ctgaaagtgc taaatctttc ttacaacaat    3600
ttttcagatg tatcgcacat gaaacttgag agcattaccg aattgtacct ctccggtaat    3660
aagctcacga cattgtcggg tgatacagtt ttgaaatgga gctctttaaa gactttaatg    3720
ttgaatagta accaaatgtt atctctgcct gcagaattat caaatctctc acagctaagt    3780
gtatttgatg ttggagcaaa tcaattaaag tataatatat caaactatca ttacgattgg    3840
aactggagga ataataaaga actaaaatat ttgaattttt caggaaatcg aaggtttgaa    3900
ataaagtcat ttataagtca cgatattgat gctgatttgt cagatctgac agtattacct    3960
cagttaaagg tactaggttt aatggacgta actttaaata ctaccaaagt accggatgaa    4020
aatgtcaatt tccgtttaag gacaactgca tcaataataa atgggatgcg ctacggtgtt    4080
```

-continued

```
gctgatacat taggtcaaag agactatgtg tcatctcgtg atgttacctt tgaaagattc    4140
cgcggaaatg acgacgaatg cttactatgt cttcatgata gtaaaaacca aaatgcagat    4200
tatggccaca atatatcaag aattgttaga gatatttacg ataaaatact gatcagacaa    4260
ctggaaaggt atggagacga aacagatgat aaatataaaaa ctgcacttcg tttcagtttt    4320
ttgcaactga ataaggagat taacggaatg ctaaattctg ttgataatgg tgccgatgtt    4380
gccaatcttt catatgcaga cttgctaagt ggcgcttgct ctactgtgat atatatcaga    4440
gggaagaaac tcttcgctgc aaatttaggt gactgtatgg ctattttatc caaaaacaat    4500
ggtgactacc aaacgctaac caaacaacat ctcccaacaa gcgggaaga atacgagagg    4560 atcagaatat ctggcgggta tgtcaacaat ggaaaattag atggtgttgt agatgtgtct    4620
agagcagtgg gttttttttga tttgcttccc cacattcatg cttctcccga catatctgtc    4680
gtgacattaa caaaagcaga cgagatgctt attgtagcaa cgcataagtt atgggaatac    4740
atggacgtgg atacagtttg tgatatcgcg cgtgagaata gtactgatcc actccgtgcc    4800
gcagctgagt tgaaggatca tgccatggct tacggctgta cagagaatat tacaattttg    4860
tgccttgctc tttacgagaa cattcagcaa caaaatcggt tcactttaaa taaaaactct    4920
ttaatgacta gaagaagtac tttcgaggat actacattaa gaagacttca acctgagatt    4980
tctccgccaa caggtaaccct agcaatggtc ttcactgata tcaaaagctc aaccttctta    5040
tgggagctat tccctaacgc aatgaggacc gcaataaaaa ctcacaatga cattatgcgt    5100
cgtcaactac gaatttacgg tggttacgaa gtaaagacag aaggagacgc ctttatggtg    5160
gcatttccta cgccaactag tggtctgaca tggtgcttaa gtgttcaatt aaaactcttg    5220
gatgcacaat ggccggagga aattacctca gttcaagacg gctgccaagt tacggataga    5280
aatggtaaca ttatctatca aggcctatca gttagaatgg gtattcattg gggctgccca    5340
gttccagagc ttgatttagt gactcaaaga atggactatt tggggccgat ggtcaataag    5400
gcagcaaggg tccagggcgt cgctgacggt ggtcagattg caatgagtag tgatttttac    5460
tctgaattca acaagataat gaagtatcat gagcgagtag tgaagggcaa ggaatctctc    5520
aaggaagttt atggtgaaga aattatcgga gaggttcttg aaagagaaat tgccatgctg    5580
gaaagtattg gttgggcatt ttttgacttt ggcgagcata agctaaaggg actcgaaacc    5640
aaagaactcg ttactattgc gtatcctaag attcttgctt ccagacacga atttgcatct    5700
gaagatgagc agtcaaaatt aatcaatgaa acgatgttgt ttcgtttaag agtcatttca    5760
aacagactgg aatctataat gtcagctta agcggcggat ttattgaact agactctcgg    5820
acggagggaa gttatattaa attaaccct aaagttgaaa atggtattat gcaatcgatt    5880
tctgagaagg atgcgttgtt attttttgat catgtaatta ctagaatcga atccagtgtg    5940
gcattattac atttacgaca acagaggtgt tcaggactgg aaatttgcag aaacgataaa    6000
acatctgctc gaagcaatat tttcaatgtt gttgacgaac ttttacaaat ggttaagaac    6060
gcaaaggatt tatcaacttg a                                               6081
```

<210> SEQ ID NO 2
<211> LENGTH: 2026
<212> TYPE: PRT
<213> ORGANISM: Saccharomyces cerevisiae

<400> SEQUENCE: 2

Met Ser Ser Lys Pro Asp Thr Gly Ser Glu Ile Ser Gly Pro Gln Arg
1               5                   10                  15

```
Gln Glu Glu Gln Glu Gln Ile Glu Gln Ser Ser Pro Thr Glu Ala
                20                  25                  30

Asn Asp Arg Ser Ile His Asp Glu Val Pro Lys Val Lys Lys Arg His
            35                  40                  45

Glu Gln Asn Ser Gly His Lys Ser Arg Arg Asn Ser Ala Tyr Ser Tyr
        50                  55                  60

Tyr Ser Pro Arg Ser Leu Ser Met Thr Lys Ser Arg Glu Ser Ile Thr
65                  70                  75                  80

Pro Asn Gly Met Asp Asp Val Ser Ile Ser Asn Val Glu His Pro Arg
                85                  90                  95

Pro Thr Glu Pro Lys Ile Lys Arg Gly Pro Tyr Leu Leu Lys Lys Thr
            100                 105                 110

Leu Ser Ser Leu Ser Met Thr Ser Ala Asn Ser Thr His Asp Asp Asn
        115                 120                 125

Lys Asp His Gly Tyr Ala Leu Asn Ser Ser Lys Thr His Asn Tyr Thr
130                 135                 140

Ser Thr His Asn His His Asp Gly His His Asp His His Val Gln
145                 150                 155                 160

Phe Phe Pro Asn Arg Lys Pro Ser Leu Ala Glu Thr Leu Phe Lys Arg
                165                 170                 175

Phe Ser Gly Ser Asn Ser His Asp Gly Asn Lys Ser Gly Lys Glu Ser
            180                 185                 190

Lys Val Ala Asn Leu Ser Leu Ser Thr Val Asn Pro Ala Pro Ala Asn
        195                 200                 205

Arg Lys Pro Ser Lys Asp Ser Thr Leu Ser Asn His Leu Ala Asp Asn
210                 215                 220

Val Pro Ser Thr Leu Arg Arg Lys Val Ser Ser Leu Val Arg Gly Ser
225                 230                 235                 240

Ser Val His Asp Ile Asn Asn Gly Ile Ala Asp Lys Gln Ile Arg Pro
                245                 250                 255

Lys Ala Val Ala Gln Ser Glu Asn Thr Leu His Ser Ser Asp Val Pro
            260                 265                 270

Asn Ser Lys Arg Ser His Arg Lys Ser Phe Leu Leu Gly Ser Thr Ser
        275                 280                 285

Ser Ser Ser Ser Arg Arg Gly Ser Asn Val Ser Ser Met Thr Asn Ser
290                 295                 300

Asp Ser Ala Ser Met Ala Thr Ser Gly Ser His Val Leu Gln His Asn
305                 310                 315                 320

Val Ser Asn Val Ser Pro Thr Thr Lys Ser Lys Asp Ser Val Asn Ser
                325                 330                 335

Glu Ser Ala Asp His Thr Asn Asn Lys Ser Glu Lys Val Thr Pro Glu
            340                 345                 350

Tyr Asn Glu Asn Ile Pro Glu Asn Ser Asn Ser Asp Asn Lys Arg Glu
        355                 360                 365

Ala Thr Thr Pro Thr Ile Glu Thr Pro Ile Ser Cys Lys Pro Ser Leu
370                 375                 380

Phe Arg Leu Asp Thr Asn Leu Glu Asp Val Thr Asp Ile Thr Lys Thr
385                 390                 395                 400

Val Pro Pro Thr Ala Val Asn Ser Thr Leu Asn Ser Thr His Gly Thr
                405                 410                 415

Glu Thr Ala Ser Pro Lys Thr Val Ile Met Pro Glu Gly Pro Arg Lys
            420                 425                 430
```

-continued

```
Ser Val Ser Met Ala Asp Leu Ser Val Ala Ala Ala Pro Asn Gly
            435                 440                 445

Glu Phe Thr Ser Thr Ser Asn Asp Arg Ser Gln Trp Val Ala Pro Gln
450                 455                 460

Ser Trp Asp Val Glu Thr Lys Arg Lys Thr Lys Pro Lys Gly Arg
465                 470                 475                 480

Ser Lys Ser Arg Arg Ser Ser Ile Asp Ala Asp Glu Leu Asp Pro Met
                485                 490                 495

Ser Pro Gly Pro Pro Ser Lys Lys Asp Ser Arg His His His Asp Arg
            500                 505                 510

Lys Asp Asn Glu Ser Met Val Thr Ala Gly Asp Ser Asn Ser Ser Phe
            515                 520                 525

Val Asp Ile Cys Lys Glu Asn Val Pro Asn Asp Ser Lys Thr Ala Leu
            530                 535                 540

Asp Thr Lys Ser Val Asn Arg Leu Lys Ser Asn Leu Ala Met Ser Pro
545                 550                 555                 560

Pro Ser Ile Arg Tyr Ala Pro Ser Asn Leu Asp Gly Asp Tyr Asp Thr
                565                 570                 575

Ser Ser Thr Ser Ser Ser Leu Pro Ser Ser Ser Ile Ser Ser Glu Asp
            580                 585                 590

Thr Ser Ser Cys Ser Asp Ser Ser Ser Tyr Thr Asn Ala Tyr Met Glu
            595                 600                 605

Ala Asn Arg Glu Gln Asp Asn Lys Thr Pro Ile Leu Asn Lys Thr Lys
            610                 615                 620

Ser Tyr Thr Lys Lys Phe Thr Ser Ser Ser Val Asn Met Asn Ser Pro
625                 630                 635                 640

Asp Gly Ala Gln Ser Ser Gly Leu Leu Leu Gln Asp Glu Lys Asp Asp
                645                 650                 655

Glu Val Glu Cys Gln Leu Glu His Tyr Tyr Lys Asp Phe Ser Asp Leu
                660                 665                 670

Asp Pro Lys Arg His Tyr Ala Ile Arg Ile Phe Asn Thr Asp Asp Thr
            675                 680                 685

Phe Thr Thr Leu Ser Cys Thr Pro Ala Thr Thr Val Glu Glu Ile Ile
690                 695                 700

Pro Ala Leu Lys Arg Lys Phe Asn Ile Thr Ala Gln Gly Asn Phe Gln
705                 710                 715                 720

Ile Ser Leu Lys Val Gly Lys Leu Ser Lys Ile Leu Arg Pro Thr Ser
                725                 730                 735

Lys Pro Ile Leu Ile Glu Arg Lys Leu Leu Leu Leu Asn Gly Tyr Arg
            740                 745                 750

Lys Ser Asp Pro Leu His Ile Met Gly Ile Glu Asp Leu Ser Phe Val
            755                 760                 765

Phe Lys Phe Leu Phe His Pro Val Thr Pro Ser His Phe Thr Pro Glu
            770                 775                 780

Gln Glu Gln Arg Ile Met Arg Ser Glu Phe Val His Val Asp Leu Arg
785                 790                 795                 800

Asn Met Asp Leu Thr Thr Pro Pro Ile Ile Phe Tyr Gln His Thr Ser
                805                 810                 815

Glu Ile Glu Ser Leu Asp Val Ser Asn Asn Ala Asn Ile Phe Leu Pro
            820                 825                 830

Leu Glu Phe Ile Glu Ser Ser Ile Lys Leu Leu Ser Leu Arg Met Val
            835                 840                 845
```

```
Asn Ile Arg Ala Ser Lys Phe Pro Ser Asn Ile Thr Lys Ala Tyr Lys
850                 855                 860

Leu Val Ser Leu Glu Leu Gln Arg Asn Phe Ile Arg Lys Val Pro Asn
865                 870                 875                 880

Ser Ile Met Lys Leu Ser Asn Leu Thr Ile Leu Asn Leu Gln Cys Asn
                885                 890                 895

Glu Leu Glu Ser Leu Pro Ala Gly Phe Val Glu Leu Lys Asn Leu Gln
                900                 905                 910

Leu Leu Asp Leu Ser Ser Asn Lys Phe Met His Tyr Pro Glu Val Ile
                915                 920                 925

Asn Tyr Cys Thr Asn Leu Leu Gln Ile Asp Leu Ser Tyr Asn Lys Ile
930                 935                 940

Gln Ser Leu Pro Gln Ser Thr Lys Tyr Leu Val Lys Leu Ala Lys Met
945                 950                 955                 960

Asn Leu Ser His Asn Lys Leu Asn Phe Ile Gly Asp Leu Ser Glu Met
                965                 970                 975

Thr Asp Leu Arg Thr Leu Asn Leu Arg Tyr Asn Arg Ile Ser Ser Ile
                980                 985                 990

Lys Thr Asn Ala Ser Asn Leu Gln Asn Leu Phe Leu Thr Asp Asn Arg
                995                 1000                1005

Ile Ser Asn Phe Glu Asp Thr Leu Pro Lys Leu Arg Ala Leu Glu
    1010                1015                1020

Ile Gln Glu Asn Pro Ile Thr Ser Ile Ser Phe Lys Asp Phe Tyr
    1025                1030                1035

Pro Lys Asn Met Thr Ser Leu Thr Leu Asn Lys Ala Gln Leu Ser
    1040                1045                1050

Ser Ile Pro Gly Glu Leu Leu Thr Lys Leu Ser Phe Leu Glu Lys
    1055                1060                1065

Leu Glu Leu Asn Gln Asn Asn Leu Thr Arg Leu Pro Gln Glu Ile
    1070                1075                1080

Ser Lys Leu Thr Lys Leu Val Phe Leu Ser Val Ala Arg Asn Lys
    1085                1090                1095

Leu Glu Tyr Ile Pro Pro Glu Leu Ser Gln Leu Lys Ser Leu Arg
    1100                1105                1110

Thr Leu Asp Leu His Ser Asn Asn Ile Arg Asp Phe Val Asp Gly
    1115                1120                1125

Met Glu Asn Leu Glu Leu Thr Ser Leu Asn Ile Ser Ser Asn Ala
    1130                1135                1140

Phe Gly Asn Ser Ser Leu Glu Asn Ser Phe Tyr His Asn Met Ser
    1145                1150                1155

Tyr Gly Ser Lys Leu Ser Lys Ser Leu Met Phe Phe Ile Ala Ala
    1160                1165                1170

Asp Asn Gln Phe Asp Asp Ala Met Trp Pro Leu Phe Asn Cys Phe
    1175                1180                1185

Val Asn Leu Lys Val Leu Asn Leu Ser Tyr Asn Asn Phe Ser Asp
    1190                1195                1200

Val Ser His Met Lys Leu Glu Ser Ile Thr Glu Leu Tyr Leu Ser
    1205                1210                1215

Gly Asn Lys Leu Thr Thr Leu Ser Gly Asp Thr Val Leu Lys Trp
    1220                1225                1230

Ser Ser Leu Lys Thr Leu Met Leu Asn Ser Asn Gln Met Leu Ser
    1235                1240                1245
```

-continued

Leu Pro Ala Glu Leu Ser Asn Leu Ser Gln Leu Ser Val Phe Asp
1250                1255                1260

Val Gly Ala Asn Gln Leu Lys Tyr Asn Ile Ser Asn Tyr His Tyr
1265                1270                1275

Asp Trp Asn Trp Arg Asn Asn Lys Glu Leu Lys Tyr Leu Asn Phe
1280                1285                1290

Ser Gly Asn Arg Arg Phe Glu Ile Lys Ser Phe Ile Ser His Asp
1295                1300                1305

Ile Asp Ala Asp Leu Ser Asp Leu Thr Val Leu Pro Gln Leu Lys
1310                1315                1320

Val Leu Gly Leu Met Asp Val Thr Leu Asn Thr Thr Lys Val Pro
1325                1330                1335

Asp Glu Asn Val Asn Phe Arg Leu Arg Thr Thr Ala Ser Ile Ile
1340                1345                1350

Asn Gly Met Arg Tyr Gly Val Ala Asp Thr Leu Gly Gln Arg Asp
1355                1360                1365

Tyr Val Ser Ser Arg Asp Val Thr Phe Glu Arg Phe Arg Gly Asn
1370                1375                1380

Asp Asp Glu Cys Leu Leu Cys Leu His Asp Ser Lys Asn Gln Asn
1385                1390                1395

Ala Asp Tyr Gly His Asn Ile Ser Arg Ile Val Arg Asp Ile Tyr
1400                1405                1410

Asp Lys Ile Leu Ile Arg Gln Leu Glu Arg Tyr Gly Asp Glu Thr
1415                1420                1425

Asp Asp Asn Ile Lys Thr Ala Leu Arg Phe Ser Phe Leu Gln Leu
1430                1435                1440

Asn Lys Glu Ile Asn Gly Met Leu Asn Ser Val Asp Asn Gly Ala
1445                1450                1455

Asp Val Ala Asn Leu Ser Tyr Ala Asp Leu Leu Ser Gly Ala Cys
1460                1465                1470

Ser Thr Val Ile Tyr Ile Arg Gly Lys Lys Leu Phe Ala Ala Asn
1475                1480                1485

Leu Gly Asp Cys Met Ala Ile Leu Ser Lys Asn Asn Gly Asp Tyr
1490                1495                1500

Gln Thr Leu Thr Lys Gln His Leu Pro Thr Lys Arg Glu Glu Tyr
1505                1510                1515

Glu Arg Ile Arg Ile Ser Gly Gly Tyr Val Asn Asn Gly Lys Leu
1520                1525                1530

Asp Gly Val Val Asp Val Ser Arg Ala Val Gly Phe Phe Asp Leu
1535                1540                1545

Leu Pro His Ile His Ala Ser Pro Asp Ile Ser Val Val Thr Leu
1550                1555                1560

Thr Lys Ala Asp Glu Met Leu Ile Val Ala Thr His Lys Leu Trp
1565                1570                1575

Glu Tyr Met Asp Val Asp Thr Val Cys Asp Ile Ala Arg Glu Asn
1580                1585                1590

Ser Thr Asp Pro Leu Arg Ala Ala Ala Glu Leu Lys Asp His Ala
1595                1600                1605

Met Ala Tyr Gly Cys Thr Glu Asn Ile Thr Ile Leu Cys Leu Ala
1610                1615                1620

Leu Tyr Glu Asn Ile Gln Gln Gln Asn Arg Phe Thr Leu Asn Lys
1625                1630                1635

```
Asn Ser Leu Met Thr Arg Arg Ser Thr Phe Glu Asp Thr Thr Leu
1640                1645                1650

Arg Arg Leu Gln Pro Glu Ile Ser Pro Pro Thr Gly Asn Leu Ala
1655                1660                1665

Met Val Phe Thr Asp Ile Lys Ser Ser Thr Phe Leu Trp Glu Leu
1670                1675                1680

Phe Pro Asn Ala Met Arg Thr Ala Ile Lys Thr His Asn Asp Ile
1685                1690                1695

Met Arg Arg Gln Leu Arg Ile Tyr Gly Gly Tyr Glu Val Lys Thr
1700                1705                1710

Glu Gly Asp Ala Phe Met Val Ala Phe Pro Thr Pro Thr Ser Gly
1715                1720                1725

Leu Thr Trp Cys Leu Ser Val Gln Leu Lys Leu Leu Asp Ala Gln
1730                1735                1740

Trp Pro Glu Glu Ile Thr Ser Val Gln Asp Gly Cys Gln Val Thr
1745                1750                1755

Asp Arg Asn Gly Asn Ile Ile Tyr Gln Gly Leu Ser Val Arg Met
1760                1765                1770

Gly Ile His Trp Gly Cys Pro Val Pro Glu Leu Asp Leu Val Thr
1775                1780                1785

Gln Arg Met Asp Tyr Leu Gly Pro Met Val Asn Lys Ala Ala Arg
1790                1795                1800

Val Gln Gly Val Ala Asp Gly Gly Gln Ile Ala Met Ser Ser Asp
1805                1810                1815

Phe Tyr Ser Glu Phe Asn Lys Ile Met Lys Tyr His Glu Arg Val
1820                1825                1830

Val Lys Gly Lys Glu Ser Leu Lys Glu Val Tyr Gly Glu Glu Ile
1835                1840                1845

Ile Gly Glu Val Leu Glu Arg Glu Ile Ala Met Leu Glu Ser Ile
1850                1855                1860

Gly Trp Ala Phe Phe Asp Phe Gly Glu His Lys Leu Lys Gly Leu
1865                1870                1875

Glu Thr Lys Glu Leu Val Thr Ile Ala Tyr Pro Lys Ile Leu Ala
1880                1885                1890

Ser Arg His Glu Phe Ala Ser Glu Asp Glu Gln Ser Lys Leu Ile
1895                1900                1905

Asn Glu Thr Met Leu Phe Arg Leu Arg Val Ile Ser Asn Arg Leu
1910                1915                1920

Glu Ser Ile Met Ser Ala Leu Ser Gly Gly Phe Ile Glu Leu Asp
1925                1930                1935

Ser Arg Thr Glu Gly Ser Tyr Ile Lys Phe Asn Pro Lys Val Glu
1940                1945                1950

Asn Gly Ile Met Gln Ser Ile Ser Glu Lys Asp Ala Leu Leu Phe
1955                1960                1965

Phe Asp His Val Ile Thr Arg Ile Glu Ser Ser Val Ala Leu Leu
1970                1975                1980

His Leu Arg Gln Gln Arg Cys Ser Gly Leu Glu Ile Cys Arg Asn
1985                1990                1995

Asp Lys Thr Ser Ala Arg Ser Asn Ile Phe Asn Val Val Asp Glu
2000                2005                2010

Leu Leu Gln Met Val Lys Asn Ala Lys Asp Leu Ser Thr
2015                2020                2025
```

<210> SEQ ID NO 3
<211> LENGTH: 686
<212> TYPE: PRT
<213> ORGANISM: Geobacillus stearothermophilus

<400> SEQUENCE: 3

```
Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
    210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
    290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365

Gly Gly Asn Asp Pro Tyr Asn Arg Gly Met Met Pro Ala Phe Asp Thr
    370                 375                 380
```

```
Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Gln Arg Trp Ile Asn
            405                 410                 415

Asn Asp Val Tyr Ile Tyr Glu Arg Lys Phe Asn Asp Val Val Leu
        420                 425                 430

Val Ala Ile Asn Arg Asn Thr Gln Ser Ser Tyr Ser Ile Ser Gly Leu
        435                 440                 445

Gln Thr Ala Leu Pro Asn Gly Ser Tyr Ala Asp Tyr Leu Ser Gly Leu
    450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
            485                 490                 495

Ser Ala Pro Gln Ile Gly Ser Val Ala Pro Asn Met Gly Ile Pro Gly
        500                 505                 510

Asn Val Val Thr Ile Asp Gly Lys Gly Phe Gly Thr Thr Gln Gly Thr
        515                 520                 525

Val Thr Phe Gly Gly Val Thr Ala Thr Val Lys Ser Trp Thr Ser Asn
530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
            565                 570                 575

Leu Ser Gly Thr Gln Thr Ser Val Val Phe Thr Val Lys Ser Ala Pro
        580                 585                 590

Pro Thr Asn Leu Gly Asp Lys Ile Tyr Leu Thr Gly Asn Ile Pro Glu
        595                 600                 605

Leu Gly Asn Trp Ser Thr Asp Thr Ser Gly Ala Val Asn Asn Ala Gln
610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Phe Ile Lys Arg Ala
            645                 650                 655

Asp Gly Thr Ile Gln Trp Glu Asn Gly Ser Asn His Val Ala Thr Thr
        660                 665                 670

Pro Thr Gly Ala Thr Gly Asn Ile Thr Val Thr Trp Gln Asn
        675                 680                 685

<210> SEQ ID NO 4
<211> LENGTH: 434
<212> TYPE: PRT
<213> ORGANISM: Pyrococcus furiosus

<400> SEQUENCE: 4

Lys Tyr Leu Glu Leu Glu Glu Gly Gly Val Ile Met Gln Ala Phe Tyr
1               5                   10                  15

Trp Asp Val Pro Gly Gly Gly Ile Trp Trp Asp His Ile Arg Ser Lys
            20                  25                  30

Ile Pro Glu Trp Tyr Glu Ala Gly Ile Ser Ala Ile Trp Leu Pro Pro
        35                  40                  45

Pro Ser Lys Gly Met Ser Gly Gly Tyr Ser Met Gly Tyr Asp Pro Tyr
    50                  55                  60

Asp Tyr Phe Asp Leu Gly Glu Tyr Tyr Gln Lys Gly Thr Val Glu Thr
65                  70                  75                  80
```

```
Arg Phe Gly Ser Lys Glu Glu Leu Val Arg Leu Ile Gln Thr Ala His
                 85                  90                  95

Ala Tyr Gly Ile Lys Val Ile Ala Asp Val Val Ile Asn His Arg Ala
            100                 105                 110

Gly Gly Asp Leu Glu Trp Asn Pro Phe Val Gly Asp Tyr Thr Trp Thr
        115                 120                 125

Asp Phe Ser Lys Val Ala Ser Gly Lys Tyr Thr Ala Asn Tyr Leu Asp
    130                 135                 140

Phe His Pro Asn Glu Leu His Cys Cys Asp Gly Thr Phe Gly Gly
145                 150                 155                 160

Phe Pro Asp Ile Cys His His Lys Glu Trp Asp Gln Tyr Trp Leu Trp
                165                 170                 175

Lys Ser Asn Glu Ser Tyr Ala Ala Tyr Leu Arg Ser Ile Gly Phe Asp
            180                 185                 190

Gly Trp Arg Phe Asp Tyr Val Lys Gly Tyr Gly Ala Trp Val Val Arg
        195                 200                 205

Asp Trp Leu Asn Trp Trp Gly Gly Trp Ala Val Gly Glu Tyr Trp Asp
    210                 215                 220

Thr Asn Val Asp Ala Leu Leu Ser Trp Ala Tyr Glu Ser Gly Ala Lys
225                 230                 235                 240

Val Phe Asp Phe Pro Leu Tyr Tyr Lys Met Asp Glu Ala Phe Asp Asn
                245                 250                 255

Asn Asn Ile Pro Ala Leu Val Tyr Ala Leu Gln Asn Gly Gln Thr Val
            260                 265                 270

Val Ser Arg Asp Pro Phe Lys Ala Val Thr Phe Val Ala Asn His Asp
        275                 280                 285

Thr Asp Ile Ile Trp Asn Lys Tyr Pro Ala Tyr Ala Phe Ile Leu Thr
    290                 295                 300

Tyr Glu Gly Gln Pro Val Ile Phe Tyr Arg Asp Phe Glu Glu Trp Leu
305                 310                 315                 320

Asn Lys Asp Lys Leu Ile Asn Leu Ile Trp Ile His Asp His Leu Ala
                325                 330                 335

Gly Gly Ser Thr Thr Ile Val Tyr Tyr Asp Asn Asp Glu Leu Ile Phe
            340                 345                 350

Val Arg Asn Gly Asp Ser Arg Arg Pro Gly Leu Ile Thr Tyr Ile Asn
        355                 360                 365

Leu Ser Pro Asn Trp Val Gly Arg Trp Val Tyr Val Pro Lys Phe Ala
    370                 375                 380

Gly Ala Cys Ile His Glu Tyr Thr Gly Asn Leu Gly Gly Trp Val Asp
385                 390                 395                 400

Lys Arg Val Asp Ser Ser Gly Trp Val Tyr Leu Glu Ala Pro Pro His
                405                 410                 415

Asp Pro Ala Asn Gly Tyr Tyr Gly Tyr Ser Val Trp Ser Tyr Cys Gly
            420                 425                 430

Val Gly

<210> SEQ ID NO 5
<211> LENGTH: 6105
<212> TYPE: DNA
<213> ORGANISM: Saccharomyces cerevisiae

<400> SEQUENCE: 5
atgtcatcaa aacctgatac tggttcggaa atttctggcc ctcagcgaca ggaagaacaa      60
gaacaacaga tagagcagag ctcacctacg gaagcaaacg atagaagcat tcatgatgag     120
```

-continued

| | | | | |
|---|---|---|---|---|
| gtaccaaaag | tcaagaagcg | tcacgaacaa | aatagtggtc | acaaatcaag aaggaatagc | 180 |
| gcatatagtt | attacagccc | acggtcgctt | tctatgacca | aaagcaggga gagtatcact | 240 |
| ccaaatggta | tggatgatgt | aagtatttcg | aacgtggaac | atccaaggcc gacagaaccg | 300 |
| aaaatcaaaa | ggggtccata | tttactgaag | aaaacattga | gcagtctttc aatgacgagc | 360 |
| gcgaatagta | ctcatgatga | taataaagac | cacggttacg | ctttgaattc atccaagacg | 420 |
| cacaactaca | catctactca | taaccatcat | gacggtcatc | atgatcatca tcatgttcag | 480 |
| ttttttccca | ataggaagcc | atcattagcg | gaaaccctat | tcaaaggtt ttcagggtca | 540 |
| aacagtcacg | atggcaataa | gtcaggaaag | gaaagtaaag | ttgctaacct ttcccttca | 600 |
| acggtaaatc | ctgcacctgc | taataggaaa | ccttctaaag | actccacttt atctaatcac | 660 |
| ttggctgata | acgtgccaag | cactttacga | aggaaagtgt | cctcattggt acgtggttct | 720 |
| tccgtccatg | atataaataa | tggtattgca | gataaacaga | ttagaccaaa gactgttgcg | 780 |
| caatcagaaa | atacattaca | ttcatccgat | gttcccaata | gcaaacgctc gcacagaaaa | 840 |
| agctttctgc | taggctccac | atcttcttca | agcagtagaa | gaggttcaaa tgtcagttca | 900 |
| atgactaaca | gtgacagtgc | aagtatggcg | acgtcgggta | gtcatgttct ccaacataac | 960 |
| gtatctaatg | tttctccaac | tactaaaagt | aaggacagcg | ttaacagcga atccgccgat | 1020 |
| cacactaata | ataaatccga | gaaagtgact | ccagaatata | atgagaacat tccggaaaat | 1080 |
| tctaactctg | acaacaaacg | cgaagccaca | acgcctacta | tagaaacacc catttcatgt | 1140 |
| aaaccatccc | ttttcaggct | agatacaaac | cttgaggatg | ttactgatat tacaaagacg | 1200 |
| gtgccaccca | ccgctgtcaa | ttctacacta | aattctacac | acgggactga gactgcctca | 1260 |
| cccaaaacgg | tgatcatgcc | tgaaggtcct | aggaagtcgg | tgtcaatggc tgatctctcc | 1320 |
| gtcgctgccg | cagcacctaa | tggtgaattc | acatcaactt | ccaatgatag atcacaatgg | 1380 |
| gtagcacctc | aaagctggga | tgtggaaacc | aaaaggaaaa | aacaaaacc taagggaga | 1440 |
| tcgaaatcaa | gaaggtcaag | tatagatgct | gatgaacttg | atcccatgtc accggggcca | 1500 |
| ccttcaaaaa | aagactctcg | tcatcgtaag | aaccgacact | ctcgtcatca tcacgatcga | 1560 |
| aaggataaca | aatcaatggt | cactgcgggt | gacagtaact | caagttttgt tgatatatgt | 1620 |
| aaagaaaacg | ttccgaatga | tagcaagacc | gcactcgata | ctaaatctgt gaaccgctta | 1680 |
| aaaagtaatt | tggctatgag | tcccccaagt | atacgatatg | ctccatcaaa tttagatggg | 1740 |
| gactacgaca | cgtcttccac | ttcctcatct | ttaccgtcct | catctattag ttcagaagat | 1800 |
| acatcttcct | gcagcgattc | ctcttcgtac | actaacgcgt | atatggaggc caaccgagag | 1860 |
| caggataata | aaacaccgat | cctgaataaa | acgaaatcgt | ataccaagaa atttacatcc | 1920 |
| tcttcggtaa | atatgaattc | accagatggt | gcccagagtt | ctggattatt actacaagat | 1980 |
| gagaaggacg | atgaggtcga | gtgccaactg | gaacattact | ataaagattt cagtgattta | 2040 |
| gatccaaaga | ggcactatgc | tattcgtata | ttcaatactg | atgacacttt tacgactctc | 2100 |
| tcatgtactc | cagcgactac | cgtcgaagag | ataatacctg | cacttaaaag aaaatttaac | 2160 |
| attacagcgc | aagggaattt | tcaaattttcc | ctgaaggtgg | gaaagttgtc aaaaattttg | 2220 |
| agaccaactt | cgaaacctat | tttaattgaa | agaaaacttt | tactttttgaa tggttatcga | 2280 |
| aagtcagacc | cacttcatat | tatgggtata | gaggatttaa | gttttgtttt taagtttctt | 2340 |
| ttccatcctg | tcacacctc | tcactttact | cctgaacaag | aacaaagaat aatgagaagc | 2400 |
| gaatttgttc | acgtagattt | aaggaatatg | gatctgacta | cacctcccat catttttac | 2460 |
| cagcatacgt | cagaaataga | aagtttagac | gtttctaata | acgtaaatat attcctacct | 2520 |

-continued

```
ctggagttca ttgaaagctc gattaaatta ttaagtttga gaatggttaa tattagagca    2580
tctaaatttc cttccaatat cactaaggcg tataaactag tatctttgga attacagaga    2640
aacttcataa gaaaagtacc gaactcaatc atgaaactga gtaatttaac gatattaaac    2700
cttcaatgta atgagcttga aagcctaccg gctggatttg ttgaactgaa aaatctgcaa    2760
ttgctagact tgtcttcaaa caagttcatg cactacccag aagttattaa ctactgcacc    2820
aatcttttac aaatagacct atcatataat aaaatccaaa gcttaccaca gtccactaag    2880
tacctagtaa agcttgcgaa gatgaacctt tctcataaca aactaaattt tataggcgac    2940
ttatcggaaa tgacaaattt gaggacgctg aacctaagat ataacagaat atcatcaatt    3000
aagacaaatg cgtctaactt gcagaacctt tttttaacag ataatagaat ttcgaactttt   3060 gaagacactt tgccgaaaact aagagccctt gaaattcaag agaatccaat cacttctata   3120
tccttcaaag attttatcc aaaaaacatg acaagtttga cgttgaacaa ggcacagtta    3180
tcgagtattc ctggagaatt actcaccaaa ctatctttcc tcgagaaact tgaacttaat    3240
cagaataatt tgactagact gccacaggag atatccaagt tgactaaatt agttttcctt    3300
tcagtggcga aaacaaact agagtatatt ccacccgagc tatctcaact gaaaagtttg    3360
aggacattag atctacattc taacaacata agggactttg ttgacggtat ggaaaacctt    3420
gaactaacat cgctaaatat ttcatcgaat gcattcggta actctagctt agaaaattct    3480
ttttaccata acatgtcata tgggtcaaag ttatctaaaa gcctgatgtt ttttattgct    3540
gcagacaatc aatttgatga tgctatgtgg cctctttttca attgctttgt caatctgaaa    3600
gtgctaaatc tttcttacaa caattttttca gatgtatcgc acatgaaact tgagagcatt    3660
accgaattgt acctctccgg taataagctc acgacattgt cgggtgatac agttttgaaa    3720
tggagctctt taaagacttt aatgttgaat agtaaccaaa tgttatctct gcctgcagaa    3780
ttatcaaatc tctcacagct aagtgtattt gatgttggag caaatcaatt aaagtataat    3840
atatcaaact atcattacga ttggaactgg aggaataata agaactaaa atatttgaat    3900 ttttcaggaa atcgaaggtt tgaaataaag tcatttataa gtcacgatat tgatgctgat    3960
ttgtcagatc tgacagtatt acctcagtta aaggtactag gtttaatgga cgtaacttta    4020
aatactacca agtaccgga tgaaaatgtc aatttccgtt taaggacaac tgcatcaata    4080
ataaatggga tgcgctacgg tgttgctgat acattaggtc aaagagacta tgtgtcatct    4140
cgtgatgtta cctttgaaag attccgcgga aatgacgacg aatgcttact atgtcttcat    4200
gatagtaaaa accaaaatgc agattatggc cacaatatat caagaattgt tagagatatt    4260
tacgataaaa tactgatcag acaactggaa aggtatggag acgaaacaga tgataatata    4320
aaaactgcac ttcgtttcag ttttttgcaa ctgaataagg agattaacgg aatgctaaat    4380
tctgttgata atggtgccga tgttgccaat cttttcatatg cagacttgct aagtggcgct    4440
tgctctactg tgatatatat cagagggaag aaactcttcg ctgcaaattt aggtgactgt    4500
atggctattt tatccaaaaa caatggtgac taccaaacgc taaccaaaca acatctccca    4560
acaaagcggg aagaatacga gaggatcaga atatctggcg ggtatgtcaa caatggaaaa    4620
ttagatggtg ttgtagatgt gtctagagca gtgggttttt ttgatttgct tccccacatt    4680
catgcttctc ccgacatatc tgtcgtgaca ttaacaaaag cagacgagat gcttattgta    4740
gcaacgcata agttatggga atacatggac gtggatacag tttgtgatat cgcgcgtgag    4800
aatagtactg atccactccg tgccgcagct gagttgaagg atcatgccat ggcttacggc    4860
tgtacagaga atattacaat tttgtgcctt gctctttacg agaacattca gcaacaaaat    4920
```

-continued

```
cggttcactt taaataaaaa ctctttaatg actagaagaa gtactttcga ggatactaca    4980
ttaagaagac ttcaacctga gatttctccg ccaacaggta acctagcaat ggtcttcact    5040
gatatcaaaa gctcaacctt cttatgggag ctattcccta acgcaatgag gaccgcaata    5100
aaaactcaca atgacattat gcgtcgtcaa ctacgaattt acggtggtta cgaagtaaag    5160
acagaaggag acgcctttat ggtggcattt cctacgccaa ctagtggtct gacatggtgc    5220
ttaagtgttc aattaaaact cttggatgca caatggccgg aggaaattac ctcagttcaa    5280
gacggctgcc aagttacgga tagaaatggt aacattatct atcaaggcct atcagttaga    5340
atgggtattc attggggctg cccagttcca gagcttgatt tagtgactca agaatggac    5400 tatttggggc cgatggtcaa taaggcagca agggtccagg gcgtcgctga cggtggtcag    5460
attgcaatga gtagtgattt ttactctgaa ttcaacaaga taatgaagta tcatgagcga    5520
gtagtgaagg gcaaggaatc tctcaaggaa gtttatggtg aagaaattat cggagaggtt    5580
cttgaaagag aaattgccat gctgaaagt attggttggg cattttttga ctttggcgag    5640
cataagctaa agggactcga aaccaaagaa ctcgttacta ttgcgtatcc taagattctt    5700
gcttccagac acgaatttgc atctgaagat gagcagtcaa aattaatcaa tgaaacgatg    5760
ttgtttcgtt taagagtcat ttcaaacaga ctggaatcta atgtcagc tttaagcggc    5820 ggatttattg aactagactc tcggacggag ggaagttata ttaaatttaa ccctaaagtt    5880
gaaaatggta ttatgcaatc gatttctgag aaggatgcgt tgttattttt tgatcatgta    5940
attactagaa tcgaatccag tgtggcatta ttacatttac gacaacagag gtgttcagga    6000
ctggaaattt gcagaaacga taaaacatct gctcgaagca atattttcaa tgttgttgac    6060
gaacttttac aaatggttaa gaacgcaaag gatttatcaa cttga    6105
```

<210> SEQ ID NO 6
<211> LENGTH: 2034
<212> TYPE: PRT
<213> ORGANISM: Saccharomyces cerevisiae

<400> SEQUENCE: 6

```
Met Ser Ser Lys Pro Asp Thr Gly Ser Glu Ile Ser Gly Pro Gln Arg
1               5                   10                  15

Gln Glu Glu Gln Glu Gln Gln Ile Glu Gln Ser Ser Pro Thr Glu Ala
            20                  25                  30

Asn Asp Arg Ser Ile His Asp Glu Val Pro Lys Val Lys Lys Arg His
        35                  40                  45

Glu Gln Asn Ser Gly His Lys Ser Arg Arg Asn Ser Ala Tyr Ser Tyr
    50                  55                  60

Tyr Ser Pro Arg Ser Leu Ser Met Thr Lys Ser Arg Glu Ser Ile Thr
65                  70                  75                  80

Pro Asn Gly Met Asp Asp Val Ser Ile Ser Asn Val Glu His Pro Arg
                85                  90                  95

Pro Thr Glu Pro Lys Ile Lys Arg Gly Pro Tyr Leu Leu Lys Lys Thr
            100                 105                 110

Leu Ser Ser Leu Ser Met Thr Ser Ala Asn Ser Thr His Asp Asp Asn
        115                 120                 125

Lys Asp His Gly Tyr Ala Leu Asn Ser Ser Lys Thr His Asn Tyr Thr
    130                 135                 140

Ser Thr His Asn His His Asp Gly His His Asp His His His Val Gln
145                 150                 155                 160
```

```
Phe Phe Pro Asn Arg Lys Pro Ser Leu Ala Glu Thr Leu Phe Lys Arg
                165                 170                 175
Phe Ser Gly Ser Asn Ser His Asp Gly Asn Lys Ser Gly Lys Glu Ser
            180                 185                 190
Lys Val Ala Asn Leu Ser Leu Ser Thr Val Asn Pro Ala Pro Ala Asn
        195                 200                 205
Arg Lys Pro Ser Lys Asp Ser Thr Leu Ser Asn His Leu Ala Asp Asn
    210                 215                 220
Val Pro Ser Thr Leu Arg Arg Lys Val Ser Ser Leu Val Arg Gly Ser
225                 230                 235                 240
Ser Val His Asp Ile Asn Asn Gly Ile Ala Asp Lys Gln Ile Arg Pro
                245                 250                 255
Lys Thr Val Ala Gln Ser Glu Asn Thr Leu His Ser Ser Asp Val Pro
            260                 265                 270
Asn Ser Lys Arg Ser His Arg Lys Ser Phe Leu Leu Gly Ser Thr Ser
        275                 280                 285
Ser Ser Ser Ser Arg Arg Gly Ser Asn Val Ser Ser Met Thr Asn Ser
    290                 295                 300
Asp Ser Ala Ser Met Ala Thr Ser Gly Ser His Val Leu Gln His Asn
305                 310                 315                 320
Val Ser Asn Val Ser Pro Thr Thr Lys Ser Lys Asp Ser Val Asn Ser
                325                 330                 335
Glu Ser Ala Asp His Thr Asn Asn Lys Ser Lys Val Thr Pro Glu
            340                 345                 350
Tyr Asn Glu Asn Ile Pro Glu Asn Ser Asn Ser Asp Asn Lys Arg Glu
        355                 360                 365
Ala Thr Thr Pro Thr Ile Glu Thr Pro Ile Ser Cys Lys Pro Ser Leu
    370                 375                 380
Phe Arg Leu Asp Thr Asn Leu Glu Asp Val Thr Asp Ile Thr Lys Thr
385                 390                 395                 400
Val Pro Pro Thr Ala Val Asn Ser Thr Leu Asn Ser Thr His Gly Thr
                405                 410                 415
Glu Thr Ala Ser Pro Lys Thr Val Ile Met Pro Glu Gly Pro Arg Lys
            420                 425                 430
Ser Val Ser Met Ala Asp Leu Ser Val Ala Ala Ala Pro Asn Gly
        435                 440                 445
Glu Phe Thr Ser Thr Ser Asn Asp Arg Ser Gln Trp Val Ala Pro Gln
    450                 455                 460
Ser Trp Asp Val Glu Thr Lys Arg Lys Lys Thr Lys Pro Lys Gly Arg
465                 470                 475                 480
Ser Lys Ser Arg Arg Ser Ser Ile Asp Ala Asp Glu Leu Asp Pro Met
                485                 490                 495
Ser Pro Gly Pro Pro Ser Lys Lys Asp Ser Arg His Arg Lys Asn Arg
            500                 505                 510
His Ser Arg His His His Asp Arg Lys Asp Asn Glu Ser Met Val Thr
        515                 520                 525
Ala Gly Asp Ser Asn Ser Ser Phe Val Asp Ile Cys Lys Glu Asn Val
    530                 535                 540
Pro Asn Asp Ser Lys Thr Ala Leu Asp Thr Lys Ser Val Asn Arg Leu
545                 550                 555                 560
Lys Ser Asn Leu Ala Met Ser Pro Pro Ser Ile Arg Tyr Ala Pro Ser
                565                 570                 575
```

```
Asn Leu Asp Gly Asp Tyr Asp Thr Ser Ser Thr Ser Ser Ser Leu Pro
                580                 585                 590

Ser Ser Ser Ile Ser Ser Glu Asp Thr Ser Ser Cys Ser Asp Ser Ser
            595                 600                 605

Ser Tyr Thr Asn Ala Tyr Met Glu Ala Asn Arg Glu Gln Asp Asn Lys
        610                 615                 620

Thr Pro Ile Leu Asn Lys Thr Lys Ser Tyr Thr Lys Lys Phe Thr Ser
625                 630                 635                 640

Ser Ser Val Asn Met Asn Ser Pro Asp Gly Ala Gln Ser Ser Gly Leu
                645                 650                 655

Leu Leu Gln Asp Glu Lys Asp Asp Glu Val Glu Cys Gln Leu Glu His
            660                 665                 670

Tyr Tyr Lys Asp Phe Ser Asp Leu Asp Pro Lys Arg His Tyr Ala Ile
        675                 680                 685

Arg Ile Phe Asn Thr Asp Asp Thr Phe Thr Thr Leu Ser Cys Thr Pro
690                 695                 700

Ala Thr Thr Val Glu Glu Ile Ile Pro Ala Leu Lys Arg Lys Phe Asn
705                 710                 715                 720

Ile Thr Ala Gln Gly Asn Phe Gln Ile Ser Leu Lys Val Gly Lys Leu
                725                 730                 735

Ser Lys Ile Leu Arg Pro Thr Ser Lys Pro Ile Leu Ile Glu Arg Lys
            740                 745                 750

Leu Leu Leu Leu Asn Gly Tyr Arg Lys Ser Asp Pro Leu His Ile Met
        755                 760                 765

Gly Ile Glu Asp Leu Ser Phe Val Phe Lys Phe Leu Phe His Pro Val
770                 775                 780

Thr Pro Ser His Phe Thr Pro Glu Gln Glu Gln Arg Ile Met Arg Ser
785                 790                 795                 800

Glu Phe Val His Val Asp Leu Arg Asn Met Asp Leu Thr Thr Pro Pro
                805                 810                 815

Ile Ile Phe Tyr Gln His Thr Ser Glu Ile Glu Ser Leu Asp Val Ser
            820                 825                 830

Asn Asn Val Asn Ile Phe Leu Pro Leu Glu Phe Ile Glu Ser Ser Ile
        835                 840                 845

Lys Leu Leu Ser Leu Arg Met Val Asn Ile Arg Ala Ser Lys Phe Pro
850                 855                 860

Ser Asn Ile Thr Lys Ala Tyr Lys Leu Val Ser Leu Glu Leu Gln Arg
865                 870                 875                 880

Asn Phe Ile Arg Lys Val Pro Asn Ser Ile Met Lys Leu Ser Asn Leu
                885                 890                 895

Thr Ile Leu Asn Leu Gln Cys Asn Glu Leu Glu Ser Leu Pro Ala Gly
            900                 905                 910

Phe Val Glu Leu Lys Asn Leu Gln Leu Leu Asp Leu Ser Ser Asn Lys
        915                 920                 925

Phe Met His Tyr Pro Glu Val Ile Asn Tyr Cys Thr Asn Leu Leu Gln
930                 935                 940

Ile Asp Leu Ser Tyr Asn Lys Ile Gln Ser Leu Pro Gln Ser Thr Lys
945                 950                 955                 960

Tyr Leu Val Lys Leu Ala Lys Met Asn Leu Ser His Asn Lys Leu Asn
                965                 970                 975

Phe Ile Gly Asp Leu Ser Glu Met Thr Asn Leu Arg Thr Leu Asn Leu
            980                 985                 990
```

-continued

```
Arg Tyr Asn Arg Ile Ser Ser Ile Lys Thr Asn Ala Ser  Asn Leu Gln
        995                 1000                1005

Asn Leu Phe Leu Thr Asp Asn Arg Ile Ser Asn Phe  Glu Asp Thr
   1010                 1015                1020

Leu Pro Lys Leu Arg Ala Leu Glu Ile Gln Glu Asn  Pro Ile Thr
   1025                 1030                1035

Ser Ile Ser Phe Lys Asp Phe Tyr Pro Lys Asn Met  Thr Ser Leu
   1040                 1045                1050

Thr Leu Asn Lys Ala Gln Leu Ser Ser Ile Pro Gly  Glu Leu Leu
   1055                 1060                1065

Thr Lys Leu Ser Phe Leu Glu Lys Leu Glu Leu Asn  Gln Asn Asn
   1070                 1075                1080

Leu Thr Arg Leu Pro Gln Glu Ile Ser Lys Leu Thr  Lys Leu Val
   1085                 1090                1095

Phe Leu Ser Val Ala Arg Asn Lys Leu Glu Tyr Ile  Pro Pro Glu
   1100                 1105                1110

Leu Ser Gln Leu Lys Ser Leu Arg Thr Leu Asp Leu  His Ser Asn
   1115                 1120                1125

Asn Ile Arg Asp Phe Val Asp Gly Met Glu Asn Leu  Glu Leu Thr
   1130                 1135                1140

Ser Leu Asn Ile Ser Ser Asn Ala Phe Gly Asn Ser  Ser Leu Glu
   1145                 1150                1155

Asn Ser Phe Tyr His Asn Met Ser Tyr Gly Ser Lys  Leu Ser Lys
   1160                 1165                1170

Ser Leu Met Phe Phe Ile Ala Ala Asp Asn Gln Phe  Asp Asp Ala
   1175                 1180                1185

Met Trp Pro Leu Phe Asn Cys Phe Val Asn Leu Lys  Val Leu Asn
   1190                 1195                1200

Leu Ser Tyr Asn Asn Phe Ser Asp Val Ser His Met  Lys Leu Glu
   1205                 1210                1215

Ser Ile Thr Glu Leu Tyr Leu Ser Gly Asn Lys Leu  Thr Thr Leu
   1220                 1225                1230

Ser Gly Asp Thr Val Leu Lys Trp Ser Ser Leu Lys  Thr Leu Met
   1235                 1240                1245

Leu Asn Ser Asn Gln Met Leu Ser Leu Pro Ala Glu  Leu Ser Asn
   1250                 1255                1260

Leu Ser Gln Leu Ser Val Phe Asp Val Gly Ala Asn  Gln Leu Lys
   1265                 1270                1275

Tyr Asn Ile Ser Asn Tyr His Tyr Asp Trp Asn Trp  Arg Asn Asn
   1280                 1285                1290

Lys Glu Leu Lys Tyr Leu Asn Phe Ser Gly Asn Arg  Arg Phe Glu
   1295                 1300                1305

Ile Lys Ser Phe Ile Ser His Asp Ile Asp Ala Asp  Leu Ser Asp
   1310                 1315                1320

Leu Thr Val Leu Pro Gln Leu Lys Val Leu Gly Leu  Met Asp Val
   1325                 1330                1335

Thr Leu Asn Thr Thr Lys Val Pro Asp Glu Asn Val  Asn Phe Arg
   1340                 1345                1350

Leu Arg Thr Thr Ala Ser Ile Ile Asn Gly Met Arg  Tyr Gly Val
   1355                 1360                1365

Ala Asp Thr Leu Gly Gln Arg Asp Tyr Val Ser Ser  Arg Asp Val
   1370                 1375                1380
```

```
Thr Phe Glu Arg Phe Arg Gly Asn Asp Asp Glu Cys Leu Leu Cys
1385                1390                1395

Leu His Asp Ser Lys Asn Gln Asn Ala Asp Tyr Gly His Asn Ile
1400                1405                1410

Ser Arg Ile Val Arg Asp Ile Tyr Asp Lys Ile Leu Ile Arg Gln
1415                1420                1425

Leu Glu Arg Tyr Gly Asp Glu Thr Asp Asp Asn Ile Lys Thr Ala
1430                1435                1440

Leu Arg Phe Ser Phe Leu Gln Leu Asn Lys Glu Ile Asn Gly Met
1445                1450                1455

Leu Asn Ser Val Asp Asn Gly Ala Asp Val Ala Asn Leu Ser Tyr
1460                1465                1470

Ala Asp Leu Leu Ser Gly Ala Cys Ser Thr Val Ile Tyr Ile Arg
1475                1480                1485

Gly Lys Lys Leu Phe Ala Ala Asn Leu Gly Asp Cys Met Ala Ile
1490                1495                1500

Leu Ser Lys Asn Asn Gly Asp Tyr Gln Thr Leu Thr Lys Gln His
1505                1510                1515

Leu Pro Thr Lys Arg Glu Glu Tyr Glu Arg Ile Arg Ile Ser Gly
1520                1525                1530

Gly Tyr Val Asn Asn Gly Lys Leu Asp Gly Val Val Asp Val Ser
1535                1540                1545

Arg Ala Val Gly Phe Phe Asp Leu Leu Pro His Ile His Ala Ser
1550                1555                1560

Pro Asp Ile Ser Val Val Thr Leu Thr Lys Ala Asp Glu Met Leu
1565                1570                1575

Ile Val Ala Thr His Lys Leu Trp Glu Tyr Met Asp Val Asp Thr
1580                1585                1590

Val Cys Asp Ile Ala Arg Glu Asn Ser Thr Asp Pro Leu Arg Ala
1595                1600                1605

Ala Ala Glu Leu Lys Asp His Ala Met Ala Tyr Gly Cys Thr Glu
1610                1615                1620

Asn Ile Thr Ile Leu Cys Leu Ala Leu Tyr Glu Asn Ile Gln Gln
1625                1630                1635

Gln Asn Arg Phe Thr Leu Asn Lys Asn Ser Leu Met Thr Arg Arg
1640                1645                1650

Ser Thr Phe Glu Asp Thr Thr Leu Arg Arg Leu Gln Pro Glu Ile
1655                1660                1665

Ser Pro Pro Thr Gly Asn Leu Ala Met Val Phe Thr Asp Ile Lys
1670                1675                1680

Ser Ser Thr Phe Leu Trp Glu Leu Phe Pro Asn Ala Met Arg Thr
1685                1690                1695

Ala Ile Lys Thr His Asn Asp Ile Met Arg Arg Gln Leu Arg Ile
1700                1705                1710

Tyr Gly Gly Tyr Glu Val Lys Thr Glu Gly Asp Ala Phe Met Val
1715                1720                1725

Ala Phe Pro Thr Pro Thr Ser Gly Leu Thr Trp Cys Leu Ser Val
1730                1735                1740

Gln Leu Lys Leu Leu Asp Ala Gln Trp Pro Glu Glu Ile Thr Ser
1745                1750                1755

Val Gln Asp Gly Cys Gln Val Thr Asp Arg Asn Gly Asn Ile Ile
1760                1765                1770
```

```
Tyr Gln Gly Leu Ser Val Arg Met Gly Ile His Trp Gly Cys Pro
    1775                1780                1785
Val Pro Glu Leu Asp Leu Val Thr Gln Arg Met Asp Tyr Leu Gly
    1790                1795                1800
Pro Met Val Asn Lys Ala Ala Arg Val Gln Gly Val Ala Asp Gly
    1805                1810                1815
Gly Gln Ile Ala Met Ser Ser Asp Phe Tyr Ser Glu Phe Asn Lys
    1820                1825                1830
Ile Met Lys Tyr His Glu Arg Val Val Lys Gly Lys Glu Ser Leu
    1835                1840                1845
Lys Glu Val Tyr Gly Glu Glu Ile Ile Gly Glu Val Leu Glu Arg
    1850                1855                1860
Glu Ile Ala Met Leu Glu Ser Ile Gly Trp Ala Phe Phe Asp Phe
    1865                1870                1875
Gly Glu His Lys Leu Lys Gly Leu Glu Thr Lys Glu Leu Val Thr
    1880                1885                1890
Ile Ala Tyr Pro Lys Ile Leu Ala Ser Arg His Glu Phe Ala Ser
    1895                1900                1905
Glu Asp Glu Gln Ser Lys Leu Ile Asn Glu Thr Met Leu Phe Arg
    1910                1915                1920
Leu Arg Val Ile Ser Asn Arg Leu Glu Ser Ile Met Ser Ala Leu
    1925                1930                1935
Ser Gly Gly Phe Ile Glu Leu Asp Ser Arg Thr Glu Gly Ser Tyr
    1940                1945                1950
Ile Lys Phe Asn Pro Lys Val Glu Asn Gly Ile Met Gln Ser Ile
    1955                1960                1965
Ser Glu Lys Asp Ala Leu Leu Phe Phe Asp His Val Ile Thr Arg
    1970                1975                1980
Ile Glu Ser Ser Val Ala Leu Leu His Leu Arg Gln Gln Arg Cys
    1985                1990                1995
Ser Gly Leu Glu Ile Cys Arg Asn Asp Lys Thr Ser Ala Arg Ser
    2000                2005                2010
Asn Ile Phe Asn Val Val Asp Glu Leu Leu Gln Met Val Lys Asn
    2015                2020                2025
Ala Lys Asp Leu Ser Thr
    2030

<210> SEQ ID NO 7
<211> LENGTH: 6105
<212> TYPE: DNA
<213> ORGANISM: Saccharomyces cerevisiae

<400> SEQUENCE: 7
atgtcatcaa aacctgatac tggttcggaa atttctggcc ctcagcgaca ggaagaacaa      60
gaacaacaga tagagcagag ctcgcctacg gaagcaaacg atagaagcat tcatgatgag     120
gtaccaaaag tcaagaagcg tcacgaacaa atagtggtc acaaatcaag aaggaatagc     180
gcatatagtt attacagccc acggtcgctt tctatgacca aaagcaggga gagtatcact     240
ccaaatggta tggatgatgt aagtatttcg aacgtggaac atccaaggcc gacagaaccg     300
aaaatcaaaa ggggtccata tttactgaag aaaacattga gcagtctttc aatgacgagc     360
gcgaatagta ctcatgatga ataaaagac cacggttacg ctttgaattc atccaagacg     420
cacaactaca catctactca taaccatcat gacggtcatc atgatcatca tcatgttcag     480
ttttttccca ataggaagcc atcattagcg gaaaccctat tcaaaaggtt ttcagggtca     540
```

```
aacagtcacg atggcaataa gtcaggaaag gaaagtaaag ttgctaacct ttcccttca    600
acggtaaatc ctgcacctgc taataggaaa ccttctaaag actccacttt atctaatcac   660
ttggctgata acgtgccaag cactttacga aggaaagtgt cctcattggt acgtggttct   720
tccgtccatg atataaataa tggtattgca gataaacaga ttagaccaaa ggctgttgcg   780
caatcagaaa atacattaca ttcatccgat gttcccaata gcaaacgctc gcacagaaaa   840
agctttctgc taggctccac atcttcttca agcagtagaa gaggttcaaa tgtcagttca   900
atgactaaca gtgacagtgc aagtatggcg acgtcgggta gtcatgttct ccaacataac   960
gtatctaatg tttctccaac tactaaaagt aaggacagcg ttaacagcga atccgccgat  1020
cacactaata ataaatccga gaaagtgact ccagaatata atgagaacat tccggaaaat  1080
tctaactctg acaacaaacg cgaagccaca acgcctacta tagaaacacc catttcatgt  1140
aaaccatccc ttttcaggct agatacaaac cttgaggatg ttactgatat tacaaagacg  1200
gtgccaccca ccgctgtcaa ttctacacta aattctacac acgggactga gactgcctca  1260
cccaaaacgg tgatcatgcc tgaaggtcct aggaagtcgg tgtcaatggc tgatctctcc  1320
gtcgctgccg cagcacctaa tggtgaattc acatcaactt ccaatgatag atcacaatgg  1380
gtagcacctc aaagctggga tgtggaaacc aaaaggaaaa aaacaaaacc taagggaga   1440
tcgaaatcaa gaaggtcaag tatagatgct gatgaacttg atcccatgtc accggggcca  1500
ccttcaaaaa aagactctcg tcatcgtaag aaccgacact ctcgtcatca tcacgatcga  1560
aaggataacg aatcaatggt cactgcgggt gacagtaact caagttttgt tgatatatgt  1620
aaagaaaacg ttccgaatga tagcaagacc gcactcgata ctaaatctgt gaaccgctta  1680
aaaagtaatt tggctatgag tcccccaagt atacgatatg ctccatcaaa tttagatggg  1740
gactacgaca cgtcttccac ttcctcatct ttaccgtcct catctattag ttcagaagat  1800
acatcttcct gcagcgattc ctcttcgtac actaacgcgt atatggaggc caaccgagag  1860
caggataata aaacaccgat cctgaataaa acgaaatcgt ataccaagaa atttacatcc  1920
tcttcggtaa atatgaattc accagatggt gcccagagtt ctggattatt actacaagat  1980
gagaaggacg atgaggtcga gtgccaactg gaacattact ataaagattt cagtgattta  2040
gatccaaaga ggcactatgc tattcgtata ttcaatactg atgacacttt tacgactctc  2100
tcatgtactc cagcgactac cgtcgaagag ataatacctg cacttaaaag aaaatttaac  2160
attacagcgc aagggaattt tcaaatttcc ctgaaggtgg gaaagttgtc aaaaattttg  2220
agaccaactt cgaaacctat tttaattgaa agaaaacttt acttttgaa tggttatcga   2280
aagtcagacc cacttcatat tatgggtata gaggatttaa gttttgtttt taagtttctt  2340
ttccatcctg tcacaccttc tcactttact cctgaacaag aacaaagaat aatgagaagc  2400
gaatttgttc acgtagattt aaggaatatg gatctgacta cacctcccat catttttac   2460
cagcatacgt cagaaataga aagtttagac gtttctaata acgcaaatat attcctacct  2520
ctggagttca ttgaaagctc gattaaatta ttaagtttga gaatggttaa tattagagca  2580
tctaaatttc cttccaatat cactgaggcg tataaactag tatctttgga attacagaga  2640
aacttcataa gaaaagtacc gaactcaatc atgaaactga gtaatttaac gatattaaac  2700
cttcaatgta atgagcttga agcctaccg gctggatttg ttgaactgaa aaatctgcaa   2760
ttgctagact tgtcttcaaa caagttcatg cactacccag aagttattaa ctactgcacc  2820
aatctttac aaatagacct atcatataat aaaatccaaa gcttaccaca gtccactaag   2880
tacctagtaa agcttgcgaa gatgaacctt tctcataaca aactaaattt tataggcgac  2940
```

```
ttatcggaaa tgacaaattt gaggacgctg aacctaagat ataacagaat atcatcaatt    3000
aagacaaatg cgtctaactt gcagaacctt tttttaacag ataatagaat ttcgaacttt    3060
gaagacactt tgccgaaact aagagccctt gaaattcaag agaatccaat cacttctata    3120
tccttcaaag attttatcc aaaaaacatg acaagtttga cgttgaacaa ggcacagtta     3180
tcgagtattc ctggagaatt actcaccaaa ctatctttcc tcgagaaact tgaacttaat    3240
cagaataatt tgactagact gccacaggag atatccaagt tgactaaatt agttttcctt    3300
tcagtggcga gaaacaaact agagtatatt ccacccgagc tatctcaact gaaaagtttg    3360
aggacattag atctcattc taacaacata agggactttg ttgacggtat ggaaaacctt     3420
gaactaacat cgctaaatat ttcatcgaat gcattcggta actctagctt agaaaattct    3480
ttttaccata acatgtcata tgggtcaaag ttatctaaaa gcctgatgtt ttttattgct    3540
gcagacaatc aatttgatga tgctatgtgg cctctttca attgctttgt caatctgaaa     3600
gtgctaaatc tttcttacaa caattttca gatgtatcgc acatgaaact tgagagcatt     3660
accgaattgt acctctccgg taataagctc acgacattgt cgggtgatac agttttgaaa    3720
tggagctctt taaagacttt aatgttgaat agtaaccaaa tgttatctct gcctgcagaa    3780
ttatcaaatc tctcacagct aagtgtattt gatgttggag caaatcaatt aaagtataat    3840
atatcaaact atcattacga ttggaactgg aggaataata agaactaaa atatttgaat     3900 ttttcaggaa atcgaaggtt tgaaataaag tcatttataa gtcacgatat tgatgctgat    3960
ttgtcagatc tgacagtatt acctcagtta aaggtactag gtttaatgga cgtaactta     4020 aatactacca agtaccggaa tgaaaatgtc aatttccgtt taaggacaac tgcatcaata    4080
ataaatggga tgcgctacgg tgttgctgat acattaggtc aaagagacta tgtgtcatct    4140
cgtgatgtta cctttgaaag attccgcgga atgacgacg aatgcttact atgtcttcat     4200
gatagtaaaa accaaaatgc agattatggc cacaatatat caagaattgt tagagatatt    4260
tacgataaaa tactgatcag acaactggaa aggtatggag acgacacaga tgataatata    4320
aaaactgcac ttcgtttcag ttttttgcaa ctgaataagg agattaacgg aatgctaaat    4380
tctgttgata atggtgccga tgttgccaat ctttcatatg cagacttgct aagtggcgct    4440
tgctctactg tgatatatat cagagggaag aaactcttcg ctgcaaattt aggtgactgt    4500
atggctattt tatccaaaaa caatggtgac taccaaacgc taaccaaaca acatctccca    4560
acaaagcggg aagaatacga gaggatcaga atatctggcg ggtatgtcaa caatggaaaa    4620
ttagatggtt tgtagatgt gtctagagca gtgggttttt ttgatttgct tccccacatt     4680
catgcttctc ccgacatatc tgtcgtgaca ttaacaaaag cagacgagat gcttattgta    4740
gcaacgcata agttatggga atacatggac gtggatacag tttgtgatat cgcgcgtgag    4800
aatagtactg atccactccg tgccgcagct gagttgaagg atcatgccat ggcttacggc    4860
tgtacagaga atattacaat tttgtgcctt gctctttacg agaacattca gcaacaaat     4920 cggttcactt taaataaaaa ctcttaatg actagaagaa gtactttcga ggatactaca    4980
ttaagaagac ttcaacctga gatttctccg ccaacaggta acctagcaat ggtcttcact    5040
gatatcaaaa gctcaacctt cttatgggag ctattcccta acgcaatgag gaccgcaata    5100
aaaactcaca atgacattat gcgtcgtcaa ctacgaattt acggtggtta cgaagtaaag    5160
acagaaggag acgcctttat ggtggcattt cctacgccaa ctagtggtct tacatggtgc    5220
ttaagtgttc aattaaaact cttggatgca caatggccgg aggaaattac ctcagttcaa    5280
gacggctgcc aagttacgga tagaaatggt aacattatct atcaaggcct atcagttaga    5340
```

-continued

```
atgggtattc attggggctg cccagttcca gagcttgatt tagtgactca aagaatggac    5400
tatttggggc cgatggtcaa taaggcagca agggtccagg gcgtcgctga cggtggtcag    5460
attgcaatga gtagtgattt ttactctgaa ttcaacaaga taatgaagta tcatgaacga    5520
gtagtgaagg gcaaggaatc tctcaaggaa gtttatggtg aagaaattat cggagaggtt    5580
cttgaaagag aaattgccat gctggaaagt attggttggg cattttttga ctttggcgag    5640
cataagctaa agggactcga aaccaaagaa ctcgttacta ttgcgtatcc taagattctt    5700
gcttccagac acgaatttgc atctgaagat gagcagtcaa aattaatcaa tgaaacgatg    5760
ttgtttcatt taagagtcat ttcaaacaga ctggaatcta aatgtcagc tttaagcggc    5820 ggatttattg aactagactc tcggacggag ggaagttata ttaaatttaa ccctaaagtt    5880
gaaaatggta ttatgcaatc gatttctgag aaggatgcgt tgttattttt tgatcatgta    5940
attactagaa tcgaatccag tgtggcatta ttacatttac gacaacagag gtgttcagga    6000
ctggaaattt gcagaaacga taaaacatct gctcgaagca atattttcaa tgttgttgac    6060
gaacttttac aaatggttaa gaacgcaaag gatttatcaa cttga                   6105
```

<210> SEQ ID NO 8
<211> LENGTH: 2034
<212> TYPE: PRT
<213> ORGANISM: Saccharomyces cerevisiae

<400> SEQUENCE: 8

```
Met Ser Ser Lys Pro Asp Thr Gly Ser Glu Ile Ser Gly Pro Gln Arg
1               5                   10                  15

Gln Glu Gln Glu Gln Gln Ile Glu Gln Ser Ser Pro Thr Glu Ala
            20                  25                  30

Asn Asp Arg Ser Ile His Asp Glu Val Pro Lys Val Lys Lys Arg His
        35                  40                  45

Glu Gln Asn Ser Gly His Lys Ser Arg Arg Asn Ser Ala Tyr Ser Tyr
    50                  55                  60

Tyr Ser Pro Arg Ser Leu Ser Met Thr Lys Ser Arg Glu Ser Ile Thr
65                  70                  75                  80

Pro Asn Gly Met Asp Asp Val Ser Ile Ser Asn Val Glu His Pro Arg
                85                  90                  95

Pro Thr Glu Pro Lys Ile Lys Arg Gly Pro Tyr Leu Leu Lys Lys Thr
            100                 105                 110

Leu Ser Ser Leu Ser Met Thr Ser Ala Asn Ser Thr His Asp Asp Asn
        115                 120                 125

Lys Asp His Gly Tyr Ala Leu Asn Ser Ser Lys Thr His Asn Tyr Thr
    130                 135                 140

Ser Thr His Asn His His Asp Gly His His Asp His His Val Gln
145                 150                 155                 160

Phe Phe Pro Asn Arg Lys Pro Ser Leu Ala Glu Thr Leu Phe Lys Arg
                165                 170                 175

Phe Ser Gly Ser Asn Ser His Asp Gly Asn Lys Ser Gly Lys Glu Ser
            180                 185                 190

Lys Val Ala Asn Leu Ser Leu Ser Thr Val Pro Ala Pro Ala Asn
        195                 200                 205

Arg Lys Pro Ser Lys Asp Ser Thr Leu Ser Asn His Leu Ala Asp Asn
    210                 215                 220

Val Pro Ser Thr Leu Arg Arg Lys Val Ser Ser Leu Val Arg Gly Ser
225                 230                 235                 240
```

```
Ser Val His Asp Ile Asn Asn Gly Ile Ala Asp Lys Gln Ile Arg Pro
                245                 250                 255

Lys Ala Val Ala Gln Ser Glu Asn Thr Leu His Ser Ser Asp Val Pro
            260                 265                 270

Asn Ser Lys Arg Ser His Arg Lys Ser Phe Leu Leu Gly Ser Thr Ser
        275                 280                 285

Ser Ser Ser Ser Arg Arg Gly Ser Asn Val Ser Ser Met Thr Asn Ser
    290                 295                 300

Asp Ser Ala Ser Met Ala Thr Ser Gly Ser His Val Leu Gln His Asn
305                 310                 315                 320

Val Ser Asn Val Ser Pro Thr Thr Lys Ser Lys Asp Ser Val Asn Ser
                325                 330                 335

Glu Ser Ala Asp His Thr Asn Asn Lys Ser Glu Lys Val Thr Pro Glu
            340                 345                 350

Tyr Asn Glu Asn Ile Pro Glu Asn Ser Asn Ser Asp Asn Lys Arg Glu
        355                 360                 365

Ala Thr Thr Pro Thr Ile Glu Thr Pro Ile Ser Cys Lys Pro Ser Leu
    370                 375                 380

Phe Arg Leu Asp Thr Asn Leu Glu Asp Val Thr Asp Ile Thr Lys Thr
385                 390                 395                 400

Val Pro Pro Thr Ala Val Asn Ser Thr Leu Asn Ser Thr His Gly Thr
                405                 410                 415

Glu Thr Ala Ser Pro Lys Thr Val Ile Met Pro Glu Gly Pro Arg Lys
            420                 425                 430

Ser Val Ser Met Ala Asp Leu Ser Val Ala Ala Ala Pro Asn Gly
        435                 440                 445

Glu Phe Thr Ser Thr Ser Asn Asp Arg Ser Gln Trp Val Ala Pro Gln
    450                 455                 460

Ser Trp Asp Val Glu Thr Lys Arg Lys Thr Lys Pro Lys Gly Arg
465                 470                 475                 480

Ser Lys Ser Arg Arg Ser Ser Ile Asp Ala Asp Glu Leu Asp Pro Met
                485                 490                 495

Ser Pro Gly Pro Pro Ser Lys Lys Asp Ser Arg His Arg Lys Asn Arg
            500                 505                 510

His Ser Arg His His His Asp Arg Lys Asp Asn Glu Ser Met Val Thr
        515                 520                 525

Ala Gly Asp Ser Asn Ser Ser Phe Val Asp Ile Cys Lys Glu Asn Val
    530                 535                 540

Pro Asn Asp Ser Lys Thr Ala Leu Asp Thr Lys Ser Val Asn Arg Leu
545                 550                 555                 560

Lys Ser Asn Leu Ala Met Ser Pro Pro Ser Ile Arg Tyr Ala Pro Ser
                565                 570                 575

Asn Leu Asp Gly Asp Tyr Asp Thr Ser Ser Thr Ser Ser Ser Leu Pro
            580                 585                 590

Ser Ser Ser Ile Ser Ser Glu Asp Thr Ser Ser Cys Ser Asp Ser Ser
        595                 600                 605

Ser Tyr Thr Asn Ala Tyr Met Glu Ala Asn Arg Glu Gln Asp Asn Lys
    610                 615                 620

Thr Pro Ile Leu Asn Lys Thr Lys Ser Tyr Thr Lys Lys Phe Thr Ser
625                 630                 635                 640

Ser Ser Val Asn Met Asn Ser Pro Asp Gly Ala Gln Ser Ser Gly Leu
                645                 650                 655
```

```
Leu Leu Gln Asp Glu Lys Asp Asp Glu Val Glu Cys Gln Leu Glu His
            660                 665                 670

Tyr Tyr Lys Asp Phe Ser Asp Leu Asp Pro Lys Arg His Tyr Ala Ile
        675                 680                 685

Arg Ile Phe Asn Thr Asp Asp Thr Phe Thr Thr Leu Ser Cys Thr Pro
    690                 695                 700

Ala Thr Thr Val Glu Glu Ile Ile Pro Ala Leu Lys Arg Lys Phe Asn
705                 710                 715                 720

Ile Thr Ala Gln Gly Asn Phe Gln Ile Ser Leu Lys Val Gly Lys Leu
                725                 730                 735

Ser Lys Ile Leu Arg Pro Thr Ser Lys Pro Ile Leu Ile Glu Arg Lys
            740                 745                 750

Leu Leu Leu Leu Asn Gly Tyr Arg Lys Ser Asp Pro Leu His Ile Met
                755                 760                 765

Gly Ile Glu Asp Leu Ser Phe Val Phe Lys Phe Leu Phe His Pro Val
        770                 775                 780

Thr Pro Ser His Phe Thr Pro Glu Gln Glu Gln Arg Ile Met Arg Ser
785                 790                 795                 800

Glu Phe Val His Val Asp Leu Arg Asn Met Asp Leu Thr Thr Pro Pro
                805                 810                 815

Ile Ile Phe Tyr Gln His Thr Ser Glu Ile Glu Ser Leu Asp Val Ser
            820                 825                 830

Asn Asn Ala Asn Ile Phe Leu Pro Leu Glu Phe Ile Glu Ser Ser Ile
                835                 840                 845

Lys Leu Leu Ser Leu Arg Met Val Asn Ile Arg Ala Ser Lys Phe Pro
850                 855                 860

Ser Asn Ile Thr Glu Ala Tyr Lys Leu Val Ser Leu Glu Leu Gln Arg
865                 870                 875                 880

Asn Phe Ile Arg Lys Val Pro Asn Ser Ile Met Lys Leu Ser Asn Leu
                885                 890                 895

Thr Ile Leu Asn Leu Gln Cys Asn Glu Leu Glu Ser Leu Pro Ala Gly
            900                 905                 910

Phe Val Glu Leu Lys Asn Leu Gln Leu Leu Asp Leu Ser Ser Asn Lys
                915                 920                 925

Phe Met His Tyr Pro Glu Val Ile Asn Tyr Cys Thr Asn Leu Leu Gln
930                 935                 940

Ile Asp Leu Ser Tyr Asn Lys Ile Gln Ser Leu Pro Gln Ser Thr Lys
945                 950                 955                 960

Tyr Leu Val Lys Leu Ala Lys Met Asn Leu Ser His Asn Lys Leu Asn
                965                 970                 975

Phe Ile Gly Asp Leu Ser Glu Met Thr Asn Leu Arg Thr Leu Asn Leu
            980                 985                 990

Arg Tyr Asn Arg Ile Ser Ser Ile Lys Thr Asn Ala Ser Asn Leu Gln
            995                 1000                1005

Asn Leu Phe Leu Thr Asp Asn Arg Ile Ser Asn Phe Glu Asp Thr
        1010                1015                1020

Leu Pro Lys Leu Arg Ala Leu Glu Ile Gln Glu Asn Pro Ile Thr
        1025                1030                1035

Ser Ile Ser Phe Lys Asp Phe Tyr Pro Lys Asn Met Thr Ser Leu
        1040                1045                1050

Thr Leu Asn Lys Ala Gln Leu Ser Ser Ile Pro Gly Glu Leu Leu
        1055                1060                1065
```

```
Thr Lys Leu Ser Phe Leu Glu Lys Leu Glu Leu Asn Gln Asn Asn
1070            1075            1080

Leu Thr Arg Leu Pro Gln Glu Ile Ser Lys Leu Thr Lys Leu Val
1085            1090            1095

Phe Leu Ser Val Ala Arg Asn Lys Leu Glu Tyr Ile Pro Pro Glu
1100            1105            1110

Leu Ser Gln Leu Lys Ser Leu Arg Thr Leu Asp Leu His Ser Asn
1115            1120            1125

Asn Ile Arg Asp Phe Val Asp Gly Met Glu Asn Leu Glu Leu Thr
1130            1135            1140

Ser Leu Asn Ile Ser Ser Asn Ala Phe Gly Asn Ser Ser Leu Glu
1145            1150            1155

Asn Ser Phe Tyr His Asn Met Ser Tyr Gly Ser Lys Leu Ser Lys
1160            1165            1170

Ser Leu Met Phe Phe Ile Ala Ala Asp Asn Gln Phe Asp Asp Ala
1175            1180            1185

Met Trp Pro Leu Phe Asn Cys Phe Val Asn Leu Lys Val Leu Asn
1190            1195            1200

Leu Ser Tyr Asn Asn Phe Ser Asp Val Ser His Met Lys Leu Glu
1205            1210            1215

Ser Ile Thr Glu Leu Tyr Leu Ser Gly Asn Lys Leu Thr Thr Leu
1220            1225            1230

Ser Gly Asp Thr Val Leu Lys Trp Ser Ser Leu Lys Thr Leu Met
1235            1240            1245

Leu Asn Ser Asn Gln Met Leu Ser Leu Pro Ala Glu Leu Ser Asn
1250            1255            1260

Leu Ser Gln Leu Ser Val Phe Asp Val Gly Ala Asn Gln Leu Lys
1265            1270            1275

Tyr Asn Ile Ser Asn Tyr His Tyr Asp Trp Asn Trp Arg Asn Asn
1280            1285            1290

Lys Glu Leu Lys Tyr Leu Asn Phe Ser Gly Asn Arg Arg Phe Glu
1295            1300            1305

Ile Lys Ser Phe Ile Ser His Asp Ile Asp Ala Asp Leu Ser Asp
1310            1315            1320

Leu Thr Val Leu Pro Gln Leu Lys Val Leu Gly Leu Met Asp Val
1325            1330            1335

Thr Leu Asn Thr Thr Lys Val Pro Asp Glu Asn Val Asn Phe Arg
1340            1345            1350

Leu Arg Thr Thr Ala Ser Ile Ile Asn Gly Met Arg Tyr Gly Val
1355            1360            1365

Ala Asp Thr Leu Gly Gln Arg Asp Tyr Val Ser Ser Arg Asp Val
1370            1375            1380

Thr Phe Glu Arg Phe Arg Gly Asn Asp Asp Glu Cys Leu Leu Cys
1385            1390            1395

Leu His Asp Ser Lys Asn Gln Asn Ala Asp Tyr Gly His Asn Ile
1400            1405            1410

Ser Arg Ile Val Arg Asp Ile Tyr Asp Lys Ile Leu Ile Arg Gln
1415            1420            1425

Leu Glu Arg Tyr Gly Asp Asp Thr Asp Asp Asn Ile Lys Thr Ala
1430            1435            1440

Leu Arg Phe Ser Phe Leu Gln Leu Asn Lys Glu Ile Asn Gly Met
1445            1450            1455
```

```
Leu Asn Ser Val Asp Asn Gly Ala Asp Val Ala Asn Leu Ser Tyr
1460                1465                1470

Ala Asp Leu Leu Ser Gly Ala Cys Ser Thr Val Ile Tyr Ile Arg
1475                1480                1485

Gly Lys Lys Leu Phe Ala Ala Asn Leu Gly Asp Cys Met Ala Ile
1490                1495                1500

Leu Ser Lys Asn Asn Gly Asp Tyr Gln Thr Leu Thr Lys Gln His
1505                1510                1515

Leu Pro Thr Lys Arg Glu Glu Tyr Glu Arg Ile Arg Ile Ser Gly
1520                1525                1530

Gly Tyr Val Asn Asn Gly Lys Leu Asp Gly Val Val Asp Val Ser
1535                1540                1545

Arg Ala Val Gly Phe Phe Asp Leu Leu Pro His Ile His Ala Ser
1550                1555                1560

Pro Asp Ile Ser Val Val Thr Leu Thr Lys Ala Asp Glu Met Leu
1565                1570                1575

Ile Val Ala Thr His Lys Leu Trp Glu Tyr Met Asp Val Asp Thr
1580                1585                1590

Val Cys Asp Ile Ala Arg Glu Asn Ser Thr Asp Pro Leu Arg Ala
1595                1600                1605

Ala Ala Glu Leu Lys Asp His Ala Met Ala Tyr Gly Cys Thr Glu
1610                1615                1620

Asn Ile Thr Ile Leu Cys Leu Ala Leu Tyr Glu Asn Ile Gln Gln
1625                1630                1635

Gln Asn Arg Phe Thr Leu Asn Lys Asn Ser Leu Met Thr Arg Arg
1640                1645                1650

Ser Thr Phe Glu Asp Thr Thr Leu Arg Arg Leu Gln Pro Glu Ile
1655                1660                1665

Ser Pro Pro Thr Gly Asn Leu Ala Met Val Phe Thr Asp Ile Lys
1670                1675                1680

Ser Ser Thr Phe Leu Trp Glu Leu Phe Pro Asn Ala Met Arg Thr
1685                1690                1695

Ala Ile Lys Thr His Asn Asp Ile Met Arg Arg Gln Leu Arg Ile
1700                1705                1710

Tyr Gly Gly Tyr Glu Val Lys Thr Glu Gly Asp Ala Phe Met Val
1715                1720                1725

Ala Phe Pro Thr Pro Thr Ser Gly Leu Thr Trp Cys Leu Ser Val
1730                1735                1740

Gln Leu Lys Leu Leu Asp Ala Gln Trp Pro Glu Glu Ile Thr Ser
1745                1750                1755

Val Gln Asp Gly Cys Gln Val Thr Asp Arg Asn Gly Asn Ile Ile
1760                1765                1770

Tyr Gln Gly Leu Ser Val Arg Met Gly Ile His Trp Gly Cys Pro
1775                1780                1785

Val Pro Glu Leu Asp Leu Val Thr Gln Arg Met Asp Tyr Leu Gly
1790                1795                1800

Pro Met Val Asn Lys Ala Ala Arg Val Gln Gly Val Ala Asp Gly
1805                1810                1815

Gly Gln Ile Ala Met Ser Ser Asp Phe Tyr Ser Glu Phe Asn Lys
1820                1825                1830

Ile Met Lys Tyr His Glu Arg Val Val Lys Gly Lys Glu Ser Leu
1835                1840                1845
```

| | | | | | | | | | | | |
|---|---|---|---|---|---|---|---|---|---|---|---|
| Lys | Glu | Val | Tyr | Gly | Glu | Ile | Ile | Gly | Glu | Leu | Glu | Arg |
| 1850 | | | | | 1855 | | | | 1860 | | | |
| Glu | Ile | Ala | Met | Leu | Glu | Ser | Ile | Gly | Trp | Ala | Phe | Phe | Asp | Phe |
| 1865 | | | | | 1870 | | | | 1875 | | | |
| Gly | Glu | His | Lys | Leu | Lys | Gly | Leu | Glu | Thr | Lys | Glu | Leu | Val | Thr |
| 1880 | | | | | 1885 | | | | 1890 | | | |
| Ile | Ala | Tyr | Pro | Lys | Ile | Leu | Ala | Ser | Arg | His | Glu | Phe | Ala | Ser |
| 1895 | | | | | 1900 | | | | 1905 | | | |
| Glu | Asp | Glu | Gln | Ser | Lys | Leu | Ile | Asn | Glu | Thr | Met | Leu | Phe | His |
| 1910 | | | | | 1915 | | | | 1920 | | | |
| Leu | Arg | Val | Ile | Ser | Asn | Arg | Leu | Glu | Ser | Ile | Met | Ser | Ala | Leu |
| 1925 | | | | | 1930 | | | | 1935 | | | |
| Ser | Gly | Gly | Phe | Ile | Glu | Leu | Asp | Ser | Arg | Thr | Glu | Gly | Ser | Tyr |
| 1940 | | | | | 1945 | | | | 1950 | | | |
| Ile | Lys | Phe | Asn | Pro | Lys | Val | Glu | Asn | Gly | Ile | Met | Gln | Ser | Ile |
| 1955 | | | | | 1960 | | | | 1965 | | | |
| Ser | Glu | Lys | Asp | Ala | Leu | Leu | Phe | Phe | Asp | His | Val | Ile | Thr | Arg |
| 1970 | | | | | 1975 | | | | 1980 | | | |
| Ile | Glu | Ser | Ser | Val | Ala | Leu | Leu | His | Leu | Arg | Gln | Gln | Arg | Cys |
| 1985 | | | | | 1990 | | | | 1995 | | | |
| Ser | Gly | Leu | Glu | Ile | Cys | Arg | Asn | Asp | Lys | Thr | Ser | Ala | Arg | Ser |
| 2000 | | | | | 2005 | | | | 2010 | | | |
| Asn | Ile | Phe | Asn | Val | Val | Asp | Glu | Leu | Leu | Gln | Met | Val | Lys | Asn |
| 2015 | | | | | 2020 | | | | 2025 | | | |
| Ala | Lys | Asp | Leu | Ser | Thr |
| 2030 | | | | | |